United States Patent
Ross et al.

(10) Patent No.: US 6,335,367 B1
(45) Date of Patent: Jan. 1, 2002

(54) FUNGICIDAL AND INSECTICIDAL BENZYLOXY CYCLOPROPYL SUBSTITUTED AROMATIC COMPOUNDS

(75) Inventors: Ronald Ross, Jamison; Ted Tsutomu Fujimoto, Churchville; Duyan Vuong Nguyen, Philadelphia; Steven Howard Shaber, Horsham, all of PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/558,314

(22) Filed: Apr. 25, 2000

Related U.S. Application Data

(60) Provisional application No. 60/132,651, filed on May 5, 1999.

(51) Int. Cl.$^7$ .................................................. A01N 37/44
(52) U.S. Cl. ..................... 514/538; 514/532; 514/617; 514/619; 560/8; 560/35; 564/161; 564/163
(58) Field of Search .................. 514/532, 538, 514/617, 619; 560/8, 35; 564/161, 163

(56) References Cited

U.S. PATENT DOCUMENTS

| | | | | |
|---|---|---|---|---|
| 5,166,399 A | * | 11/1992 | Schuetz et al. | 560/35 |
| 5,358,968 A | * | 10/1994 | Oberdorf et al. | 514/620 |
| 5,545,664 A | * | 8/1996 | Kirstgen et al. | 514/521 |
| 5,945,557 A | * | 8/1999 | Ross et al. | 560/52 |

FOREIGN PATENT DOCUMENTS

| | | |
|---|---|---|
| EP | 0 579 124 A1 | 1/1994 |
| EP | 889024 * 1/1999 | C07C/69/736 |

* cited by examiner

Primary Examiner—Gary Geist
Assistant Examiner—M. P. Moon
(74) Attorney, Agent, or Firm—Thomas D. Rogerson

(57) ABSTRACT

Compounds with fungicidal and insecticidal properties having the following formula:

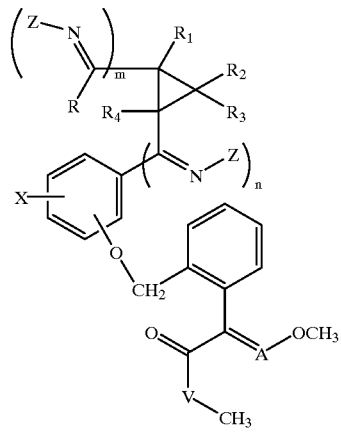

wherein A is N or CH; V is O or NH; m and n are the integers 0 and 1, and m+n is 1; X is independently selected from hydrogen, halo, ($C_1$–$C_4$)alkyl, and ($C_1$–$C_4$)alkoxy; Z is $NR_5R_6$, $OR_5$ or $CR_7R_8R_9$; and R, $R_1$, $R_2$, $R_3$, $R_4$, $R_5$, $R_6$, $R_7$, $R_8$ and $R_9$ vary.

10 Claims, No Drawings

FUNGICIDAL AND INSECTICIDAL BENZYLOXY CYCLOPROPYL SUBSTITUTED AROMATIC COMPOUNDS

This application claims priority under 35 U.S.C. §119(e) of commonly owned Provisional Application Serial No. 60/132,651 filed May 5, 1999, the disclosure of which is hereby incorporated herein by reference.

The present invention relates to benzyloxy cyclopropyl substituted phenyl compounds, compositions containing these compounds and methods for controlling fungi and insects by the use of a fungitoxic or insecticidal amount of these compounds.

It is known that propenoic acids and oxime ethers of certain benzyloxy substituted phenyl compounds are useful as fungicides. The substitution of the phenyl ring by oximes are known in the art (see for example U.S. Pat. No. 5,166,399 and U.S. Pat. No. 5,358,968).

We have discovered phenyl derivatives which possess a substituted cyclopropyl moiety. These novel derivatives also possess fungicidal and insecticidal properties.

The novel benzyloxy substituted phenyl compounds of the present invention have the Formula (I)

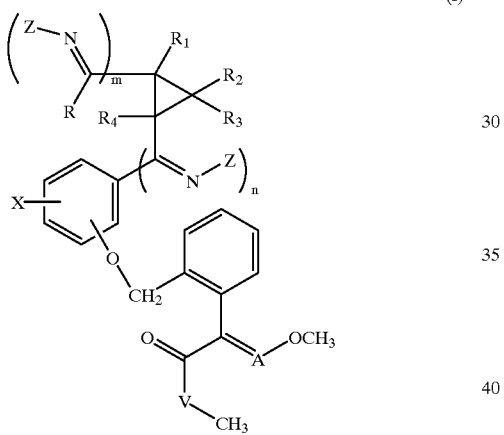

wherein A is N or CH; V is O or NH;

m and n are the integers 0 and 1, provided that m+n is 1;

X is selected from the group consisting of hydrogen, halo, $(C_1-C_4)$alkyl, and $(C_1-C_4)$alkoxy;

Z is $NR_5R_6$, $OR_5$ or $CR_7R_8R_9$, provided that when Z=$OR_5$, n=0;

R is selected from the group consisting of hydrogen, $(C_1-C_{12})$alkyl, $(C_1-C_{12})$alkoxy, halo$(C_1-C_{12})$alkyl, $(C_2-C_2)$alkenyl, halo$(C_2-C_{12})$alkenyl, $(C_2-C_{12})$alkynyl, halo$(C_2-C_{12})$alkynyl, halo$(C_1-C_{12})$-alkoxy, $(C_1-C_{12})$alkoxy$(C_1-C_{12})$alkyl, halo$(C_1-C_{12})$alkoxy $(C_1-C_{12})$ alkyl, $(C_3-C_7)$cycloalkyl, halo$(C_3-C_7)$cycloalkyl, $(C_3-C_7)$cycloalkyl$(C_1-C_{12})$alkyl, $(C_3-C_7)$cycloalkyl$(C_2-C_{12})$alkenyl, $(C_3-C_7)$cycloalkyl $(C_2-C_{12})$ alkynyl, $(C_1-C_{12})$alkyl$(C_3-C_7)$cycloalkyl, $(C_1-C_{12})$alkoxy$(C_3-C_7)$cycloalkyl, $(C_1-C_{12})$alkoxy $(C_1-C_{12})$alkyl$(C_3-C_7)$cycloalkyl, $(C_2-C_{12})$alkenyl $(C_3-C_7)$cycloalkyl, $(C_2-C_{12})$ alkynyl$(C_3-C_7)$ cycloalkyl, halo$(C_1-C_{12})$alkyl$(C_3-C_7)$cycloalkyl, $(C_1-C_{12})$alkoxy$(C_2-C_{12})$alkenyl$(C_3-C_7)$cycloalkyl, $(C_1-C_{12})$alkoxy$(C_2-C_{12})$alkynyl$(C_3-C_7)$cycloalkyl, $(C_3-C_7)$cycloalkyl$(C_3-C_7)$-cycloalkyl, $(C_1-C_{12})$alkyl $(C_3-C_7)$cycloalkyl$(C_3-C_7)$cycloalkyl, $(C_2-C_{12})$alkenyl $(C_3-C_7)$cycloalkyl$(C_3-C_7)$cycloalkyl, $(C_2-C_{12})$alkynyl $(C_3-C_7)$cycloalkyl$(C_3-C_7)$cycloalkyl, $(C_3-C_7)$ cycloalkyl$(C_1-C_{12})$alkyl$(C_3-C_7)$cycloalkyl, $(C_3-C_7)$ cycloalkyl$(C_2-C_{12})$alkenyl$(C_3-C_7)$cycloalkyl, $(C_3-C_7)$ cycloalkyl$(C_2-C_{12})$alkynyl$(C_3-C_7)$cycloalkyl, $(C_3-C_7)$ cycloalkyl$(C_1-C_{12})$ alkoxy$(C_3-C_7)$cycloalkyl, $(C_3-C_7)$ cycloalkyl$(C_1-C_{12})$alkoxy$(C_1-C_{12})$alkyl$(C_3-C_7)$ cycloalkyl, $(C_3-C_7)$cycloalkyl$(C_1-C_{12})$alkoxy $(C_2-C_{12})$alkenyl$(C_3-C_7)$cycloalkyl, $(C_3-C_7)$cycloalkyl $(C_1-C_{12})$ alkoxy$(C_2-C_{12})$alkynyl$(C_3-C_7)$cycloalkyl, aryl, aralkyl, aryl$(C_3-C_7)$cycloalkyl, aryl$(C_3-C_7)$ cycloalkyl$(C_3-C_7)$cycloalkyl, $(C_3-C_7)$cycloalkylaryl, aryl$(C_1-C_4)$alkyl$(C_3-C_7)$cycloalkyl, heterocyclic, aryl $(C_1-C_4)$alkylheterocyclic, heterocyclic$(C_1-C_4)$alkyl, heterocyclic$(C_3-C_7)$ cycloalkyl, and $C(R_{11})$=N— $OR_{10}$ provided that when n=1, R and $R_1$ are not both hydrogen;

$R_1$ and $R_4$ are independently selected from the group consisting of hydrogen, halogen, $(C_1-C_{12})$alkyl, $(C_1-C_{12})$alkoxy, halo$(C_1-C_{12})$alkyl, $(C_2-C_{12})$alkenyl, $(C_2-C_{12})$alkynyl, $(C_3-C_7)$cycloalkyl, cyano, carboxy, $(C_1-C_4)$alkoxycarbonyl, $(C_1-C_{12})$alkylcarbonyl, and aryl;

$R_2$ and $R_3$ are selected such that when taken together $R_2$ and $R_3$ form a $(C_3-C_7)$cycloalkyl ring; or are each independently selected from the group consisting of hydrogen, halogen, $(C_1-C_{12})$alkyl, $(C_1-C_{12})$alkoxy, halo$(C_1-C_{12})$alkyl, $(C_2-C_{12})$alkenyl, $(C_2-C_{12})$alkynyl, $(C_3-C_7)$cycloalkyl, cyano, carboxy, $(C_1-C_4)$ alkoxycarbonyl, $(C_1-C_{12})$alkylcarbonyl, and aryl;

$R_5$ and $R_6$ are $(C_1-C_{12})$alkyl, $(C_1-C_{12})$alkoxy, halo $(C_1-C_{12})$alkyl, $(C_2-C_{12})$alkenyl, halo$(C_2-C_{12})$ alkenyl, $(C_2-C_{12})$alkynyl, halo$(C_2-C_{12})$alkynyl, halo$(C_1-C_{12})$-alkoxy, $(C_1-C_{12})$alkoxy$(C_1-C_{12})$ alkyl, $(C_3-C_7)$cycloalkyl, halo$(C_3-C_7)$cycloalkyl, $(C_1-C_4)$alkoxycarbonyl, $(C_1-C_{12})$alkylcarbonyl, arylcarbonyl, aryl, aralkyl, heterocyclic and heterocyclic$(C_1-C_4)$alkyl;

$R_7$, $R_8$, and $R_9$ are independently selected from the group consisting of hydrogen, $(C_1-C_{12})$alkyl, $(C_1-C_{12})$alkoxy, halo$(C_1-C_{12})$alkyl, $(C_2-C_{12})$alkenyl, halo$(C_2-C_{12})$alkenyl, $(C_2-C_{12})$alkynyl, halo$(C_2-C_{12})$alkynyl, halo$(C_1-C_{12})$ alkoxy, $(C_1-C_{12})$alkoxy$(C_1-C_{12})$alkyl, $(C_3-C_7)$cycloalkyl, halo$(C_1-C_7)$cycloalkyl, cyano, $(C_1-C_4)$alkoxycarbonyl, $(C_1-C_{12})$alkylcarbonyl, arylcarbonyl, aryl, aralkyl, heterocyclic and heterocyclic$(C_1-C_4)$alkyl;

$R_{10}$ is selected from the group consisting of hydrogen, $(C_1-C_{12})$alkyl, halo$(C_1-C_{12})$alkyl, $(C_2-C_{12})$alkenyl, halo$(C_2-C_{12})$alkenyl, $(C_2-C_{12})$alkynyl, halo $(C_2-C_{12})$alkynyl, $(C_1-C_4)$alkylcarbonyl, $(C_1-C_4)$ alkoxycarbonyl, aryl, and aralkyl;

$R_{11}$ is selected from the group consisting of hydrogen, $(C_1-C_{12})$alkyl, halo$(C_1-C_{12})$alkyl, $(C_3-C_7)$ cycloalkyl, halo$(C_3-C_7)$cycloalkyl, $(C_2-C_{12})$ alkenyl, halo $C_2-C_{12})$alkenyl, $(C_2-C_{12})$alkynyl, halo $(C_2-C_{12})$alkynyl, aryl, aralkyl, heterocyclic, and heterocyclic$(C_1-C_4)$alkyl.

The aforementioned $(C_1-C_{12})$alkyl, $(C_1-C_{12})$alkoxy, $(C_2-C_{12})$alkenyl, $(C_2-C_{12})$alkynyl and $(C_3-C_7)$cycloalkyl groups may be optionally substituted with up to three substituents selected from the group consisting of halogen, nitro, trihalomethyl and cyano.

Unless otherwise qualified, the term alkyl includes both branched and straight chain alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

Unless otherwise qualified, the term alkoxy includes both branched and straight chain alkyl groups from 1 to 12 carbon atoms containing at least one oxygen atom. Typical alkoxy groups are methoxy, ethoxy, n-propoxy, iso-propoxy, n-butoxy, sec-butoxy isobutoxyl, t-butoxy, n-pentoxy, isopentoxy, n-hexoxy, n-heptoxy and the like. The term haloalkoxy refers to an alkoxy group substituted with 1 to 3 halogens.

Unless otherwise qualified, the term alkenyl refers to an ethylenically unsaturated hydrocarbon group, straight or branched, having a chain length of 2 to 12 carbon atoms and 1 or 2 ethylenic bonds. The term haloalkenyl refers to an alkenyl group substituted with 1 to 3 halogen atoms. The term alkynyl refers to an unsaturated hydrocarbon group, straight or branched, having a chain length of 2 to 12 carbon atoms and 1 or 2 acetylenic bonds.

The term cycloalkyl refers to a saturated ring system having 3 to 7 carbon atoms.

The term aryl includes phenyl or naphthyl, which maybe substituted with up to three substituents independently selected from the group consisting of halogen, cyano, nitro, trihalomethyl, phenyl, phenoxy, $(C_1-C_6)$alkyl, $(C_1-C_4)$alkylthio, $(C_1-C_4)$alkylsulfoxide, $(C_1-C_6)$alkoxy and halo $(C_1-C_4)$alkyl.

Typical aryl substituents include but are not limited to 4-chlorophenyl, 4-fluorophenyl, 4-bromophenyl, 2-methoxyphenyl, 2-methylphenyl, 3-methylphenyl, 4-methylphenyl, 2, 4-dibromophenyl, 3, 5-difluorophenyl, 2, 4, 6-trichlorophenyl, 4-methoxyphenyl, 2-chloronaphthyl, 2, 4-dimethoxyphenyl, 4-(trifluoromethyl)phenyl and 2-iodo-4-methylphenyl.

The term heterocyclic refers to a substituted or unsubstituted 5 or 6 membered unsaturated ring containing one, two or three heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of heterocycles includes but is not limited to 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isooxazolyl, thiazolyl, isothiazolyl, oxadiazolyl, thiadiazolyl, quinolyl and isoquinolyl. The heterocyclic ring may be optionally substituted with up to two substituents independently selected from $(C_1-C_2)$ alkyl, halogen, cyano, nitro and trihalomethyl.

Unless otherwise qualified, the term aralkyl is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2, 4-dichlorobenzyl, 2, 4-dibromobenzyl, 2-methylbenzyl, 3-methylbenzyl, and 4-methylbenzyl. Typical phenethyl moieties are 2-(2-chlorophenyl)ethyl, 2-(3-chlorophenyl)ethyl, 2-(4-chlorophenyl)ethyl, 2-(2-fluorophenyl)ethyl, 2-(3-fluorophenyl)ethyl, 2-(4-fluorophenyl)ethyl, 2-(2-25 methylphenyl)ethyl, 2-(3-methylphenyl)-ethyl, 2-(4-methylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2, 4-dichlorophenyl)ethyl, 2-(3, 5-dimethoxyphenyl)ethyl. Typical phenpropyl moieties are 3-phenylpropyl, 3-(2-chloro-phenyl)propyl, 3-(3-chlorophenyl)propyl, 3-(4-chlorophenyl)propyl, 3-(2, 4-dichlorophenyl)-propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)ethyl, 3-(2-methoxy-phenyl)propyl, 3-(3-methoxyphenyl)propyl, 3-(4-methoxyphenyl)propyl, 3-(4-trifluoromethyl-phenyl)propyl, 3-(2, 4-dichlorophenyl)propyl and 3-(3, 5-dimethoxyphenyl)propyl. Typical phenbutyl moieties include are 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)-butyl, 4-(2-methylphenyl)butyl, 4-(3-methylphenyl)butyl, 4-(4-methylphenyl)butyl, 4-(2, 4-dichlorophenyl)butyl, 4-(2-methoxphenyl)butyl, 4-(3-methoxyphenyl)butyl and 4-(4-methoxy-phenyl)butyl.

Halogen or halo is meant to include iodo, fluoro, bromo and chloro moieties.

Because of the C=N double bonds the novel compounds of the general Formula I may be obtained in preparation as E/Z isomeric mixtures. These isomers can be separated into individual components by conventional means. The cyclopropanes of Formula I may be obtained in preparation as cis- and trans- isomeric mixtures which can be separated into individual components by conventional means. Both the individual isomeric compounds and mixtures thereof form subjects of the invention and can be used as fungicides.

A preferred embodiment of this invention are the compounds, enantiomorphs and salts of Formula (I) where is X is hydrogen and R is $(C_1-C_{12})$alkyl, $(C_2-C_{12})$alkenyl, $(C_2-C_{12})$alkynyl, $(C_3-C_7)$cycloalkyl, $(C_3-C_7)$cycloalkyl $(C_1-C_{12})$alkyl, $(C_3-C_7)$cycloalkyl$(C_2-C_{12})$alkenyl, $(C_1-C_{12})$alkyl$(C_3-C_7)$cycloalkyl, $(C_2-C_{12})$alkenyl$(C_3-C_7)$cycloalkyl, phenyl substituted with preferably one or two substituents independently selected from halo, trihalomethyl, cyano, $(C_1-C_4)$alkyl, $(C_1-C_4)$alkylthio, $(C_1-C_4)$alkoxy or phenyl, where the OCH$_2$(2-substitutedphenyl) is bonded at the meta position to the (C=N—Z)n-cyclopropyl ring substituent of the phenyl ring as shown in Formula I'.

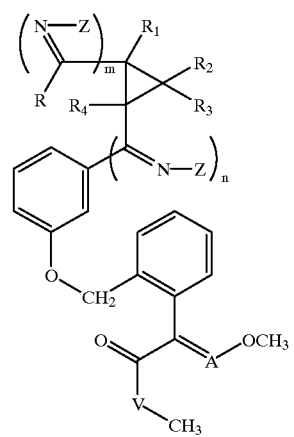

A more preferred embodiment of this invention are the compounds, enantiomorphs, salts and complexes of Formula (I') where n is zero, m is one, Z is OR$_5$, R is $(C_3-C_7)$ cycloalkyl, phenyl substituted with preferably one or two substituents independently selected from halo or trihalomethyl, R$_1$, R$_2$, R$_3$ and R$_4$ are hydrogen and A is N and V is NH. The preferred geometry when A is N is the E isomer as shown in Formula $I''$.

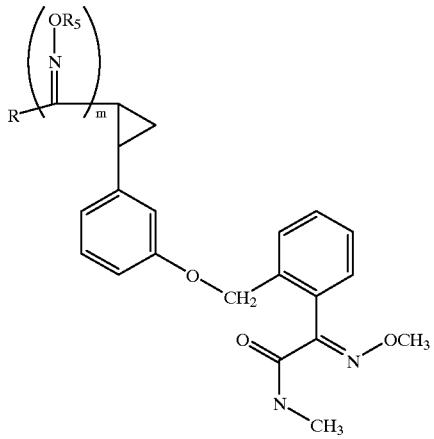

Typical compounds encompassed by the present invention of Formula I ($X=H$, $R_1=R_2=R_3=R_4=H$) and include those compounds presented in Table 1 of Formula II, III and IV (Z is $OR_5$, $n=0$, $m=1$) where R and $R_5$ are defined in Table 1.

TABLE 1

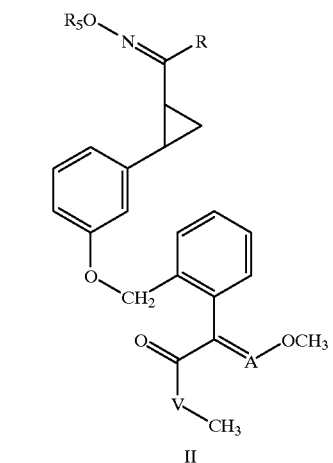

II

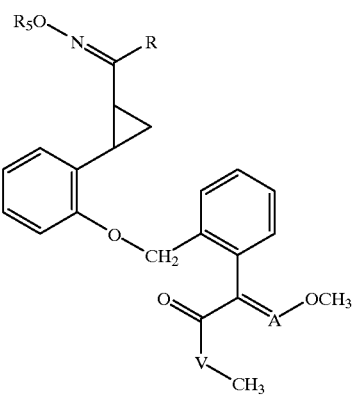

III

TABLE 1-continued

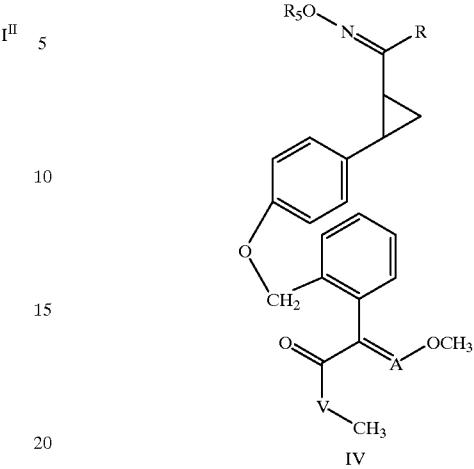

IV

| Cmpd # | R | Formula | $R_5$ | A | V |
|---|---|---|---|---|---|
| 1.01 | Ph | II | $CH_3$ | CH | O |
| 1.02 | Ph | III | $CH_3$ | CH | O |
| 1.03 | Ph | IV | $CH_3$ | CH | O |
| 1.04 | 4-Cl(Ph) | II | $CH_3$ | CH | O |
| 1.05 | 4-Cl(Ph) | III | $CH_3$ | CH | O |
| 1.06 | 4-Cl(Ph) | IV | $CH_3$ | CH | O |
| 1.07 | 2-Cl(Ph) | II | $CH_3$ | CH | O |
| 1.08 | 3-Cl(Ph) | II | $CH_3$ | CH | O |
| 1.09 | 2-F(Ph) | II | $CH_3$ | CH | O |
| 1.10 | 4-F(Ph) | II | $CH_3$ | CH | O |
| 1.11A | 2-$CH_3$(Ph) | II | $CH_3$ | CH | O |
| 1.11B | 2-$CH_3$(Ph) | II | $CH_3$ | CH | O |
| 1.12 | 3-$CH_3$(Ph) | II | $CH_3$ | CH | O |
| 1.13 | 4-$CH_3$(Ph) | II | $CH_3$ | CH | O |
| 1.14 | 4-$CH_3O$(Ph) | II | $CH_3$ | CH | O |
| 1.15 | 2-$CH_3O$(Ph) | II | $CH_3$ | CH | O |
| 1.16 | 2,5-Cl(Ph) | II | $CH_3$ | CH | O |
| 1.17 | 3,4-Cl(Ph) | II | $CH_3$ | CH | O |
| 1.18A | $CH_3$ | II | $CH_3$ | CH | O |
| 1.18B | $CH_3$ | II | $CH_3$ | CH | O |
| 1.19 | $CH_3CH_2$ | II | $CH_3$ | CH | O |
| 1.20 | $CH_3CH_2CH_2$ | II | $CH_3$ | CH | O |
| 1.21 | $(CH_3)_2CH$ | II | $CH_3$ | CH | O |
| 1.22 | $CH_3(CH_2)_2CH_2$ | II | $CH_3$ | CH | O |
| 1.23 | $CH_3(CH_2)_4CH_2$ | II | $CH_3$ | CH | O |
| 1.24 | $(CH_3)_2CHCH_2$ | II | $CH_3$ | CH | O |
| 1.25 | $CH_3CH_2(CH_3)CH$ | II | $CH_3$ | CH | O |
| 1.26 | $(CH_3)_3C$ | II | $CH_3$ | CH | O |
| 1.27 | $CH_3(CH_2)_3CH_2$ | II | $CH_3$ | CH | O |
| 1.28 | $CH_3CH_2CH_2(CH_3)CH$ | II | $CH_3$ | CH | O |
| 1.29 | $(CH_3)_2CHCH_2CH_2$ | II | $CH_3$ | CH | O |
| 1.30 | $CF_3$ | II | $CH_3$ | CH | O |
| 1.31 | $CF_3CH_2$ | II | $CH_3$ | CH | O |
| 1.32 | $CH_2=CH$ | II | $CH_3$ | CH | O |
| 1.33 | 4'-methyl-cyclohex-3-en-1-yl | II | $CH_3$ | CH | O |
| 1.34 | cyclopropyl | II | $CH_3$ | CH | O |
| 1.35 | cyclopentyl | II | $CH_3$ | CH | O |
| 1.36 | cyclohexyl | II | $CH_3$ | CH | O |
| 1.37 | $CH_2=C$(cyclopropyl) | II | $CH_3$ | CH | O |
| 1.38 | $CH_3$—CH=C(cyclopropyl) | II | $CH_3$ | CH | O |
| 1.39 | $CH_3O$—CH=C(cyclopropyl) | II | $CH_3$ | CH | O |
| 1.40 | $C_2H_5$—CH=C(cyclopropyl) | II | $CH_3$ | CH | O |
| 1.41 | $CH_2=C(CH(CH_3)_2)$ | II | $CH_3$ | CH | O |
| 1.42 | $CH_3CH=C(CH(CH_3)_2)$ | II | $CH_3$ | CH | O |
| 1.43 | pyridin-3-yl | II | $CH_3$ | CH | O |
| 1.44 | pyridmidin-2-yl | II | $CH_3$ | CH | O |
| 1.45 | thien-2-yl | II | $CH_3$ | CH | O |
| 1.46 | thien-3-yl | II | $CH_3$ | CH | O |
| 1.47 | 2-napthyl | II | $CH_3$ | CH | O |
| 1.48 | 2-furyl | II | $CH_3$ | CH | O |
| 1.49 | 3-furyl | II | $CH_3$ | CH | O |
| 1.50 | 2-methylcyclopropyl | II | $CH_3$ | CH | O |
| 1.51 | 2-ethylcyclopropyl | II | $CH_3$ | CH | O |

TABLE 1-continued

| | | | | | |
|---|---|---|---|---|---|
| 1.52 | 2-(n-propyl)cyclopropyl | II | $CH_3$ | CH | O |
| 1.53 | 2-(n-butyl)-cyclopropyl | II | $CH_3$ | CH | O |
| 1.54 | 2-(iso-butyl)cyclopropyl | II | $CH_3$ | CH | O |
| 1.55 | 2-(sec-butyl)cyclopropyl | II | $CH_3$ | CH | O |
| 1.56 | 2-(n-pentyl)cyclopropyl | II | $CH_3$ | CH | O |
| 1.57 | 2-(iso-pentyl)cyclopropyl | II | $CH_3$ | CH | O |
| 1.58 | 2-(n-hexyl)cyclopropyl | II | $CH_3$ | CH | O |
| 1.59 | 2-methoxycyclopropyl | II | $CH_3$ | CH | O |
| 1.60 | 2-ethoxycyclopropyl | II | $CH_3$ | CH | O |
| 1.61 | 2-(n-propoxy)cyclopropyl | II | $CH_3$ | CH | O |
| 1.62 | 1-methylcyclopropyl | II | $CH_3$ | CH | O |
| 1.63 | 2-($CH=CH_2$)cyclopropyl | II | $CH_3$ | CH | O |
| 1.64 | 2-(1-cyclopropyl)cyclopropyl | II | $CH_3$ | CH | O |
| 1.65 | 2-(2-cyclopropyl)cyclopropyl | II | $CH_3$ | CH | O |
| 1.66 | cyclopropyl-$CH_2$ | II | $CH_3$ | CH | O |
| 1.67 | cyclopropyl-$CH=CH$ | II | $CH_3$ | CH | O |
| 1.68 | 2-((2'-$CH_3$)cyclopropyl)cyclopropyl) | II | $CH_3$ | CH | O |
| 1.69 | 2-(2'-$CH=CH_2$)cyclopropyl)cyclopropyl | II | $CH_3$ | CH | O |
| 1.70 | 1-(Ph)cyclopropyl | II | $CH_3$ | CH | O |
| 1.71 | 2-(Ph)cyclopropyl | II | $CH_3$ | CH | O |
| 1.72 | 1-(2'-Cl(Ph))cyclopropyl | II | $CH_3$ | CH | O |
| 1.73 | 2-(2'-Cl(Ph))cyclopropyl | II | $CH_3$ | CH | O |
| 1.74 | 1-(3'-Cl(Ph))cyclopropyl | II | $CH_3$ | CH | O |
| 1.75 | 2-(3'-Cl(Ph))cyclopropyl | II | $CH_3$ | CH | O |
| 1.76 | 1-(4'-Cl(Ph))cyclopropyl | II | $CH_3$ | CH | O |
| 1.77 | 2-(4'-Cl(Ph))cyclopropyl | II | $CH_3$ | CH | O |
| 1.78 | 1-(2'-F(Ph))cyclopropyl | II | $CH_3$ | CH | O |
| 1.79 | 2-(2'-F(Ph))cyclopropyl | II | $CH_3$ | CH | O |
| 1.80 | 2-(3'-F(Ph))cyclopropyl | II | $CH_3$ | CH | O |
| 1.81 | 2-(4'-F(Ph))cyclopropyl | II | $CH_3$ | CH | O |
| 1.82 | 2-(2'-Br(Ph))cyclopropyl | II | $CH_3$ | CH | O |
| 1.83 | 2-(3'-Br(Ph))cyclopropyl | II | $CH_3$ | CH | O |
| 1.84 | 2-(4'-Br(Ph))cyclopropyl | II | $CH_3$ | CH | O |
| 1.85 | 2-(2'-F(Ph))cyclopropyl | II | $CH_3$ | CH | O |
| 1.86 | 2-(2'-$CH_3$(Ph))cyclopropyl | II | $CH_3$ | CH | O |
| 1.87 | 2-(3'-$CH_3$(Ph))cyclopropyl | II | $CH_3$ | CH | O |
| 1.88 | 2-(4'-$CH_3$(Ph))cyclopropyl | II | $CH_3$ | CH | O |
| 1.89 | 2-(2'-$CF_3$(Ph))cyclopropyl | II | $CH_3$ | CH | O |
| 1.90 | 2-(3'-$CF_3$(Ph))cyclopropyl | II | $CH_3$ | CH | O |
| 1.91 | 2-(4'-$CF_3$(Ph))cyclopropyl | II | $CH_3$ | CH | O |
| 1.92 | $CH_3C(=N-OCH_3)$ | II | $CH_3$ | CH | O |
| 1.93 | $C_2H_5C(=N-OCH_3)$ | II | $CH_3$ | CH | O |
| 1.94 | 2-(Ph)cyclopentyl | II | $CH_3$ | CH | O |
| 1.95 | 2-(Ph)cyclohexyl | II | $CH_3$ | CH | O |
| 1.96 | 2-(2'-(Ph)cyclopropyl)cyclopropyl | II | $CH_3$ | CH | O |
| 1.97 | 2-(1'-(Ph)cyclopropyl)cyclopropyl | II | $CH_3$ | CH | O |
| 1.98 | $PhCH_2$ | II | $CH_3$ | CH | O |
| 1.99 | 4-Cl(Ph)$CH_2$ | II | $CH_3$ | CH | O |
| 1.100 | 4-$CH_3$(Ph)$CH_2$ | II | $CH_3$ | CH | O |
| 1.101 | 2-(Ph$CH_2$)cyclopropyl | II | $CH_3$ | CH | O |
| 1.102 | 2-(2'-Cl(Ph)$CH_2$)cyclopropyl | II | $CH_3$ | CH | O |
| 1.103 | 2-(4'-Cl(Ph)$CH_2$)cyclopropyl | II | $CH_3$ | CH | O |
| 1.104 | 2-(2'-(Ph$CH_2$)cyclopropyl)cyclopropyl | II | $CH_3$ | CH | O |
| 1.105 | 2-(1'-(Ph$CH_2$)cyclopropyl)cyclopropyl | II | $CH_3$ | CH | O |
| 1.106 | 2-(2'-pyridyl)cyclopropyl | II | $CH_3$ | CH | O |
| 1.107 | Ph | II | $CH_3CH_2$ | CH | O |
| 1.108A | cyclopropyl | II | $CH_3CH_2$ | CH | O |
| 1.108B | cyclopropyl | II | $CH_3CH_2$ | CH | O |
| 1.109 | Ph | II | $C(CH_3)_3$ | CH | O |
| 1.110 | cyclopropyl | II | $C(CH_3)_3$ | CH | O |
| 1.111 | Ph | II | $PhCH_2$ | CH | O |
| 1.112 | 4-Cl(Ph) | II | $PhCH_2$ | CH | O |
| 1.113 | 4-F(Ph) | II | $PhCH_2$ | CH | O |
| 1.114 | 4-$CH_3$(Ph) | II | $PhCH_2$ | CH | O |
| 1.115 | cyclopropyl | II | $PhCH_2$ | CH | O |

Further typical compounds described by the present invention are described in the following tables.

Table II: Compounds 2.01 to 2.115 are Compounds of Table 1 of Formula II, III, IV where V=O and A is N.

Table III:

Compounds 3.01 to 3.115 are Compounds of Table 1 of Formula II, III, IV where V=NH and A is N.

Typical compounds encompassed by the present invention of Formula I (X=H, $R_1=R_2=R_3=R_4=H$) and include those compounds presented in Table IV of Formula V, VI and VII (Z is N—$R_5R_6$, n=0, m=1) where R and $R_5$ are defined in Table IV.

TABLE IV

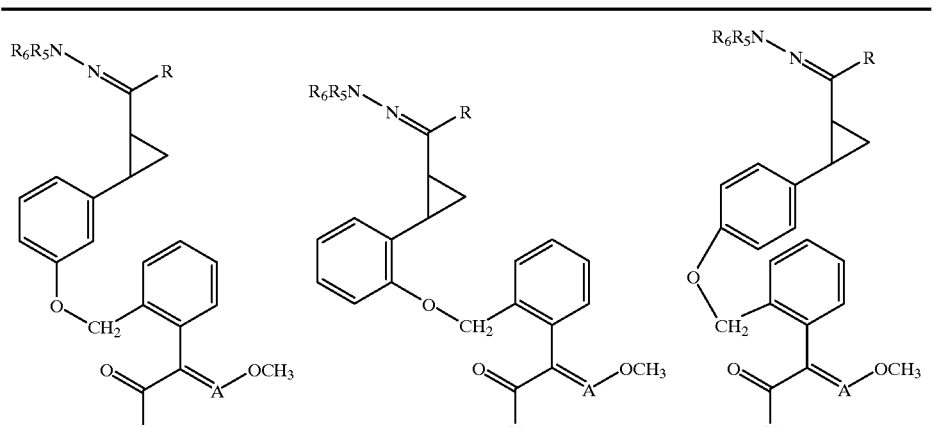

| Cmpd # | R | Formula | $R_5$ | $R_6$ | A | V |
|---|---|---|---|---|---|---|
| 4.01 | Ph | V | $CH_3$ | H | CH | O |
| 4.02 | Ph | VI | $CH_3$ | H | CH | O |
| 4.03 | Ph | VII | $CH_3$ | H | CH | O |
| 4.04 | 4-Cl(Ph) | V | $CH_3$ | H | CH | O |

TABLE IV-continued

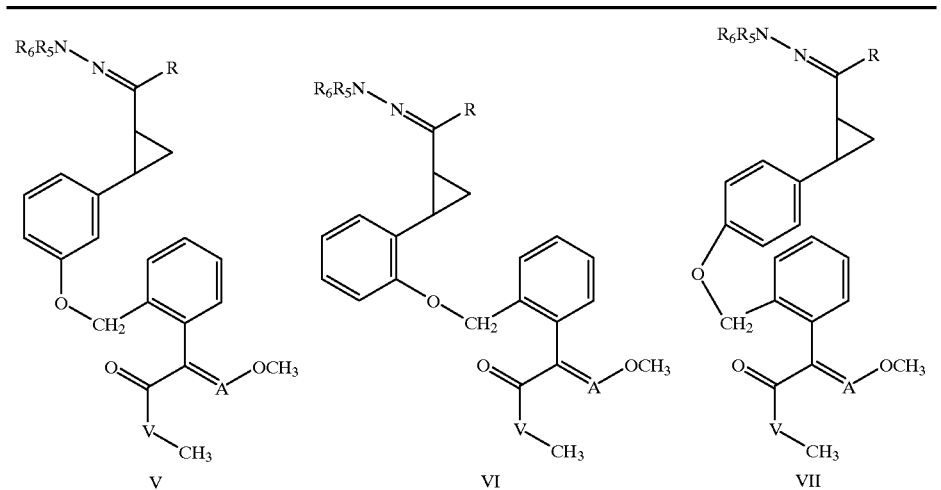

| Cmpd # | R | Formula | $R_5$ | $R_6$ | A | V |
|---|---|---|---|---|---|---|
| 4.05 | 4-Cl(Ph) | VI | $CH_3$ | H | CH | O |
| 4.06 | 4-Cl(Ph) | VII | $CH_3$ | H | CH | O |
| 4.07 | 2-Cl(Ph) | V | $CH_3$ | H | CH | O |
| 4.08 | 3-Cl(Ph) | V | $CH_3$ | H | CH | O |
| 4.09 | 2-F(Ph) | V | $CH_3$ | H | CH | O |
| 4.10 | 4-FPh) | V | $CH_3$ | H | CH | O |
| 4.11 | 4-$CH_3$(Ph) | V | $CH_3$ | H | CH | O |
| 4.12 | 4-$CH_3$O(Ph) | V | $CH_3$ | H | CH | O |
| 4.13 | 2,4-Cl(Ph) | V | $CH_3$ | H | CH | O |
| 4.14 | Ph | V | Ph | H | CH | O |
| 4.15 | 4-Cl(Ph) | V | Ph | H | CH | O |
| 4.16 | $CH_3$ | V | Ph | H | CH | O |
| 4.17 | $CH_3CH_2(CH_3)CH$ | V | Ph | H | CH | O |
| 4.18 | $CH_3$ | V | $CH_3$ | $CH_3$ | CH | O |
| 4.19 | $CH_3CH_2$ | V | $CH_3$ | $CH_3$ | CH | O |
| 4.20 | $CH_3CH_2CH_2$ | V | $CH_3$ | $CH_3$ | CH | O |
| 4.21 | $(CH_3)_2CH$ | V | $CH_3$ | $CH_3$ | CH | O |
| 4.22 | $CH_3(CH_2)_2CH_2$ | V | $CH_3$ | $CH_3$ | CH | O |
| 4.23 | $CH_3(CH_2)_4CH_2$ | V | $CH_3$ | $CH_3$ | CH | O |
| 4.24 | $(CH_3)_2CHCH_2$ | V | $CH_3$ | $CH_3$ | CH | O |
| 4.25 | $CH_3CH_2(CH_3)CH$ | V | $CH_3$ | $CH_3$ | CH | O |
| 4.26 | $(CH_3)_3C$ | V | $CH_3$ | $CH_3$ | CH | O |
| 4.27 | $CH_3(CH_2)_3CH_2$ | V | $CH_3$ | $CH_3$ | CH | O |
| 4.28 | $CH_3CH_2CH_2(CH_3)CH$ | V | $CH_3$ | $CH_3$ | CH | O |
| 4.29 | $(CH_3)_2CHCH_2CH_2$ | V | $CH_3$ | $CH_3$ | CH | O |
| 4.30 | $CH_2{=}CHCH_2CH_2$ | V | $CH_3$ | $CH_3$ | CH | O |
| 4.31 | $CH_2{=}C(CH_3)CH_2CH_2$ | V | $CH_3$ | $CH_3$ | CH | O |
| 4.32 | $CF_3CH_2$ | V | $CH_3$ | $CH_3$ | CH | O |
| 4.33 | $CH_2{=}CH$ | V | $CH_3$ | $CH_3$ | CH | O |
| 4.34 | cyclopropyl | V | $CH_3$ | $CH_3$ | CH | O |
| 4.35 | cyclopentyl | V | $CH_3$ | $CH_3$ | CH | O |
| 4.36 | cyclohexyl | V | $CH_3$ | $CH_3$ | CH | O |
| 4.37 | $CH_3OCH_2$ | V | $CH_3$ | $CH_3$ | CH | O |
| 4.38 | $CH_3S{-}CH(CH_3)$ | V | $CH_3$ | $CH_3$ | CH | O |
| 4.39 | $PhCH_2OCH_2$ | V | $CH_3$ | $CH_3$ | CH | O |
| 4.40 | pyridin-2-yl | V | $CH_3$ | $CH_3$ | CH | O |
| 4.41 | pyridin-3-yl | V | $CH_3$ | $CH_3$ | CH | O |
| 4.42 | pyridin-4-yl | V | $CH_3$ | $CH_3$ | CH | O |
| 4.43 | pyrimidin-2-yl | V | $CH_3$ | $CH_3$ | CH | O |
| 4.44 | pyrimidin-4-yl | V | $CH_3$ | $CH_3$ | CH | O |
| 4.45 | thien-2-yl | V | $CH_3$ | $CH_3$ | CH | O |
| 4.46 | thien-3-yl | V | $CH_3$ | $CH_3$ | CH | O |
| 4.47 | 2-napthyl | V | $CH_3$ | $CH_3$ | CH | O |
| 4.48 | 2-furyl | V | $CH_3$ | $CH_3$ | CH | O |
| 4.49 | Ph | V | $COCH_3$ | H | CH | O |
| 4.50 | 4-Cl(Ph) | V | $COCH_3$ | H | CH | O |
| 4.51 | $CH_3$ | V | $COCH_3$ | H | CH | O |
| 4.52 | 3-furyl | V | $COCH_3$ | H | CH | O |
| 4.53 | 2-methylcyclopropyl | V | $COCH_3$ | H | CH | O |
| 4.54 | 2-ethylcyclopropyl | V | $COCH_3$ | H | CH | O |
| 4.55 | 2-(n-propyl)cyclopropyl | V | $COCH_3$ | H | CH | O |
| 4.56 | 2-(n-butyl)cyclopropyl | V | $COCH_3$ | H | CH | O |
| 4.57 | 2-(iso-butyl)cyclopropyl | V | $COCH_3$ | H | CH | O |

TABLE IV-continued

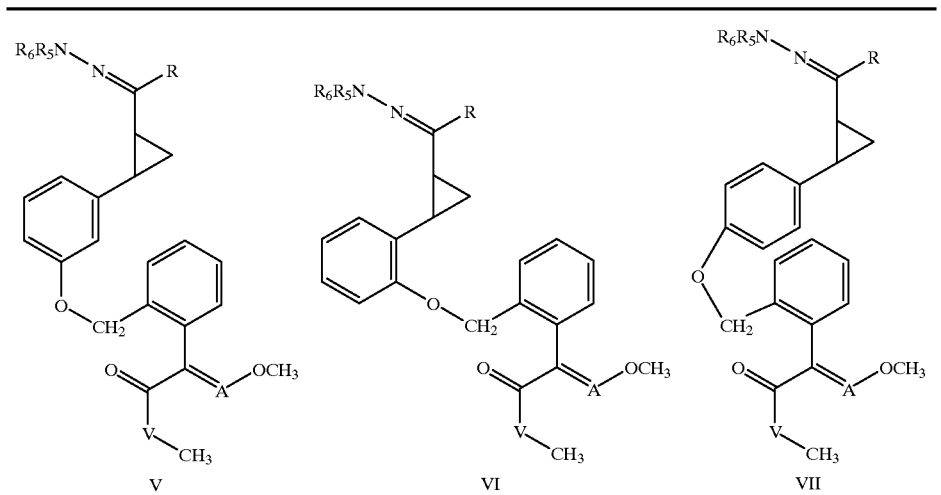

V  VI  VII

| Cmpd # | R | Formula | R₅ | R₆ | A | V |
|---|---|---|---|---|---|---|
| 4.58 | 2-(n-hexyl)cyclopropyl | V | COCH₃ | H | CH | O |
| 4.59 | 2-methoxycyclopropyl | V | COCH₃ | H | CH | O |
| 4.60 | 2-ethoxycyclopropyl | V | COCH₃ | H | CH | O |
| 4.61 | 2-(n-propoxy)cyclopropyl | V | COCH₃ | H | CH | O |
| 4.62 | 1-methylcyclopropyl | V | COCH₃ | H | CH | O |
| 4.63 | 2-(CH=CH₂)cyclopropyl | V | COCH₃ | H | CH | O |
| 4.64 | 1-(cyclopropyl)cyclopropyl | V | COCH₃ | H | CH | O |
| 4.65 | 2-(cyclopropyl)cyclopropyl | V | COCH₃ | H | CH | O |
| 4.66 | cyclopropyl-CH₂ | V | COCH₃ | H | CH | O |
| 4.67 | cyclopropyl-CH=CH— | V | COCH₃ | H | CH | O |
| 4.68 | 2-((2'-CH₃)cyclopropyl)cyclopropyl | V | COCH₃ | H | CH | O |
| 4.69 | 2-(2'-CH=CH₂)cyclopropylcyclopropyl | V | COCH₃ | H | CH | O |
| 4.70 | 1-(Ph)cyclopropyl | V | COCH₃ | CH₃ | CH | O |
| 4.71 | 2-(Ph)cyclopropyl | V | COCH₃ | CH₃ | CH | O |
| 4.72 | 1-(2'-Cl(Ph))cyclopropyl | V | COCH₃ | CH₃ | CH | O |
| 4.73 | 2-(2'-Cl(Ph))cyclopropyl | V | COCH₃ | CH₃ | CH | O |
| 4.74 | 1-(3'-Cl(Ph))cyclopropyl | V | COCH₃ | CH₃ | CH | O |
| 4.75 | 2-(3'-Cl(Ph))cyclopropyl | V | COCH₃ | CH₃ | CH | O |
| 4.76 | 1-(4'-Cl(Ph))cyclopropyl | V | COCH₃ | CH₃ | CH | O |
| 4.77 | 2-(4'-Cl(Ph))cyclopropyl | V | COCH₃ | CH₃ | CH | O |
| 4.78 | 1-(2'-F(Ph))cyclopropyl | V | COCH₃ | CH₃ | CH | O |
| 4.79 | 2-(2'-F(Ph))cyclopropyl | V | COCH₃ | CH₃ | CH | O |
| 4.80 | 2-(3'-F(Ph))cyclopropyl | V | COCH₃ | CH₃ | CH | O |
| 4.81 | 2-(4'-F(Ph))cyclopropyl | V | COCH₃ | CH₃ | CH | O |
| 4.82 | 2-(2'-Br(Ph))cyclopropyl | V | COCH₃ | CH₃ | CH | O |
| 4.83 | 2-(3'-Br(Ph))cyclopropyl | V | COCH₃ | CH₃ | CH | O |
| 4.84 | 2-(4'-Br(Ph))cyclopropyl | V | COCH₃ | CH₃ | CH | O |
| 4.85 | 2-(2'-F(Ph))cyclopropyl | V | COCH₃ | CH₃ | CH | O |
| 4.86 | 2-(2'-CH₃(Ph))cyclopropyl | V | COCH₃ | CH₃ | CH | O |
| 4.87 | 2-(3'-CH₃(Ph))cyclopropyl | V | COCH₃ | CH₃ | CH | O |
| 4.88 | 2-(4'-CH₃Ph)cyclopropyl | V | COCH₃ | CH₃ | CH | O |
| 4.89 | 2-(2'-CF₃(Ph))cyclopropyl | V | COCH₃ | CH₃ | CH | O |
| 4.90 | 2-(3'-CF₃(Ph))cyclopropyl | V | COCH₃ | CH₃ | CH | O |
| 4.91 | 2-(4'-CF₃(Ph))cyclopropyl | V | COCH₃ | CH₃ | CH | O |
| 4.92 | 2-(2'-(Ph)cyclopropyl)cyclopropyl | V | COCH₃ | CH₃ | CH | O |
| 4.93 | 2-(1'-(Ph)cyclopropyl)cyclopropyl | V | COCH₃ | CH₃ | CH | O |
| 4.94 | 2-(Ph)cyclopentyl | V | COCH₃ | CH₃ | CH | O |
| 4.95 | 2-(Ph)cyclohexyl | V | COCH₃ | CH₃ | CH | O |
| 4.96 | CH₃C(=N—OCH₃)— | V | COCH₃ | CH₃ | CH | O |
| 4.97 | C₂H₅C(=N—OCH₃)— | V | COCH₃ | CH₃ | CH | O |
| 4.98 | cyclopropyl | V | COPh | H | CH | O |
| 4.99 | 4-Cl(Ph) | V | COPh | H | CH | O |
| 4.100 | CH₃ | V | COPh | CH₃ | CH | O |
| 4.101 | PhCH₂ | V | COPh | CH₃ | CH | O |
| 4.102 | 2-Cl(Ph)CH₂ | V | COPh | CH₃ | CH | O |
| 4.103 | 4-Cl(Ph)CH₂ | V | COPh | CH₃ | CH | O |
| 4.104 | 4-CH₃(Ph)CH₂ | V | COPh | CH₃ | CH | O |
| 4.105 | 2-(PhCH₂)cyclopropyl | V | COPh | CH₃ | CH | O |
| 4.106 | 2-(2'-Cl(Ph)CH₂)cyclopropyl | V | COPh | CH₃ | CH | O |
| 4.107 | 2-(4'-Cl(Ph)CH₂)cyclopropyl | V | COPh(4-Cl) | CH₃ | CH | O |

TABLE IV-continued

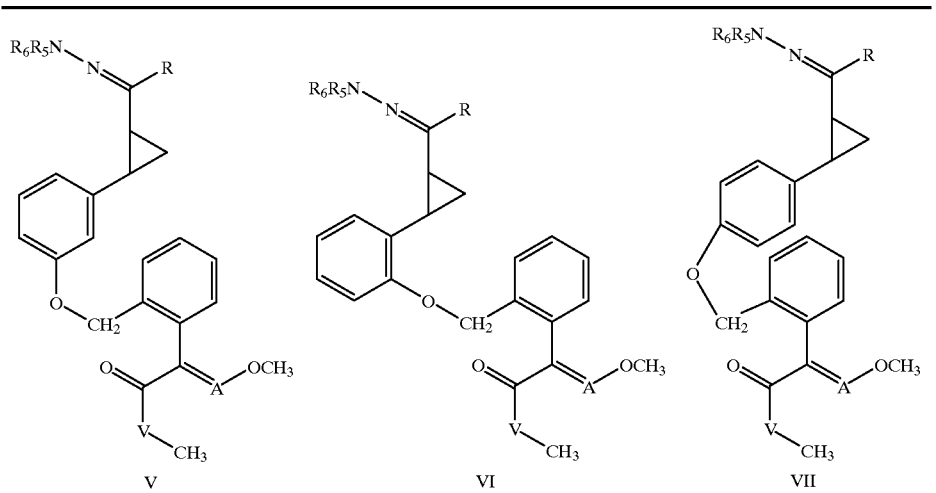

| Cmpd # | R | Formula | $R_5$ | $R_6$ | A | V |
|---|---|---|---|---|---|---|
| 4.108 | 2-(2'-(PhCH$_2$)cyclopropyl)cyclopropyl | V | COPh(4-Cl) | CH$_3$ | CH | O |
| 4.109 | 2-(1'-(PhCH$_2$)cyclopropyl)cyclopropyl | V | COPh(4-Cl) | CH$_3$ | CH | O |
| 4.110 | 2-(2'-pyridyl)cyclopropyl | V | COPh(4-Cl) | CH$_3$ | CH | O |

Further typical compounds described by the present invention are described in the following tables.

Table V:
Compounds 5.01 to 5.110 are Compounds of Table IV of Formula V, VI, VII where V=O and A is N Table VI:
Compounds 6.01 to 6.110 are Compounds of Table IV of Formula V, VI, VII where V=NH and A is N Typical compounds encompassed by the present invention of Formula I (X=H, $R_1$=$R_2$=$R_3$=$R_4$=H) and include those compounds presented in Table VII of Formula VIII, IX and X (Z is N—$R_5R_6$, n=1, m=0) where R and $R_5$ are defined in Table VII.

TABLE VII

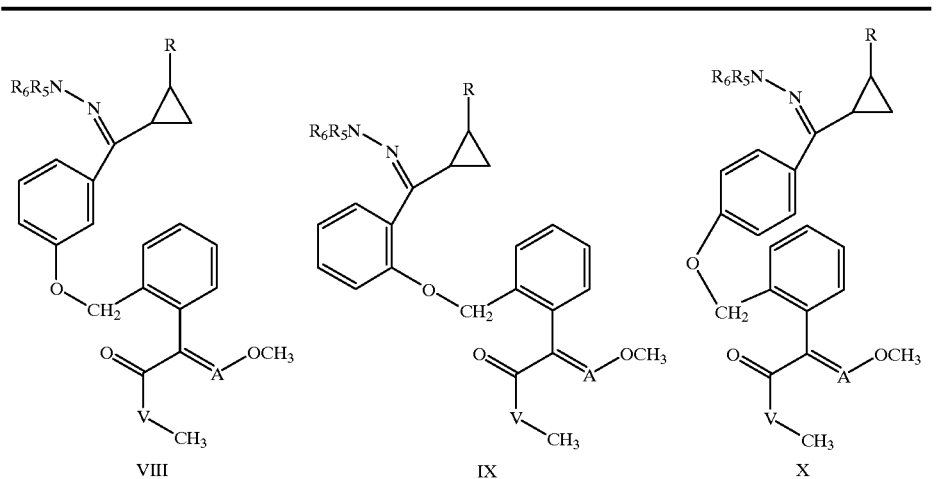

| Cmpd # | R | Formula | $R_5$ | $R_6$ | A | V |
|---|---|---|---|---|---|---|
| 7.01 | Ph | VIII | CH$_3$ | H | CH | O |
| 7.02 | Ph | IX | CH$_3$ | H | CH | O |
| 7.03 | Ph | X | CH$_3$ | H | CH | O |
| 7.04 | 4-Cl(Ph) | VIII | CH$_3$ | H | CH | O |
| 7.05 | 4-Cl(Ph) | IX | CH$_3$ | H | CH | O |
| 7.06 | 4-Cl(Ph) | X | CH$_3$ | H | CH | O |
| 7.07 | 2-Cl(Ph) | VIII | CH$_3$ | H | CH | O |
| 7.08 | 3-Cl(Ph) | IX | CH$_3$ | H | CH | O |

TABLE VII-continued

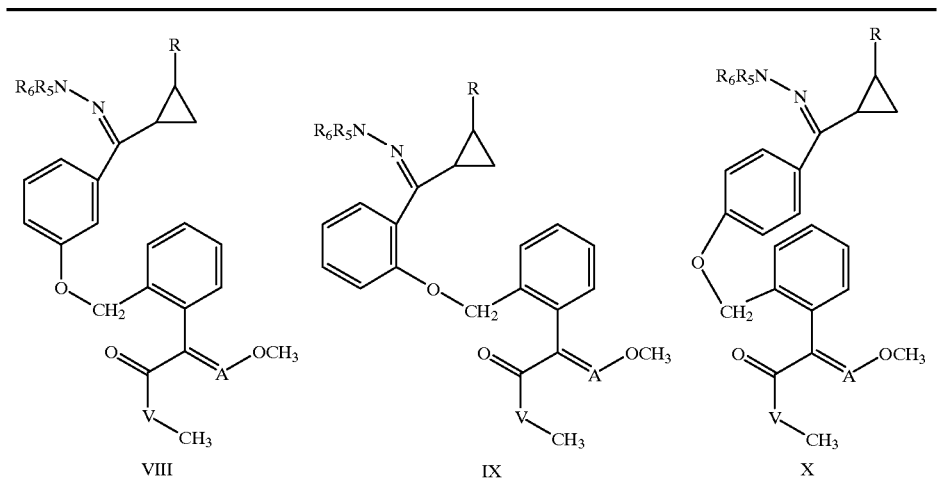

VIII    IX    X

| Cmpd # | R | Formula | R₅ | R₆ | A | V |
|---|---|---|---|---|---|---|
| 7.09 | 2-F(Ph) | VIII | CH₃ | H | CH | O |
| 7.10 | 4-FPh) | VIII | CH₃ | H | CH | O |
| 7.11 | 4-CH₃(Ph) | VIII | CH₃ | H | CH | O |
| 7.12 | 4-CH₃O(Ph) | VIII | CH₃ | H | CH | O |
| 7.13 | 2,4-Cl(Ph) | VIII | CH₃ | H | CH | O |
| 7.14 | Ph | VIII | Ph | H | CH | O |
| 7.15 | 4-Cl(Ph) | VIII | Ph | H | CH | O |
| 7.16 | CH₃ | VIII | Ph | H | CH | O |
| 7.17 | CH₃CH₂(CH₃)CH | VIII | Ph | H | CH | O |
| 7.18 | CH₃ | VIII | CH₃ | CH₃ | CH | O |
| 7.19 | CH₃CH₂ | VIII | CH₃ | CH₃ | CH | O |
| 7.20 | CH₃CH₂CH₂ | VIII | CH₃ | CH₃ | CH | O |
| 7.21 | (CH₃)₂CH | VIII | CH₃ | CH₃ | CH | O |
| 7.22 | CH₃(CH₂)₂CH₂ | VIII | CH₃ | CH₃ | CH | O |
| 7.23 | (CH₃)₂CHCH₂ | VIII | CH₃ | CH₃ | CH | O |
| 7.24 | (CH₃)₃C | VIII | CH₃ | CH₃ | CH | O |
| 7.25 | CH₃CH₂(CH₃)CH | VIII | CH₃ | CH₃ | CH | O |
| 7.26 | CH₃(CH₂)₃CH₂ | VIII | CH₃ | CH₃ | CH | O |
| 7.27 | (CH₃)₂CHCH₂CH₂ | VIII | CH₃ | CH₃ | CH | O |
| 7.28 | CH₃CH₂CH₂(CH₃)CH | VIII | CH₃ | CH₃ | CH | O |
| 7.29 | CH₃CH₂(CH3)₂C | VIII | CH₃ | CH₃ | CH | O |
| 7.30 | CH₂=CHCH₂CH₂ | VIII | CH₃ | CH₃ | CH | O |
| 7.31 | CH₂=C(CH₃)CH₂CH₂ | VIII | CH₃ | CH₃ | CH | O |
| 7.32 | CF₃CH₂ | VIII | CH₃ | CH₃ | CH | O |
| 7.33 | CH₂=CH | VIII | CH₃ | CH₃ | CH | O |
| 7.34 | cyclopropyl | VIII | CH₃ | CH₃ | CH | O |
| 7.35 | cyclopentyl | VIII | CH₃ | CH₃ | CH | O |
| 7.36 | cyclohexyl | VIII | CH₃ | CH₃ | CH | O |
| 7.37 | CH₃OCH₂ | VIII | CH₃ | CH₃ | CH | O |
| 7.38 | CH₃SCH(CH₃) | VIII | CH₃ | CH₃ | CH | O |
| 7.39 | PhCH₂OCH₂ | VIII | CH₃ | CH₃ | CH | O |
| 7.40 | pyridin-2-yl | VIII | CH₃ | CH₃ | CH | O |
| 7.41 | pyridin-3-yl | VIII | CH₃ | CH₃ | CH | O |
| 7.42 | pyridin-4-yl | VIII | CH₃ | CH₃ | CH | O |
| 7.43 | pyrimidin-2-yl | VIII | CH₃ | CH₃ | CH | O |
| 7.44 | pyrimidin-4-yl | VIII | CH₃ | CH₃ | CH | O |
| 7.45 | thien-2-yl | VIII | CH₃ | CH₃ | CH | O |
| 7.46 | thien-3-yl | VIII | CH₃ | CH₃ | CH | O |
| 7.47 | 2-napthyl | VIII | CH₃ | CH₃ | CH | O |
| 7.48 | 2-furyl | VIII | CH₃ | CH₃ | CH | O |
| 7.49 | Ph | VIII | COCH₃ | H | CH | O |
| 7.50 | 4-Cl(Ph) | VIII | COCH₃ | H | CH | O |
| 7.51 | CH₃ | VIII | COCH₃ | H | CH | O |
| 7.52 | 3-furyl | VIII | COCH₃ | H | CH | O |
| 7.53 | 2-methylcyclopropyl | VIII | COCH₃ | H | CH | O |
| 7.54 | 2-ethylcyclopropyl | VIII | COCH₃ | H | CH | O |
| 7.55 | 2-(n-propyl)cyclopropyl | VIII | COCH₃ | H | CH | O |
| 7.56 | 2-(n-butyl)cyclopropyl | VIII | COCH₃ | H | CH | O |
| 7.57 | 2-(iso-butyl)cyclopropyl | VIII | COCH₃ | H | CH | O |
| 7.58 | 2-(n-hexyl)cyclopropyl | VIII | COCH₃ | H | CH | O |
| 7.59 | 2-methoxycyclopropyl | VIII | COCH₃ | H | CH | O |

TABLE VII-continued

| Cmpd # | R | Formula | R₅ | R₆ | A | V |
|---|---|---|---|---|---|---|
| 7.60 | 2-ethoxycyclopropyl | VIII | COCH₃ | H | CH | O |
| 7.61 | 2-(n-propoxy)cyclopropyl | VIII | COCH₃ | H | CH | O |
| 7.62 | 1-methylcyclopropyl | VIII | COCH₃ | H | CH | O |
| 7.63 | 2-(CH=CH₂)cyclopropyl | VIII | COCH₃ | H | CH | O |
| 7.64 | 1-(cyclopropyl)cyclopropyl | VIII | COCH₃ | H | CH | O |
| 7.65 | 2-(cyclopropyl)cyclopropyl | VIII | COCH₃ | H | CH | O |
| 7.66 | cyclopropyl-CH₂ | VIII | COCH₃ | H | CH | O |
| 7.67 | cyclopropyl-CH=CH— | VIII | COCH₃ | H | CH | O |
| 7.68 | 2-((2'-CH₃)cyclopropyl)cyclopropyl | VIII | COCH₃ | H | CH | O |
| 7.69 | 2-(2'-CH=CH₂)cyclopropylcyclopropyl | VIII | COCH₃ | H | CH | O |
| 7.70 | 1-(Ph)cyclopropyl | VIII | COCH₃ | CH₃ | CH | O |
| 7.71 | 2-(Ph)cyclopropyl | VIII | COCH₃ | CH₃ | CH | O |
| 7.72 | 1-(2'-Cl(Ph))cyclopropyl | VIII | COCH₃ | CH₃ | CH | O |
| 7.73 | 2-(2'-Cl(Ph))cyclopropyl | VIII | COCH₃ | CH₃ | CH | O |
| 7.74 | 1-(3'-Cl(Ph))cyclopropyl | VIII | COCH₃ | CH₃ | CH | O |
| 7.75 | 2-(3'-Cl(Ph))cyclopropyl | VIII | COCH₃ | CH₃ | CH | O |
| 7.76 | 1-(4'-Cl(Ph))cyclopropyl | VIII | COCH₃ | CH₃ | CH | O |
| 7.77 | 2-(4'-Cl(Ph))cyclopropyl | VIII | COCH₃ | CH₃ | CH | O |
| 7.78 | 1-(2'-F(Ph))cyclopropyl | VIII | COCH₃ | CH₃ | CH | O |
| 7.79 | 2-(2'-F(Ph))cyclopropyl | VIII | COCH₃ | CH₃ | CH | O |
| 7.80 | 2-(3'-F(Ph))cyclopropyl | VIII | COCH₃ | CH₃ | CH | O |
| 7.81 | 2-(4'-F(Ph))cyclopropyl | VIII | COCH₃ | CH₃ | CH | O |
| 7.82 | 2-(2'-Br(Ph))cyclopropyl | VIII | COCH₃ | CH₃ | CH | O |
| 7.83 | 2-(3'-Br(Ph))cyclopropyl | VIII | COCH₃ | CH₃ | CH | O |
| 7.84 | 2-(4'-Br(Ph))cyclopropyl | VIII | COCH₃ | CH₃ | CH | O |
| 7.85 | 2-(2'-F(Ph))cyclopropyl | VIII | COCH₃ | CH₃ | CH | O |
| 7.86 | 2-(2'-CH₃(Ph))cyclopropyl | VIII | COCH₃ | CH₃ | CH | O |
| 7.87 | 2-(3'-CH₃(Ph))cyclopropyl | VIII | COCH₃ | CH₃ | CH | O |
| 7.88 | 2-(4'-CH₃Ph))cyclopropyl | VIII | COCH₃ | CH₃ | CH | O |
| 7.89 | 2-(2'-CF₃(Ph))cyclopropyl | VIII | COCH₃ | CH₃ | CH | O |
| 7.90 | 2-(3'-CF₃(Ph))cyclopropyl | VIII | COCH₃ | CH₃ | CH | O |
| 7.91 | 2-(4'-CF₃(Ph)cyclopropyl | VIII | COCH₃ | CH₃ | CH | O |
| 7.92 | CH₃C(=N—OCH₃)— | VIII | COCH₃ | CH₃ | CH | O |
| 7.93 | C₂H₅C(=N—OCH₃)— | VIII | COCH₃ | CH₃ | CH | O |
| 7.94 | 2-(Ph)cyclopentyl | VIII | COCH₃ | CH₃ | CH | O |
| 7.95 | 2-(Ph)cyclohexyl | VIII | COCH₃ | CH₃ | CH | O |
| 7.96 | 2-(2'-(Ph)cyclopropyl)cyclopropyl | VIII | COCH₃ | CH₃ | CH | O |
| 7.97 | 2-(1'-(Ph)cyclopropyl)cyclopropyl | VIII | COCH₃ | CH₃ | CH | O |
| 7.98 | cyclopropyl | VIII | COPh | H | CH | O |
| 7.99 | 4-Cl(Ph) | VIII | COPh | H | CH | O |
| 7.100 | CH₃ | VIII | COPh | CH₃ | CH | O |
| 7.101 | PhCH₂ | VIII | COPh | CH₃ | CH | O |
| 7.102 | 2-Cl(Ph)CH₂ | VIII | COPh | CH₃ | CH | O |
| 7.103 | 4-Cl(Ph)CH₂ | VIII | COPh | CH₃ | CH | O |
| 7.104 | 4-CH₃(Ph)CH₂ | VIII | COPh | CH₃ | CH | O |
| 7.105 | 2-(PhCH₂)cyclopropyl | VIII | COPh | CH₃ | CH | O |
| 7.106 | 2-(2'-Cl(Ph)CH₂)cyclopropyl | VIII | COPh | CH₃ | CH | O |
| 7.107 | 2-(4'-Cl(Ph)CH₂)cyclopropyl | VIII | COPh | CH₃ | CH | O |
| 7.108 | 2-(2'-(PhCH₂)cyclopropyl)cyclopropyl | VIII | COPh(4-Cl) | CH₃ | CH | O |
| 7.109 | 2-(1'-(PhCH₂)cyclopropyl)cyclopropyl | VIII | COPh(4-Cl) | CH₃ | CH | O |
| 7.110 | 2-(2'-pyridyl)cyclopropyl | VIII | COPh(4-Cl) | CH₃ | CH | O |

Further typical compounds described by the present invention are described in the following tables.

Table VIII:
Compounds 8.01 to 8.110 are Compounds of Table VII of Formula VIII, IX, X where V=O and A is N.

Table IX:
Compounds 9.01 to 9.110 are Compounds of Table VII of Formula VIII, IX, X where V=NH and A is N.

Typical compounds encompassed by the present invention of Formula I (X=H) include those compounds presented in Table X of Formula XI, XII and XIII where one of $R_1$ or $R_2$ or $R_3$ or $R_4$ is not H, Z can be N—$R_5R_6$, or Z can be $OR_5$ if n=0 (and m=1), where R, $R_1$, $R_2$, $R_3$, $R_4$ and Z are defined in Table X.

TABLE X

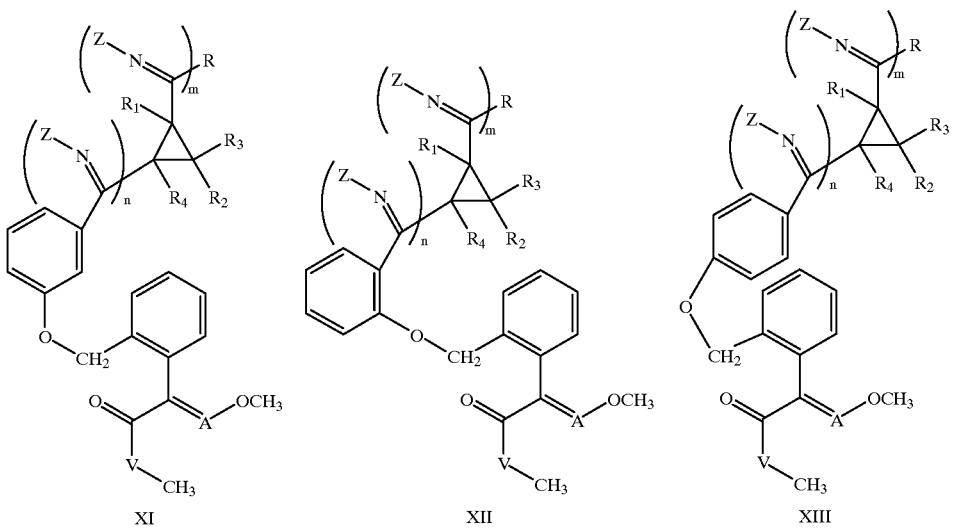

XI  XII  XIII

| Cmpd # | R | Formula | n | m | $R_1$ | $R_2$ | $R_3$ | $R_4$ | Z | A | V |
|---|---|---|---|---|---|---|---|---|---|---|---|
| 10.01 | Ph | XI | 0 | 1 | CN | H | H | H | N(CH$_3$)$_2$ | CH | O |
| 10.02 | Ph | XII | 0 | 1 | CN | H | H | H | N(CH$_3$)$_2$ | CH | O |
| 10.03 | Ph | XIII | 0 | 1 | CN | H | H | H | N(CH$_3$)$_2$ | CH | O |
| 10.04 | 4-Cl(Ph) | XI | 0 | 1 | CN | H | H | H | NHCOCH$_3$ | CH | O |
| 10.05 | 4-Cl(Ph) | XII | 0 | 1 | CN | H | H | H | NHCOCH$_3$ | CH | O |
| 10.06 | 4-Cl(Ph) | XIII | 0 | 1 | CN | H | H | H | NHCOCH$_3$ | CH | O |
| 10.07 | 2-F(Ph) | XI | 0 | 1 | CN | H | H | H | NHCOCH$_3$ | CH | O |
| 10.08 | 4-CH$_3$(Ph) | XI | 0 | 1 | CN | H | H | H | NHCOCH$_3$ | CH | O |
| 10.09 | 4-CH$_3$O(Ph) | XI | 0 | 1 | CN | H | H | H | NHCOCH$_3$ | CH | O |
| 10.10 | 2,4-Cl(Ph) | XI | 0 | 1 | CN | H | H | H | NHCOCH$_3$ | CH | O |
| 10.11 | CH$_3$ | XI | 0 | 1 | CN | H | H | H | OCH$_3$ | CH | O |
| 10.12 | CH$_3$CH$_2$ | XI | 0 | 1 | CN | H | H | H | OCH$_3$ | CH | O |
| 10.13 | cyclopropyl | XI | 0 | 1 | CN | H | H | H | OCH$_3$ | CH | O |
| 10.14 | pyridin-2-yl | XI | 0 | 1 | CN | H | H | H | OCH$_3$ | CH | O |
| 10.15 | 2-(Ph)cyclopropyl | XI | 0 | 1 | CN | H | H | H | OCH$_3$ | CH | O |
| 10.16 | Ph | XI | 0 | 1 | CO$_2$Et | H | H | H | N(CH$_3$)$_2$ | CH | O |
| 10.17 | Ph | XII | 0 | 1 | CO$_2$Et | H | H | H | N(CH$_3$)$_2$ | CH | O |
| 10.18 | Ph | XIII | 0 | 1 | CO$_2$Et | H | H | H | N(CH$_3$)$_2$ | CH | O |
| 10.19 | 4-Cl(Ph) | XI | 0 | 1 | CO$_2$Et | H | H | H | NHCOCH$_3$ | CH | O |
| 10.20 | 2-F(Ph) | XI | 0 | 1 | CO$_2$Et | H | H | H | NHCOCH$_3$ | CH | O |
| 10.21 | 4-CH$_3$(Ph) | XI | 0 | 1 | CO$_2$Et | H | H | H | NHCOCH$_3$ | CH | O |
| 10.22 | 4-CH$_3$O(Ph) | XI | 0 | 1 | CO$_2$Et | H | H | H | NHCOCH$_3$ | CH | O |
| 10.23 | 2,4-Cl(Ph) | XI | 0 | 1 | CO$_2$Et | H | H | H | NHCOCH$_3$ | CH | O |
| 10.24 | CH$_3$ | XI | 0 | 1 | CO$_2$Et | H | H | H | OCH$_3$ | CH | O |
| 10.25 | CH$_3$CH$_2$ | XI | 0 | 1 | CO$_2$Et | H | H | H | OCH$_3$ | CH | O |
| 10.26 | cyclopropyl | XI | 0 | 1 | CO$_2$Et | H | H | H | OCH$_3$ | CH | O |
| 10.27 | pyridin-2-yl | XI | 0 | 1 | CO$_2$Et | H | H | H | OCH$_3$ | CH | O |
| 10.28 | 2-(Ph)cyclopropyl | XI | 0 | 1 | CO$_2$Et | H | H | H | OCH$_3$ | CH | O |
| 10.29 | Ph | XI | 0 | 1 | H | CN | H | H | N(CH$_3$)$_2$ | CH | O |
| 10.30 | Ph | XII | 0 | 1 | H | CN | H | H | N(CH$_3$)$_2$ | CH | O |
| 10.31 | Ph | XIII | 0 | 1 | H | CN | H | H | N(CH$_3$)$_2$ | CH | O |
| 10.32 | 4-Cl(Ph) | XI | 0 | 1 | H | CN | H | H | NHCOCH$_3$ | CH | O |
| 10.33 | 4-Cl(Ph) | XII | 0 | 1 | H | CN | H | H | NHCOCH$_3$ | CH | O |
| 10.34 | 4-Cl(Ph) | XIII | 0 | 1 | H | CN | H | H | NHCOCH$_3$ | CH | O |
| 10.35 | 2-F(Ph) | XI | 0 | 1 | H | CN | H | H | NHCOCH$_3$ | CH | O |
| 10.36 | 4-CH$_3$(Ph) | XI | 0 | 1 | H | CN | H | H | NHCOCH$_3$ | CH | O |
| 10.37 | 4-CH$_3$O(Ph) | XI | 0 | 1 | H | CN | H | H | NHCOCH$_3$ | CH | O |
| 10.38 | 2,4-Cl(Ph) | XI | 0 | 1 | H | CN | H | H | NHCOCH$_3$ | CH | O |
| 10.39 | CH$_3$ | XI | 0 | 1 | H | CN | H | H | OCH$_3$ | CH | O |
| 10.40 | CH$_3$CH$_2$ | XI | 0 | 1 | H | CN | H | H | OCH$_3$ | CH | O |

TABLE X-continued

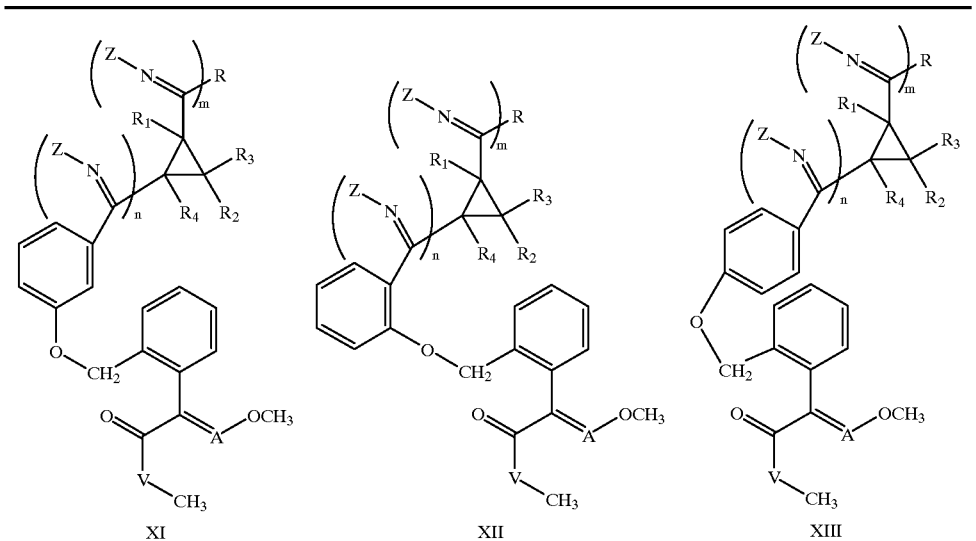

| Cmpd # | R | Formula | n | m | $R_1$ | $R_2$ | $R_3$ | $R_4$ | Z | A | V |
|---|---|---|---|---|---|---|---|---|---|---|---|
| 10.41 | cyclopropyl | XI | 0 | 1 | H | CN | H | H | $OCH_3$ | CH | O |
| 10.42 | pyridin-2-yl | XI | 0 | 1 | H | CN | H | H | $OCH_3$ | CH | O |
| 10.43 | 2-(Ph)cyclopropyl | XI | 0 | 1 | H | CN | H | H | $OCH_3$ | CH | O |
| 10.44 | Ph | XI | 0 | 1 | H | $CO_2Et$ | H | H | $N(CH_3)_2$ | CH | O |
| 10.45 | Ph | XII | 0 | 1 | H | $CO_2Et$ | H | H | $N(CH_3)_2$ | CH | O |
| 10.46 | Ph | XIII | 0 | 1 | H | $CO_2Et$ | H | H | $N(CH_3)_2$ | CH | O |
| 10.47 | 4-Cl(Ph) | XI | 0 | 1 | H | $CO_2Et$ | H | H | $NHCOCH_3$ | CH | O |
| 10.48 | 4-Cl(Ph) | XII | 0 | 1 | H | $CO_2Et$ | H | H | $NHCOCH_3$ | CH | O |
| 10.49 | 4-Cl(Ph) | XIII | 0 | 1 | H | $CO_2Et$ | H | H | $NHCOCH_3$ | CH | O |
| 10.50 | 2-F(Ph) | XI | 0 | 1 | H | $CO_2Et$ | H | H | $NHCOCH_3$ | CH | O |
| 10.51 | 4-$CH_3$(Ph) | XI | 0 | 1 | H | $CO_2Et$ | H | H | $NHCOCH_3$ | CH | O |
| 10.52 | 4-$CH_3O$(Ph) | XI | 0 | 1 | H | $CO_2Et$ | H | H | $NHCOCH_3$ | CH | O |
| 10.53 | 2,4-Cl(Ph) | XI | 0 | 1 | H | $CO_2Et$ | H | H | $NHCOCH_3$ | CH | O |
| 10.54 | $CH_3$ | XI | 0 | 1 | H | $CO_2Et$ | H | H | $OCH_3$ | CH | O |
| 10.55 | $CH_3CH_2$ | XI | 0 | 1 | H | $CO_2Et$ | H | H | $OCH_3$ | CH | O |
| 10.56 | cyclopropyl | XI | 0 | 1 | H | $CO_2Et$ | H | H | $OCH_3$ | CH | O |
| 10.57 | pyridin-2-yl | XI | 0 | 1 | H | $CO_2Et$ | H | H | $OCH_3$ | CH | O |
| 10.58 | 2-(Ph)cyclopropyl | XI | 0 | 1 | H | $CO_2Et$ | H | H | $OCH_3$ | CH | O |
| 10.59 | Ph | XI | 0 | 1 | H | H | H | CN | $N(CH_3)_2$ | CH | O |
| 10.60 | Ph | XII | 0 | 1 | H | H | H | CN | $N(CH_3)_2$ | CH | O |
| 10.61 | Ph | XIII | 0 | 1 | H | H | H | CN | $N(CH_3)_2$ | CH | O |
| 10.62 | 4-Cl(Ph) | XI | 0 | 1 | H | H | H | CN | $NHCOCH_3$ | CH | O |
| 10.63 | 4-Cl(Ph) | XI | 0 | 1 | H | H | H | CN | $NHCOCH_3$ | CH | O |
| 10.64 | 4-Cl(Ph) | XI | 0 | 1 | H | H | H | CN | $NHCOCH_3$ | CH | O |
| 10.65 | 2-F(Ph) | XI | 0 | 1 | H | H | H | CN | $NHCOCH_3$ | CH | O |
| 10.66 | 4-$CH_3$(Ph) | XI | 0 | 1 | H | H | H | CN | $NHCOCH_3$ | CH | O |
| 10.67 | 4-$CH_3O$(Ph) | XI | 0 | 1 | H | H | H | CN | $NHCOCH_3$ | CH | O |
| 10.68 | 2,4-Cl(Ph) | XI | 0 | 1 | H | H | H | CN | $NHCOCH_3$ | CH | O |
| 10.69 | $CH_3$ | XII | 0 | 1 | H | H | H | CN | $OCH_3$ | CH | O |
| 10.70 | $CH_3CH_2$ | XIII | 0 | 1 | H | H | H | CN | $OCH_3$ | CH | O |
| 10.71 | cyclopropyl | XI | 0 | 1 | H | H | H | CN | $OCH_3$ | CH | O |
| 10.72 | pyridin-2-yl | XII | 0 | 1 | H | H | H | CN | $OCH_3$ | CH | O |
| 10.73 | 2-(Ph)cyclopropyl | XIII | 0 | 1 | H | H | H | CN | $OCH_3$ | CH | O |
| 10.74 | Ph | XI | 0 | 1 | H | H | H | $CO_2Et$ | $N(CH_3)_2$ | CH | O |
| 10.75 | Ph | XII | 0 | 1 | H | H | H | $CO_2Et$ | $N(CH_3)_2$ | CH | O |
| 10.76 | Ph | XIII | 0 | 1 | H | H | H | $CO_2Et$ | $N(CH_3)_2$ | CH | O |
| 10.77 | 4-Cl(Ph) | XI | 0 | 1 | H | H | H | $CO_2Et$ | $NHCOCH_3$ | CH | O |
| 10.78 | 2-F(Ph) | XI | 0 | 1 | H | H | H | $CO_2Et$ | $NHCOCH_3$ | CH | O |
| 10.79 | 4-$CH_3$(Ph) | XI | 0 | 1 | H | H | H | $CO_2Et$ | $NHCOCH_3$ | CH | O |
| 10.80 | 4-$CH_3O$(Ph) | XI | 0 | 1 | H | H | H | $CO_2Et$ | $NHCOCH_3$ | CH | O |
| 10.81 | 2,4-Cl(Ph) | XI | 0 | 1 | H | H | H | $CO_2Et$ | $NHCOCH_3$ | CH | O |
| 10.82 | $CH_3$ | XI | 0 | 1 | H | H | H | $CO_2Et$ | $OCH_3$ | CH | O |
| 10.83 | $CH_3CH_2$ | XI | 0 | 1 | H | H | H | $CO_2Et$ | $OCH_3$ | CH | O |
| 10.84 | cyclopropyl | XI | 0 | 1 | H | H | H | $CO_2Et$ | $OCH_3$ | CH | O |
| 10.85 | pyridin-2-yl | XI | 0 | 1 | H | H | H | $CO_2Et$ | $OCH_3$ | CH | O |
| 10.86 | 2-(Ph)cyclopropyl | XI | 0 | 1 | H | H | H | $CO_2Et$ | $OCH_3$ | CH | O |
| 10.87 | Ph | XI | 0 | 1 | H | —$CH_2CH_2$— | | H | $N(CH_3)_2$ | CH | O |
| 10.88 | Ph | XII | 0 | 1 | H | —$CH_2CH_2$— | | H | $N(CH_3)_2$ | CH | O |
| 10.89 | Ph | XIII | 0 | 1 | H | —$CH_2CH_2$— | | H | $N(CH_3)_2$ | CH | O |
| 10.90 | 4-Cl(Ph) | XI | 0 | 1 | H | —$CH_2CH_2$— | | H | $NHCOCH_3$ | CH | O |
| 10.91 | 2-F(Ph) | XI | 0 | 1 | H | —$CH_2CH_2$— | | H | $NHCOCH_3$ | CH | O |

TABLE X-continued

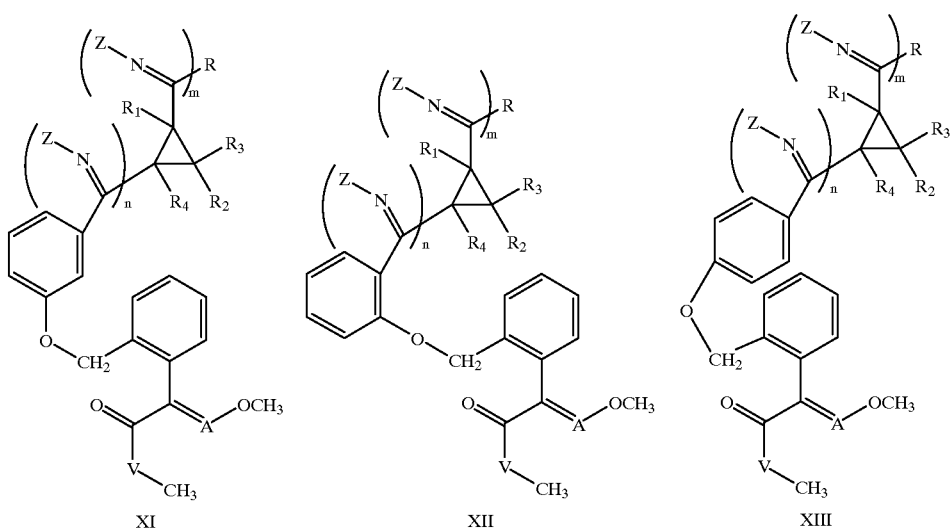

XI  XII  XIII

| Cmpd # | R | Formula | n | m | R₁ | R₂ | R₃ | R₄ | Z | A | V |
|---|---|---|---|---|---|---|---|---|---|---|---|
| 10.92 | 4-CH₃(Ph) | XI | 0 | 1 | H | —CH₂CH₂— | | H | NHCOCH₃ | CH | O |
| 10.93 | 4-CH₃O(Ph) | XI | 0 | 1 | H | —CH₂CH₂— | | H | NHCOCH₃ | CH | O |
| 10.94 | 2,4-Cl(Ph) | XI | 0 | 1 | H | —CH₂CH₂— | | H | NHCOCH₃ | CH | O |
| 10.95 | CH₃ | XI | 0 | 1 | H | —CH₂CH₂— | | H | OCH₃ | CH | O |
| 10.96 | CH₃CH₂ | XI | 0 | 1 | H | —CH₂CH₂— | | H | OCH₃ | CH | O |
| 10.97 | cyclopropyl | XI | 0 | 1 | H | —CH₂CH₂— | | H | OCH₃ | CH | O |
| 10.98 | (CH₃)₃C | XI | 0 | 1 | H | —CH₂CH₂— | | H | OCH₃ | CH | O |
| 10.99 | pyridin-2-yl | XI | 0 | 1 | H | —CH₂CH₂— | | H | OCH₃ | CH | O |
| 10.100 | 2-(Ph)cyclopropyl | XI | 0 | 1 | H | —CH₂CH₂— | | H | OCH₃ | CH | O |
| 10.101 | CH₃CH₂CH₂ | XI | 0 | 1 | H | —CH₂CH₂— | | H | OCH₃ | CH | O |
| 10.102 | (CH₃)₂CH | XI | 0 | 1 | H | —CH₂CH₂— | | H | OCH₃ | CH | O |
| 10.103 | CH₃(CH₂)2CH₂ | XI | 0 | 1 | H | —CH₂CH₂— | | H | OCH₃ | CH | O |
| 10.104 | CH₃(CH₂)4CH₂ | XI | 0 | 1 | H | —CH₂CH₂— | | H | OCH₃ | CH | O |
| 10.105 | (CH₃)₂CHCH₂ | XI | 0 | 1 | H | —CH₂CH₂— | | H | OCH₃ | CH | O |
| 10.106 | pyridin-3-yl | XI | 0 | 1 | H | —CH₂CH₂— | | H | OCH₃ | CH | O |
| 10.107 | pyrimidin-2-yl | XI | 0 | 1 | H | —CH₂CH₂— | | H | OCH₃ | CH | O |
| 10.108 | thien-2-yl | XI | 0 | 1 | H | —CH₂CH₂— | | H | OCH₃ | CH | O |
| 10.109 | thien-3-yl | XI | 0 | 1 | H | —CH₂CH₂— | | H | OCH₃ | CH | O |
| 10.110 | 2-napthyl | XI | 0 | 1 | H | —CH₂CH₂— | | H | OCH₃ | CH | O |
| 10.111 | 2-furyl | XI | 0 | 1 | H | —CH₂CH₂— | | H | OCH₃ | CH | O |
| 10.112 | 3-furyl | XI | 0 | 1 | H | —CH₂CH₂— | | H | OCH₃ | CH | O |
| 10.113 | 2-methylcyclopropyl | XI | 0 | 1 | H | —CH₂CH₂— | | H | OCH₃ | CH | O |
| 10.114 | 2-ethylcyclopropyl | XI | 0 | 1 | H | —CH₂CH₂— | | H | OCH₃ | CH | O |
| 10.115 | 2-(n-propyl)cyclopropyl | XI | 0 | 1 | H | —CH₂CH₂— | | H | OCH₃ | CH | O |
| 10.116 | Ph | XI | 1 | 0 | CN | H | H | H | N(CH₃)₂ | CH | O |
| 10.117 | Ph | XII | 1 | 0 | CN | H | H | H | N(CH₃)₂ | CH | O |
| 10.118 | Ph | XIII | 1 | 0 | CN | H | H | H | N(CH₃)₂ | CH | O |
| 10.119 | 4-Cl(Ph) | XI | 1 | 0 | CN | H | H | H | N(CH₃)₂ | CH | O |
| 10.120 | 2-F(Ph) | XI | 1 | 0 | CN | H | H | H | N(CH₃)₂ | CH | O |
| 10.121 | 4-CH₃(Ph) | XI | 1 | 0 | CN | H | H | H | N(CH₃)₂ | CH | O |
| 10.122 | 4-CH₃O(Ph) | XI | 1 | 0 | CN | H | H | H | N(CH₃)₂ | CH | O |
| 10.123 | 2,4-Cl(Ph) | XI | 1 | 0 | CN | H | H | H | N(CH₃)₂ | CH | O |
| 10.124 | CH₃ | XI | 1 | 0 | CN | H | H | H | NHCOCH₃ | CH | O |
| 10.125 | CH₃CH₂ | XI | 1 | 0 | CN | H | H | H | NHCOCH₃ | CH | O |
| 10.126 | cyclopropyl | XI | 1 | 0 | CN | H | H | H | NHCOCH₃ | CH | O |
| 10.127 | (CH₃)₃C | XI | 1 | 0 | CN | H | H | H | NHCOCH₃ | CH | O |
| 10.128 | pyridin-2-yl | XI | 1 | 0 | CN | H | H | H | NHCOCH₃ | CH | O |
| 10.129 | 2-(Ph)cyclopropyl | XI | 1 | 0 | CN | H | H | H | NHCOCH₃ | CH | O |
| 10.130 | Ph | XI | 1 | 0 | CO₂Et | H | H | H | N(CH₃)₂ | CH | O |
| 10.131 | Ph | XII | 1 | 0 | CO₂Et | H | H | H | N(CH₃)₂ | CH | O |
| 10.132 | Ph | XIII | 1 | 0 | CO₂Et | H | H | H | N(CH₃)₂ | CH | O |
| 10.133 | 4-Cl(Ph) | XI | 1 | 0 | CO₂Et | H | H | H | N(CH₃)₂ | CH | O |
| 10.134 | 2-F(Ph) | XI | 1 | 0 | CO₂Et | H | H | H | N(CH₃)₂ | CH | O |
| 10.135 | 4-CH₃(Ph) | XI | 1 | 0 | CO₂Et | H | H | H | N(CH₃)₂ | CH | O |
| 10.136 | 4-CH₃O(Ph) | XI | 1 | 0 | CO₂Et | H | H | H | N(CH₃)₂ | CH | O |
| 10.137 | 2,4-Cl(Ph) | XI | 1 | 0 | CO₂Et | H | H | H | N(CH₃)₂ | CH | O |
| 10.138 | CH₃ | XI | 1 | 0 | CO₂Et | H | H | H | NHCOCH₃ | CH | O |
| 10.139 | CH₃CH₂ | XI | 1 | 0 | CO₂Et | H | H | H | NHCOCH₃ | CH | O |
| 10.140 | cyclopropyl | XI | 1 | 0 | CO₂Et | H | H | H | NHCOCH₃ | CH | O |
| 10.141 | (CH₃)₃C | XI | 1 | 0 | CO₂Et | H | H | H | NHCOCH₃ | CH | O |
| 10.142 | pyridin-2-yl | XI | 1 | 0 | CO₂Et | H | H | H | NHCOCH₃ | CH | O |

TABLE X-continued

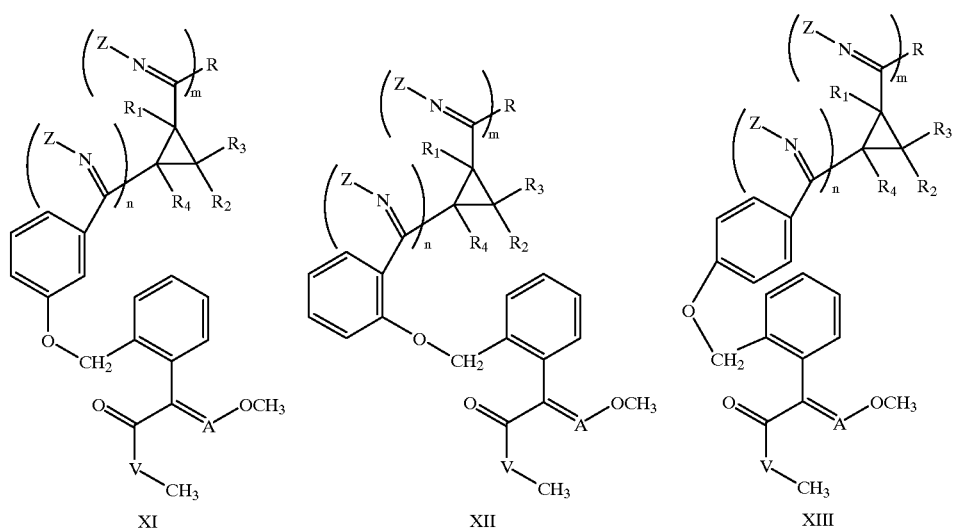

| Cmpd # | R | Formula | n | m | R₁ | R₂ | R₃ | R₄ | Z | A | V |
|---|---|---|---|---|---|---|---|---|---|---|---|
| 10.143 | 2-(Ph)cyclopropyl | XI | 1 | 0 | CO₂Et | H | H | H | NHCOCH₃ | CH | O |
| 10.144 | Ph | XI | 1 | 0 | H | CN | H | H | N(CH₃)₂ | CH | O |
| 10.145 | Ph | XII | 1 | 0 | H | CN | H | H | N(CH₃)₂ | CH | O |
| 10.146 | Ph | XIII | 1 | 0 | H | CN | H | H | N(CH₃)₂ | CH | O |
| 10.147 | 4-Cl(Ph) | XI | 1 | 0 | H | CN | H | H | N(CH₃)₂ | CH | O |
| 10.148 | 2-F(Ph) | XI | 1 | 0 | H | CN | H | H | N(CH₃)₂ | CH | O |
| 10.149 | 4-CH₃(Ph) | XI | 1 | 0 | H | CN | H | H | N(CH₃)₂ | CH | O |
| 10.150 | 4-CH₃O(Ph) | XI | 1 | 0 | H | CN | H | H | N(CH₃)₂ | CH | O |
| 10.151 | 2,4-Cl(Ph) | XI | 1 | 0 | H | CN | H | H | N(CH₃)₂ | CH | O |
| 10.152 | CH₃ | XI | 1 | 0 | H | CN | H | H | NHCOCH₃ | CH | O |
| 10.153 | CH₃CH₂ | XI | 1 | 0 | H | CN | H | H | NHCOCH₃ | CH | O |
| 10.154 | cyclopropyl | XI | 1 | 0 | H | CN | H | H | NHCOCH₃ | CH | O |
| 10.155 | (CH₃)₃C | XI | 1 | 0 | H | CN | H | H | NHCOCH₃ | CH | O |
| 10.156 | pyridin-2-yl | XI | 1 | 0 | H | CN | H | H | NHCOCH₃ | CH | O |
| 10.157 | 2-(Ph)cyclopropyl | XI | 1 | 0 | H | CN | H | H | NHCOCH₃ | CH | O |
| 10.158 | Ph | XI | 1 | 0 | H | CO₂Et | H | H | N(CH₃)₂ | CH | O |
| 10.159 | Ph | XII | 1 | 0 | H | CO₂Et | H | H | N(CH₃)₂ | CH | O |
| 10.160 | Ph | XIII | 1 | 0 | H | CO₂Et | H | H | N(CH₃)₂ | CH | O |
| 10.161 | 4-Cl(Ph) | XI | 1 | 0 | H | CO₂Et | H | H | N(CH₃)₂ | CH | O |
| 10.162 | 2-F(Ph) | XI | 1 | 0 | H | CO₂Et | H | H | N(CH₃)₂ | CH | O |
| 10.163 | 4-CH₃(Ph) | XI | 1 | 0 | H | CO₂Et | H | H | N(CH₃)₂ | CH | O |
| 10.164 | 4-CH₃O(Ph) | XI | 1 | 0 | H | CO₂Et | H | H | N(CH₃)₂ | CH | O |
| 10.165 | 2,4-Cl(Ph) | XI | 1 | 0 | H | CO₂Et | H | H | N(CH₃)₂ | CH | O |
| 10.166 | CH₃ | XI | 1 | 0 | H | CO₂Et | H | H | NHCOCH₃ | CH | O |
| 10.167 | CH₃CH₂ | XI | 1 | 0 | H | CO₂Et | H | H | NHCOCH₃ | CH | O |
| 10.168 | cyclopropyl | XI | 1 | 0 | H | CO₂Et | H | H | NHCOCH₃ | CH | O |
| 10.169 | (CH₃)₃C | XI | 1 | 0 | H | CO₂Et | H | H | NHCOCH₃ | CH | O |
| 10.170 | pyridin-2-yl | XI | 1 | 0 | H | CO₂Et | H | H | NHCOCH₃ | CH | O |
| 10.171 | 2-(Ph)cyclopropyl | XI | 1 | 0 | H | CO₂Et | H | H | NHCOCH₃ | CH | O |
| 10.172 | Ph | XI | 1 | 0 | H | H | H | CN | N(CH₃)₂ | CH | O |
| 10.173 | Ph | XII | 1 | 0 | H | H | H | CN | N(CH₃)₂ | CH | O |
| 10.174 | Ph | XIII | 1 | 0 | H | H | H | CN | N(CH₃)₂ | CH | O |
| 10.175 | 4-Cl(Ph) | XI | 1 | 0 | H | H | H | CN | N(CH₃)₂ | CH | O |
| 10.176 | 2-F(Ph) | XI | 1 | 0 | H | H | H | CN | N(CH₃)₂ | CH | O |
| 10.177 | 4-CH₃(Ph) | XI | 1 | 0 | H | H | H | CN | N(CH₃)₂ | CH | O |
| 10.178 | 4-CH₃O(Ph) | XI | 1 | 0 | H | H | H | CN | N(CH₃)₂ | CH | O |
| 10.179 | 2,4-Cl(Ph) | XI | 1 | 0 | H | H | H | CN | N(CH₃)₂ | CH | O |
| 10.180 | CH₃ | XI | 1 | 0 | H | H | H | CN | NHCOCH₃ | CH | O |
| 10.181 | CH₃CH₂ | XI | 1 | 0 | H | H | H | CN | NHCOCH₃ | CH | O |
| 10.182 | cyclopropyl | XI | 1 | 0 | H | H | H | CN | NHCOCH₃ | CH | O |
| 10.183 | (CH₃)₃C | XI | 1 | 0 | H | H | H | CN | NHCOCH₃ | CH | O |
| 10.184 | pyridin-2-yl | XI | 1 | 0 | H | H | H | CN | NHCOCH₃ | CH | O |
| 10.185 | 2-(Ph)cyclopropyl | XI | 1 | 0 | H | H | H | CN | NHCOCH₃ | CH | O |
| 10.186 | Ph | XI | 1 | 0 | H | H | H | CO₂Et | N(CH₃)₂ | CH | O |
| 10.187 | Ph | XII | 1 | 0 | H | H | H | CO₂Et | N(CH₃)₂ | CH | O |
| 10.188 | Ph | XIII | 1 | 0 | H | H | H | CO₂Et | N(CH₃)₂ | CH | O |
| 10.189 | 4-Cl(Ph) | XI | 1 | 0 | H | H | H | CO₂Et | N(CH₃)₂ | CH | O |
| 10.190 | 2-F(Ph) | XI | 1 | 0 | H | H | H | CO₂Et | N(CH₃)₂ | CH | O |
| 10.191 | 4-CH₃(Ph) | XI | 1 | 0 | H | H | H | CO₂Et | N(CH₃)₂ | CH | O |
| 10.192 | 4-CH₃O(Ph) | XI | 1 | 0 | H | H | H | CO₂Et | N(CH₃)₂ | CH | O |
| 10.193 | 2,4-Cl(Ph) | XI | 1 | 0 | H | H | H | CO₂Et | N(CH₃)₂ | CH | O |

TABLE X-continued

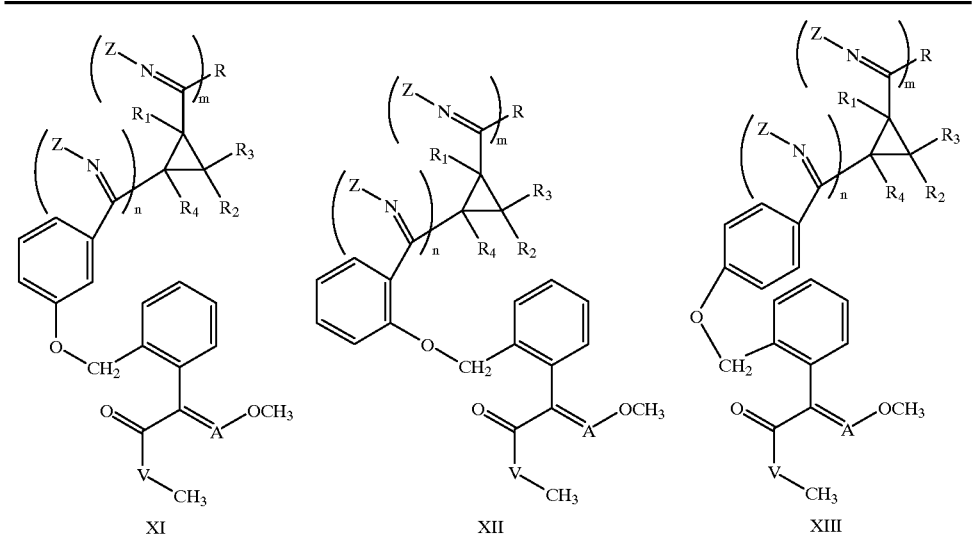

XI    XII    XIII

| Cmpd # | R | Formula | n | m | $R_1$ | $R_2$ | $R_3$ | $R_4$ | Z | A | V |
|---|---|---|---|---|---|---|---|---|---|---|---|
| 10.194 | $CH_3$ | XI | 1 | 0 | H | H | H | $CO_2Et$ | $NHCOCH_3$ | CH | O |
| 10.195 | $CH_3CH_2$ | XI | 1 | 0 | H | H | H | $CO_2Et$ | $NHCOCH_3$ | CH | O |
| 10.196 | cyclopropyl | XI | 1 | 0 | H | H | H | $CO_2Et$ | $NHCOCH_3$ | CH | O |
| 10.197 | $(CH_3)_3C$ | XI | 1 | 0 | H | H | H | $CO_2Et$ | $NHCOCH_3$ | CH | O |
| 10.198 | pyridin-2-yl | XI | 1 | 0 | H | H | H | $CO_2Et$ | $NHCOCH_3$ | CH | O |
| 10.199 | 2-(Ph)cyclopropyl | XI | 1 | 0 | H | H | H | $CO_2Et$ | $NHCOCH_3$ | CH | O |
| 10.200 | Ph | XI | 1 | 0 | H | —$CH_2CH_2$— | | H | $N(CH_3)_2$ | CH | O |
| 10.201 | Ph | XII | 1 | 0 | H | —$CH_2CH_2$— | | H | $N(CH_3)_2$ | CH | O |
| 10.202 | Ph | XIII | 1 | 0 | H | —$CH_2CH_2$— | | H | $N(CH_3)_2$ | CH | O |
| 10.203 | 4-Cl(Ph) | XI | 1 | 0 | H | —$CH_2CH_2$— | | H | $N(CH_3)_2$ | CH | O |
| 10.204 | 2-F(Ph) | XI | 1 | 0 | H | —$CH_2CH_2$— | | H | $N(CH_3)_2$ | CH | O |
| 10.205 | 4-$CH_3$(Ph) | XI | 1 | 0 | H | —$CH_2CH_2$— | | H | $N(CH_3)_2$ | CH | O |
| 10.206 | 4-$CH_3O$(Ph) | XI | 1 | 0 | H | —$CH_2CH_2$— | | H | $N(CH_3)_2$ | CH | O |
| 10.207 | 2,4-Cl(Ph) | XI | 1 | 0 | H | —$CH_2CH_2$— | | H | $N(CH_3)_2$ | CH | O |
| 10.208 | $CH_3$ | XI | 1 | 0 | H | —$CH_2CH_2$— | | H | $NHCOCH_3$ | CH | O |
| 10.209 | $CH_3CH_2$ | XI | 1 | 0 | H | —$CH_2CH_2$— | | H | $NHCOCH_3$ | CH | O |
| 10.210 | cyclopropyl | XI | 1 | 0 | H | —$CH_2CH_2$— | | H | $NHCOCH_3$ | CH | O |
| 10.211 | $(CH_3)_3C$ | XI | 1 | 0 | H | —$CH_2CH_2$— | | H | $NHCOCH_3$ | CH | O |
| 10.212 | pyridin-2-yl | XI | 1 | 0 | H | —$CH_2CH_2$— | | H | $NHCOCH_3$ | CH | O |
| 10.213 | 2-(Ph)cyclopropyl | XI | 1 | 0 | H | —$CH_2CH_2$— | | H | $NHCOCH_3$ | CH | O |
| 10.214 | $CH_3CH_2CH_2$ | XI | 1 | 0 | H | —$CH_2CH_2$— | | H | $NHCOCH_3$ | CH | O |
| 10.215 | $(CH_3)_2CH$ | XI | 1 | 0 | H | —$CH_2CH_2$— | | H | $NHCOCH_3$ | CH | O |
| 10.216 | $CH_3(CH_2)2CH_2$ | XI | 1 | 0 | H | —$CH_2CH_2$— | | H | $NHCOCH_3$ | CH | O |
| 10.217 | $CH_3(CH_2)4CH_2$ | XI | 1 | 0 | H | —$CH_2CH_2$— | | H | $NHCOCH_3$ | CH | O |
| 10.218 | $(CH_3)_2CHCH_2$ | XI | 1 | 0 | H | —$CH_2CH_2$— | | H | $NHCOCH_3$ | CH | O |
| 10.219 | pyridin-3-yl | XI | 1 | 0 | H | —$CH_2CH_2$— | | H | $NHCOCH_3$ | CH | O |
| 10.220 | pyrimidin-2-yl | XI | 1 | 0 | H | —$CH_2CH_2$— | | H | $NHCOCH_3$ | CH | O |
| 10.221 | thien-2-yl | XI | 1 | 0 | H | —$CH_2CH_2$— | | H | $NHCOCH_3$ | CH | O |
| 10.222 | thien-3-yl | XI | 1 | 0 | H | —$CH_2CH_2$— | | H | $NHCOCH_3$ | CH | O |
| 10.223 | 2-napthyl | XI | 1 | 0 | H | —$CH_2CH_2$— | | H | $NHCOCH_3$ | CH | O |
| 10.224 | 2-furyl | XI | 1 | 0 | H | —$CH_2CH_2$— | | H | $NHCOCH_3$ | CH | O |
| 10.225 | 3-furyl | XI | 1 | 0 | H | —$CH_2CH_2$— | | H | $NHCOCH_3$ | CH | O |
| 10.226 | 2-methylcyclopropyl | XI | 1 | 0 | H | —$CH_2CH_2$— | | H | $NHCOCH_3$ | CH | O |
| 10.227 | 2-ethylcyclopropyl | XI | 1 | 0 | H | —$CH_2CH_2$— | | H | $NHCOCH_3$ | CH | O |
| 10.228 | 2-(n-propyl)cyclopropyl | XI | 1 | 0 | H | —$CH_2CH_2$— | | H | $NHCOCH_3$ | CH | O |

Further typical compounds described by the present invention are described in the following tables.

Table XI:

Compounds 11.01 to 228 are Compounds of Table X of Formula XI, XII, XIII where V=O and A is N Table XII:

Compounds 12.01 to 228 are Compounds of Table X of Formula XI, XII, XIII where V=NH and A is N Typical compounds encompassed by the present invention of Formula I ($X=R_1=R_2=R_3=R_4=H$) include those compounds presented in Table XIII of Formula XIV, XV and XVI (Z is $N=C(R_7R_8R_9)$, n or m=1 and n+m=1) where R, $R_7$, $R_8$, and $R_9$ are defined in Table XIII.

TABLE XIII

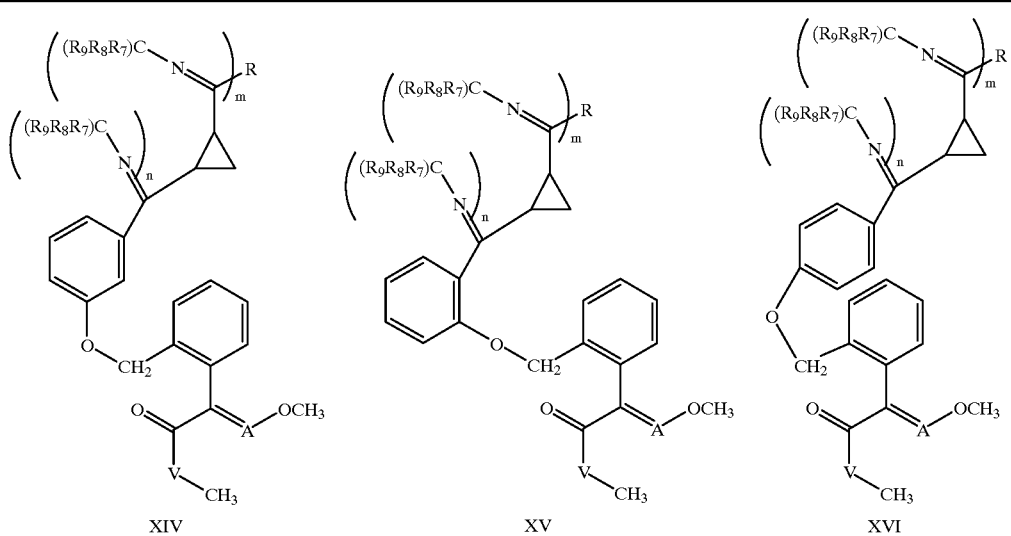

XIV　　　　　　　XV　　　　　　　XVI

| Cmpd # | R | Formula | n | m | $R_7$ | $R_8$ | $R_9$ | A | V |
|---|---|---|---|---|---|---|---|---|---|
| 13.01 | Ph | XIV | 0 | 1 | H | H | H | CH | O |
| 13.02 | Ph | XV | 0 | 1 | H | H | H | CH | O |
| 13.03 | Ph | XVI | 0 | 1 | H | H | H | CH | O |
| 13.04 | 4-Cl(Ph) | XIV | 0 | 1 | $CH_3$ | H | H | CH | O |
| 13.05 | 4-Cl(Ph) | XV | 0 | 1 | $CH_3$ | H | H | CH | O |
| 13.06 | 4-Cl(Ph) | XVI | 0 | 1 | $CH_3$ | H | H | CH | O |
| 13.07 | 2-Cl(Ph) | XIV | 0 | 1 | $CH_3$ | H | H | CH | O |
| 13.08 | 3-Cl(Ph) | XIV | 0 | 1 | $CH_3$ | H | H | CH | O |
| 13.09 | 2-F(Ph) | XIV | 0 | 1 | $CH_3$ | H | H | CH | O |
| 13.10 | 3-FPh) | XIV | 0 | 1 | $CH_3$ | H | H | CH | O |
| 13.11 | 4-FPh) | XIV | 0 | 1 | $CH_3$ | H | H | CH | O |
| 13.12 | $4-CH_3$(Ph) | XIV | 0 | 1 | $CH_3$ | H | H | CH | O |
| 13.13 | $4-CH_3O$(Ph) | XIV | 0 | 1 | $CH_3$ | H | H | CH | O |
| 13.14 | 2,4-Cl(Ph) | XIV | 0 | 1 | $CH_3$ | H | H | CH | O |
| 13.15 | 3,5-Cl(Ph) | XIV | 0 | 1 | $CH_3$ | H | H | CH | O |
| 13.16 | $CH_3$ | XIV | 0 | 1 | $CH_3$ | $CH_3$ | H | CH | O |
| 13.17 | $CH_3CH_2$ | XIV | 0 | 1 | $CH_3$ | $CH_3$ | H | CH | O |
| 13.18 | $CH_3CH_2CH_2$ | XIV | 0 | 1 | $CH_3$ | $CH_3$ | H | CH | O |
| 13.19 | $(CH_3)_2CH$ | XIV | 0 | 1 | $CH_3$ | $CH_3$ | H | CH | O |
| 13.20 | $CH_3(CH_2)_2CH_2$ | XIV | 0 | 1 | $CH_3$ | $CH_3$ | H | CH | O |
| 13.21 | $(CH_3)_2CHCH_2$ | XIV | 0 | 1 | $CH_3$ | $CH_3$ | H | CH | O |
| 13.22 | $CH_3CH_2(CH_3)CH$ | XIV | 0 | 1 | $CH_3$ | $CH_3$ | H | CH | O |
| 13.23 | $(CH_3)_3C$ | XIV | 0 | 1 | $CH_3$ | $CH_3$ | H | CH | O |
| 13.24 | $CH_3(CH_2)_3CH_2$ | XIV | 0 | 1 | $CH_3$ | $CH_3$ | H | CH | O |
| 13.25 | $CH_3CH_2CH_2(CH_3)CH$ | XIV | 0 | 1 | $CH_3$ | $CH_3$ | H | CH | O |
| 13.26 | $(CH_3)_2CHCH_2CH_2$ | XIV | 0 | 1 | $CH_3$ | $CH_3$ | H | CH | O |
| 13.27 | $CH_3CH_2(CH_3)_2C$ | XIV | 0 | 1 | $CH_3$ | $CH_3$ | H | CH | O |
| 13.28 | $CH_3(CH_2)_4CH_2$ | XIV | 0 | 1 | $CH_3$ | $CH_3$ | H | CH | O |
| 13.29 | $(CH_3)_2CH(CH_2)_2CH_2$ | XIV | 0 | 1 | $CH_3$ | $CH_3$ | H | CH | O |
| 13.30 | $CH_2=CHCH_2CH_2$ | XIV | 0 | 1 | $CH_3$ | $CH_3$ | H | CH | O |
| 13.31 | $CH_2=C(CH_3)CH_2CH_2$ | XIV | 0 | 1 | $CH_3$ | $CH_3$ | $CH_3$ | CH | O |
| 13.32 | $CF_3CH_2$ | XIV | 0 | 1 | $CH_3$ | $CH_3$ | $CH_3$ | CH | O |
| 13.33 | $CH_2=CH$ | XIV | 0 | 1 | $CH_3$ | $CH_3$ | $CH_3$ | CH | O |
| 13.34 | cyclopropyl | XIV | 0 | 1 | Ph | H | H | CH | O |
| 13.35 | cyclopentyl | XIV | 0 | 1 | Ph | H | H | CH | O |
| 13.36 | cyclohexyl | XIV | 0 | 1 | Ph | H | H | CH | O |
| 13.37 | $CH_2=C$(cyclopropyl) | XIV | 0 | 1 | Ph | H | H | CH | O |
| 13.38 | $CH_3—CH=C$(cyclopropyl) | XIV | 0 | 1 | Ph | H | H | CH | O |
| 13.39 | $CH_3O—CH=C$(cyclopropyl) | XIV | 0 | 1 | Ph | H | H | CH | O |
| 13.40 | $CH_3OCH_2$ | XIV | 0 | 1 | Ph | H | H | CH | O |
| 13.41 | $CH_3SCH(CH_3)$ | XIV | 0 | 1 | Ph | H | H | CH | O |
| 13.42 | $PhCH_2OCH_2$ | XIV | 0 | 1 | Ph | H | H | CH | O |
| 13.43 | $PhCH_2$ | XIV | 0 | 1 | Ph | H | H | CH | O |
| 13.44 | $2-Cl(Ph)CH_2$ | XIV | 0 | 1 | Ph | H | H | CH | O |
| 13.45 | $3-Cl(Ph)CH_2$ | XIV | 0 | 1 | Ph | H | H | CH | O |
| 13.46 | $4-Cl(Ph)CH_2$ | XIV | 0 | 1 | Ph | H | H | CH | O |
| 13.47 | $3-CH_3(Ph)CH_2$ | XIV | 0 | 1 | Ph | H | H | CH | O |
| 13.48 | $4-CH_3(Ph)CH_2$ | XIV | 0 | 1 | Ph | H | H | CH | O |
| 13.49 | pyridin-2-yl | XIV | 0 | 1 | Ph | H | H | CH | O |
| 13.50 | pyridin-3-yl | XIV | 0 | 1 | Ph | H | H | CH | O |
| 10.51 | pyridin-4-yl | XIV | 0 | 1 | Ph | H | H | CH | O |

TABLE XIII-continued

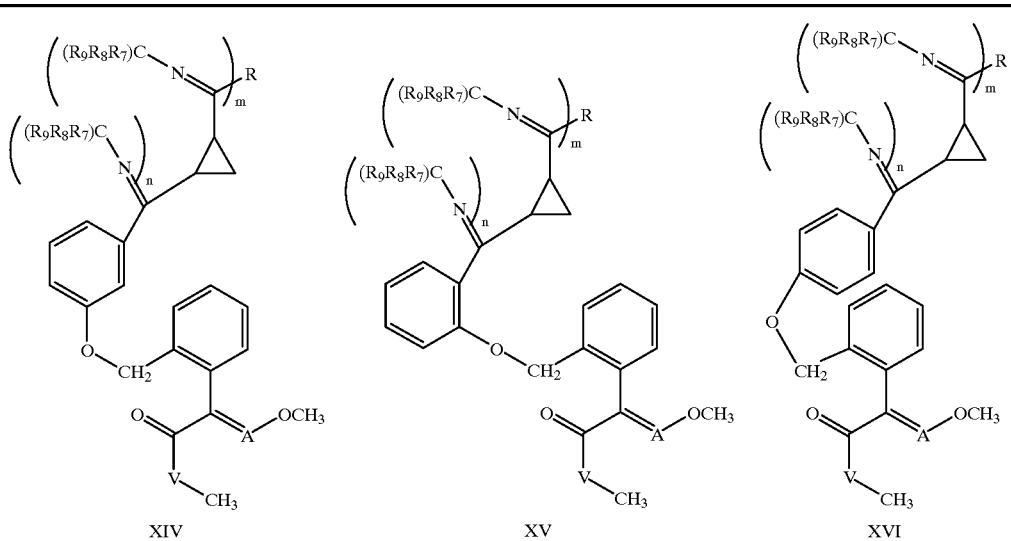

XIV  XV  XVI

| Cmpd # | R | Formula | n | m | R$_7$ | R$_8$ | R$_9$ | A | V |
|---|---|---|---|---|---|---|---|---|---|
| 13.52 | pyrimidin-2-yl | XIV | 0 | 1 | Ph | H | H | CH | O |
| 13.53 | pyrimidin-4-yl | XIV | 0 | 1 | Ph | H | H | CH | O |
| 13.54 | thien-2-yl | XIV | 0 | 1 | Ph | H | H | CH | O |
| 13.55 | thien-3-yl | XIV | 0 | 1 | Ph | H | H | CH | O |
| 13.56 | 1-napthyl | XIV | 0 | 1 | Ph | H | H | CH | O |
| 13.57 | 2-napthyl | XIV | 0 | 1 | Ph | H | H | CH | O |
| 13.58 | 2-furyl | XIV | 0 | 1 | Ph | H | H | CH | O |
| 13.59 | 3-furyl | XIV | 0 | 1 | Ph | H | H | CH | O |
| 13.60 | 2-(Ph)cyclopropyl | XIV | 0 | 1 | Ph | H | H | CH | O |
| 13.61 | 2-methylcyclopropyl | XIV | 0 | 1 | Ph | H | H | CH | O |
| 13.62 | 2-ethylcyclopropyl | XIV | 0 | 1 | Ph | H | H | CH | O |
| 13.63 | 2-(n-propyl)cyclopropyl | XIV | 0 | 1 | Ph | H | H | CH | O |
| 13.64 | 2-(n-butyl)cyclopropyl | XIV | 0 | 1 | Ph | H | H | CH | O |
| 13.65 | 2-(iso-butyl)cyclopropyl | XIV | 0 | 1 | CH$_3$ | H | H | CH | O |
| 13.66 | 2-(n-hexyl)cyclopropyl | XIV | 0 | 1 | CH$_3$ | H | H | CH | O |
| 13.67 | 2-methoxycyclopropyl | XIV | 0 | 1 | CH$_3$ | H | H | CH | O |
| 13.68 | 2-ethoxycyclopropyl | XIV | 0 | 1 | CH$_3$ | H | H | CH | O |
| 13.69 | 2-(n-propoxy)cyclopropyl | XIV | 0 | 1 | CH$_3$ | H | H | CH | O |
| 13.70 | 1-methylcyclopropyl | XIV | 0 | 1 | CH$_3$ | H | H | CH | O |
| 13.71 | 2-(CH=CH$_2$)cyclopropyl | XIV | 0 | 1 | CH$_3$ | H | H | CH | O |
| 13.72 | 2-(1-cyclopropyl)cyclopropyl | XIV | 0 | 1 | CH$_3$ | H | H | CH | O |
| 13.73 | 2-(2-cyclopropyl)cyclopropyl | XIV | 0 | 1 | CH$_3$ | H | H | CH | O |
| 13.74 | cyclopropyl-CH$_2$ | XIV | 0 | 1 | CH$_3$ | H | H | CH | O |
| 13.75 | cyclopropyl-CH=CH | XIV | 0 | 1 | CH$_3$ | H | H | CH | O |
| 13.76 | 1-(Ph)cyclopropyl | XIV | 0 | 1 | CH$_3$ | CH$_3$ | H | CH | O |
| 13.77 | 2-(Ph)cyclopropyl | XIV | 0 | 1 | CH$_3$ | CH$_3$ | H | CH | O |
| 13.78 | 1-(2'-Cl(Ph))cyclopropyl | XIV | 0 | 1 | CH$_3$ | CH$_3$ | H | CH | O |
| 13.79 | 2-(2'-Cl(Ph))cyclopropyl | XIV | 0 | 1 | CH$_3$ | CH$_3$ | H | CH | O |
| 13.80 | 1-(3'-Cl(Ph))cyclopropyl | XIV | 0 | 1 | CH$_3$ | CH$_3$ | H | CH | O |
| 13.81 | 2-(3'-Cl(Ph))cyclopropyl | XIV | 0 | 1 | CH$_3$ | CH$_3$ | H | CH | O |
| 13.82 | 1-(4'-Cl(Ph))cyclopropyl | XIV | 0 | 1 | CH$_3$ | CH$_3$ | H | CH | O |
| 13.83 | 2-(4'-Cl(Ph))cyclopropyl | XIV | 0 | 1 | CH$_3$ | CH$_3$ | H | CH | O |
| 13.84 | 1-(2'-F(Ph))cyclopropyl | XIV | 0 | 1 | CH$_3$ | CH$_3$ | H | CH | O |
| 13.85 | 2-(2'-F(Ph))cyclopropyl | XIV | 0 | 1 | CH$_3$ | CH$_3$ | H | CH | O |
| 13.86 | 2-(3'-F(Ph))cyclopropyl | XIV | 0 | 1 | CH$_3$ | CH$_3$ | H | CH | O |
| 13.87 | 2-(4'-F(Ph))cyclopropyl | XIV | 0 | 1 | CH$_3$ | CH$_3$ | H | CH | O |
| 13.88 | 2-(2'-Br(Ph))cyclopropyl | XIV | 0 | 1 | CH$_3$ | CH$_3$ | H | CH | O |
| 13.89 | 2-(3'-Br(Ph))cyclopropyl | XIV | 0 | 1 | CH$_3$ | CH$_3$ | H | CH | O |
| 13.90 | 2-(4'-Br(Ph))cyclopropyl | XIV | 0 | 1 | CH$_3$ | CH$_3$ | H | CH | O |
| 13.91 | 2-(2'-F(Ph))cyclopropyl | XIV | 0 | 1 | CH$_3$ | CH$_3$ | H | CH | O |
| 13.92 | 2-(2'-CH$_3$(Ph))cyclopropyl | XIV | 0 | 1 | CH$_3$ | CH$_3$ | H | CH | O |
| 13.93 | 2-(3'-CH$_3$(Ph))cyclopropyl | XIV | 0 | 1 | CH$_3$ | CH$_3$ | H | CH | O |
| 13.94 | 2-(4'-CH$_3$(Ph))cyclopropyl | XIV | 0 | 1 | CH$_3$ | CH$_3$ | H | CH | O |
| 13.95 | 2-(2'-CF$_3$((Ph)))cyclopropyl | XIV | 0 | 1 | CH$_3$ | CH$_3$ | H | CH | O |
| 13.96 | 2-(3'-CF$_3$(Ph))cyclopropyl | XIV | 0 | 1 | CH$_3$ | CH$_3$ | H | CH | O |
| 13.97 | 2-(4'-CF$_3$(Ph))cyclopropyl | XIV | 0 | 1 | CH$_3$ | CH$_3$ | H | CH | O |
| 13.98 | CH$_3$C(=N—OCH$_3$)— | XIV | 0 | 1 | CH$_3$ | CH$_3$ | H | CH | O |
| 13.99 | C$_2$H$_5$C(=N—OCH$_3$)— | XIV | 0 | 1 | CH$_3$ | CH$_3$ | H | CH | O |
| 13.100 | 2-(Ph)cyclopentyl | XIV | 0 | 1 | CH$_3$ | CH$_3$ | H | CH | O |
| 13.101 | 2-(Ph)cyclohexyl | XIV | 0 | 1 | CH$_3$ | CH$_3$ | H | CH | O |
| 13.102 | 2-(2'-(Ph)cyclopropyl)cyclopropyl | XIV | 0 | 1 | Ph | H | H | CH | O |

TABLE XIII-continued

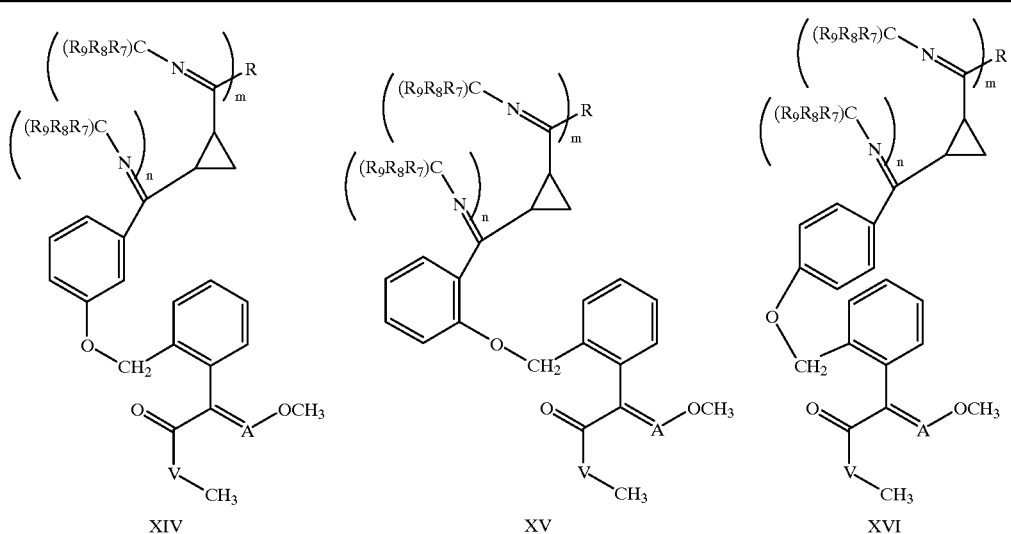

| Cmpd # | R | Formula | n | m | R7 | R8 | R9 | A | V |
|---|---|---|---|---|---|---|---|---|---|
| 13.103 | 2-(1'-(Ph)cyclopropyl)cyclopropyl | XIV | 0 | 1 | Ph | H | H | CH | O |
| 13.104 | 2-(PhCH$_2$)cyclopropyl | XIV | 0 | 1 | Ph | H | H | CH | O |
| 13.105 | 2-(2'-Cl(Ph)CH$_2$)cyclopropyl | XIV | 0 | 1 | Ph | H | H | CH | O |
| 13.106 | 2-(4'-Cl(Ph)CH$_2$)cyclopropyl | XIV | 0 | 1 | Ph | H | H | CH | O |
| 13.107 | 2-(2'-(PhCH$_2$)cyclopropyl)cyclopropyl | XIV | 0 | 1 | Ph | H | H | CH | O |
| 13.108 | 2-(1'-(PhCH$_2$)cyclopropyl)cyclopropyl | XIV | 0 | 1 | Ph | H | H | CH | O |
| 13.109 | 2-(2'-pyridyl)cyclopropyl | XIV | 0 | 1 | Ph | H | H | CH | O |
| 13.110 | 2-(3'-pyridyl)cyclopropyl | XIV | 0 | 1 | Ph | H | H | CH | O |
| 13.111 | 2-(2'-furyl)cyclopropyl | XIV | 0 | 1 | Ph | H | H | CH | O |
| 13.112 | 2-(3'-furyl)cyclopropyl | XIV | 0 | 1 | Ph | H | H | CH | O |
| 13.113 | 2-(2'-thienyl)cyclopropyl | XIV | 0 | 1 | Ph | H | H | CH | O |
| 13.114 | 2-(3'-thienyl)cyclopropyl | XIV | 0 | 1 | Ph | H | H | CH | O |
| 13.115 | Ph | XIV | 0 | 1 | CH$_3$ | H | H | CH | O |
| 13.116 | Ph | XV | 1 | 0 | CH$_3$ | H | H | CH | O |
| 13.117 | Ph | XVI | 1 | 0 | CH$_3$ | H | H | CH | O |
| 13.118 | 4-Cl(Ph) | XIV | 1 | 0 | CH$_3$ | H | H | CH | O |
| 13.119 | 4-Cl(Ph) | XV | 1 | 0 | CH$_3$ | H | H | CH | O |
| 13.120 | 4-Cl(Ph) | XIV | 1 | 0 | CH$_3$ | H | H | CH | O |
| 13.121 | 2-Cl(Ph) | XIV | 1 | 0 | CH$_3$ | H | H | CH | O |
| 13.122 | 3-Cl(Ph) | XIV | 1 | 0 | CH$_3$ | H | H | CH | O |
| 13.123 | 2-F(Ph) | XIV | 1 | 0 | CH$_3$ | H | H | CH | O |
| 13.124 | 3-FPh) | XIV | 1 | 0 | CH$_3$ | H | H | CH | O |
| 13.125 | 4-FPh) | XIV | 1 | 0 | CH$_3$ | H | H | CH | O |
| 13.126 | 4-CH$_3$(Ph) | XIV | 1 | 0 | CH$_3$ | H | H | CH | O |
| 13.127 | 4-CH$_3$O(Ph) | XIV | 1 | 0 | CH$_3$ | CH$_3$ | H | CH | O |
| 13.128 | 2,4-Cl(Ph) | XIV | 1 | 0 | CH$_3$ | CH$_3$ | H | CH | O |
| 13.129 | 3,5-Cl(Ph) | XIV | 1 | 0 | CH$_3$ | CH$_3$ | H | CH | O |
| 13.130 | CH$_3$ | XIV | 1 | 0 | CH$_3$ | CH$_3$ | H | CH | O |
| 13.131 | CH$_3$CH$_2$ | XIV | 1 | 0 | CH$_3$ | CH$_3$ | H | CH | O |
| 13.132 | CH$_3$CH$_2$CH$_2$ | XIV | 1 | 0 | CH$_3$ | CH$_3$ | H | CH | O |
| 13.133 | (CH$_3$)$_2$CH | XIV | 1 | 0 | CH$_3$ | CH$_3$ | H | CH | O |
| 13.134 | CH$_3$(CH$_2$)$_2$CH$_2$ | XIV | 1 | 0 | CH$_3$ | CH$_3$ | H | CH | O |
| 13.135 | (CH$_3$)$_2$CHCH$_2$ | XIV | 1 | 0 | CH$_3$ | CH$_3$ | H | CH | O |
| 13.136 | CH$_3$CH$_2$(CH$_3$)CH | XIV | 1 | 0 | CH$_3$ | CH$_3$ | H | CH | O |
| 13.137 | (CH$_3$)$_3$C | XIV | 1 | 0 | CH$_3$ | CH$_3$ | H | CH | O |
| 13.138 | CH$_3$(CH$_2$)$_3$CH$_2$ | XIV | 1 | 0 | CH$_3$ | CH$_3$ | H | CH | O |
| 13.139 | CH$_3$CH$_2$CH$_2$(CH$_3$)CH | XIV | 1 | 0 | CH$_3$ | CH$_3$ | H | CH | O |
| 13.140 | (CH$_3$)$_2$CHCH$_2$CH$_2$ | XIV | 1 | 0 | CH$_3$ | CH$_3$ | H | CH | O |
| 13.141 | CH$_3$CH$_2$(CH$_3$)$_2$C | XIV | 1 | 0 | CH$_3$ | CH$_3$ | H | CH | O |
| 13.142 | CH$_3$(CH$_2$)$_4$CH$_2$ | XIV | 1 | 0 | CH$_3$ | CH$_3$ | H | CH | O |
| 13.143 | (CH$_3$)$_2$CH(CH$_2$)$_2$CH$_2$ | XIV | 1 | 0 | CH$_3$ | CH$_3$ | H | CH | O |
| 13.144 | CH$_2$=CHCH$_2$CH$_2$ | XIV | 1 | 0 | CH$_3$ | CH$_3$ | CH$_3$ | CH | O |
| 13.145 | CH$_2$=C(CH$_3$)CH$_2$CH$_2$ | XIV | 1 | 0 | CH$_3$ | CH$_3$ | CH$_3$ | CH | O |
| 13.146 | CF$_3$CH$_2$ | XIV | 1 | 0 | CH$_3$ | CH$_3$ | CH$_3$ | CH | O |
| 13.147 | CH$_2$=CH | XIV | 1 | 0 | Ph | H | H | CH | O |
| 13.148 | cyclopropyl | XIV | 1 | 0 | Ph | H | H | CH | O |
| 13.149 | cyclopentyl | XIV | 1 | 0 | Ph | H | H | CH | O |
| 13.150 | cyclohexyl | XIV | 1 | 0 | Ph | H | H | CH | O |
| 13.151 | CH$_2$=C(cyclopropyl) | XIV | 1 | 0 | Ph | H | H | CH | O |
| 13.152 | CH$_3$—CH=C(cyclopropyl) | XIV | 1 | 0 | Ph | H | H | CH | O |
| 13.153 | CH$_3$O—CH=C(cyclopropyl) | XIV | 1 | 0 | Ph | H | H | CH | O |

TABLE XIII-continued

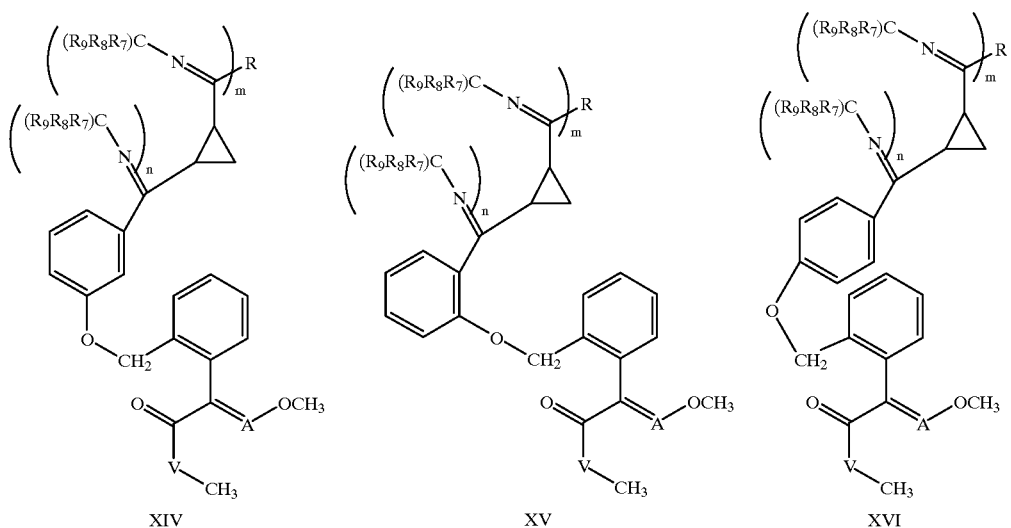

XIV        XV        XVI

| Cmpd # | R | Formula | n | m | $R_7$ | $R_8$ | $R_9$ | A | V |
|---|---|---|---|---|---|---|---|---|---|
| 13.154 | $CH_3OCH_2$ | XIV | 1 | 0 | Ph | H | H | CH | O |
| 13.155 | $CH_3SCH(CH_3)$ | XIV | 1 | 0 | Ph | H | H | CH | O |
| 13.156 | $PhCH_2OCH_2$ | XIV | 1 | 0 | Ph | H | H | CH | O |
| 13.157 | $PhCH_2$ | XIV | 1 | 0 | Ph | H | H | CH | O |
| 13.158 | 2-Cl(Ph)$CH_2$ | XIV | 1 | 0 | Ph | H | H | CH | O |
| 13.159 | 3-Cl(Ph)$CH_2$ | XIV | 1 | 0 | Ph | H | H | CH | O |
| 13.160 | 4-Cl(Ph)$CH_2$ | XIV | 1 | 0 | Ph | H | H | CH | O |
| 13.161 | 3-$CH_3$(Ph)$CH_2$ | XIV | 1 | 0 | Ph | H | H | CH | O |
| 13.162 | 4-$CH_3$(Ph)$CH_2$ | XIV | 1 | 0 | Ph | H | H | CH | O |
| 13.163 | pyridin-2-yl | XIV | 1 | 0 | Ph | H | H | CH | O |
| 13.164 | pyridin-3-yl | XIV | 1 | 0 | Ph | H | H | CH | O |
| 13.165 | pyridin-4-yl | XIV | 1 | 0 | Ph | H | H | CH | O |
| 13.166 | pyrimidin-2-yl | XIV | 1 | 0 | Ph | H | H | CH | O |
| 13.167 | pyrimidin-4-yl | XIV | 1 | 0 | Ph | H | H | CH | O |
| 13.168 | thien-2-yl | XIV | 1 | 0 | Ph | H | H | CH | O |
| 13.169 | thien-3-yl | XIV | 1 | 0 | Ph | H | H | CH | O |
| 13.170 | 1-napthyl | XIV | 1 | 0 | Ph | H | H | CH | O |
| 13.171 | 2-napthyl | XIV | 1 | 0 | Ph | H | H | CH | O |
| 13.172 | 2-furyl | XIV | 1 | 0 | Ph | H | H | CH | O |
| 13.173 | 3-furyl | XIV | 1 | 0 | Ph | H | H | CH | O |
| 13.174 | 2-(Ph)cyclopropyl | XIV | 1 | 0 | Ph | H | H | CH | O |
| 13.175 | 2-methylcyclopropyl | XIV | 1 | 0 | Ph | H | H | CH | O |
| 13.176 | 2-ethylcyclopropyl | XIV | 1 | 0 | Ph | H | H | CH | O |
| 13.177 | 2-(n-propyl)cyclopropyl | XIV | 1 | 0 | Ph | H | H | CH | O |
| 13.178 | 2-(n-butyl)cyclopropyl | XIV | 1 | 0 | Ph | H | H | CH | O |
| 13.179 | 2-(iso-butyl)cyclopropyl | XIV | 1 | 0 | $CH_3$ | H | H | CH | O |
| 13.180 | 2-(m-hexyl)cyclopropyl | XIV | 1 | 0 | $CH_3$ | H | H | CH | O |
| 13.181 | 2-methoxycyclopropyl | XIV | 1 | 0 | $CH_3$ | H | H | CH | O |
| 13.182 | 2-ethoxycyclopropyl | XIV | 1 | 0 | $CH_3$ | H | H | CH | O |
| 13.183 | 2-(n-propoxy)cyclopropyl | XIV | 1 | 0 | $CH_3$ | H | H | CH | O |
| 13.184 | 1-methylcyclopropyl | XIV | 1 | 0 | $CH_3$ | H | H | CH | O |
| 13.185 | 2-($CH=CH_2$)cyclopropyl | XIV | 1 | 0 | $CH_3$ | H | H | CH | O |
| 13.186 | 2-(1-cyclopropyl)cyclopropyl | XIV | 1 | 0 | $CH_3$ | H | H | CH | O |
| 13.187 | 2-(2-cyclopropyl)cyclopropyl | XIV | 1 | 0 | $CH_3$ | H | H | CH | O |
| 13.188 | cyclopropyl-$CH_2$ | XIV | 1 | 0 | $CH_3$ | $CH_3$ | H | CH | O |
| 13.189 | cyclopropyl-CH=CH | XIV | 1 | 0 | $CH_3$ | $CH_3$ | H | CH | O |
| 13.190 | 1-(Ph)cyclopropyl | XIV | 1 | 0 | $CH_3$ | $CH_3$ | H | CH | O |
| 13.191 | 2-(Ph)cyclopropyl | XIV | 1 | 0 | $CH_3$ | $CH_3$ | H | CH | O |
| 13.192 | 1-(2'-Cl(Ph))cyclopropyl | XIV | 1 | 0 | $CH_3$ | $CH_3$ | H | CH | O |
| 13.193 | 2-(2'-CL(Ph))cyclopropyl | XIV | 1 | 0 | $CH_3$ | $CH_3$ | H | CH | O |
| 13.194 | 1-(3'-Cl(Ph))cyclopropyl | XIV | 1 | 0 | $CH_3$ | $CH_3$ | H | CH | O |
| 13.195 | 2-(3'-Cl(Ph))cyclopropyl | XIV | 1 | 0 | $CH_3$ | $CH_3$ | H | CH | O |
| 13.196 | 1-(4'-Cl(Ph))cyclopropyl | XIV | 1 | 0 | $CH_3$ | $CH_3$ | H | CH | O |
| 13.197 | 2-(4'-Cl(Ph))cyclopropyl | XIV | 1 | 0 | $CH_3$ | $CH_3$ | H | CH | O |
| 13.198 | 1-(2'-F(Ph))cyclopropyl | XIV | 1 | 0 | $CH_3$ | $CH_3$ | H | CH | O |
| 13.199 | 2-(2'-F(Ph))cyclopropyl | XIV | 1 | 0 | $CH_3$ | $CH_3$ | H | CH | O |
| 13.200 | 2-(3'-F(Ph))cyclopropyl | XIV | 1 | 0 | $CH_3$ | $CH_3$ | H | CH | O |
| 13.201 | 2-(4'-F(Ph))cyclopropyl | XIV | 1 | 0 | $CH_3$ | $CH_3$ | H | CH | O |
| 13.202 | 2-(2'-Br(Ph))cyclopropyl | XIV | 1 | 0 | $CH_3$ | $CH_3$ | H | CH | O |
| 13.203 | 2-(3'-Br(Ph))cyclopropyl | XIV | 1 | 0 | $CH_3$ | $CH_3$ | H | CH | O |
| 13.204 | 2-(4'-Br(Ph))cyclopropyl | XIV | 1 | 0 | $CH_3$ | $CH_3$ | H | CH | O |

TABLE XIII-continued

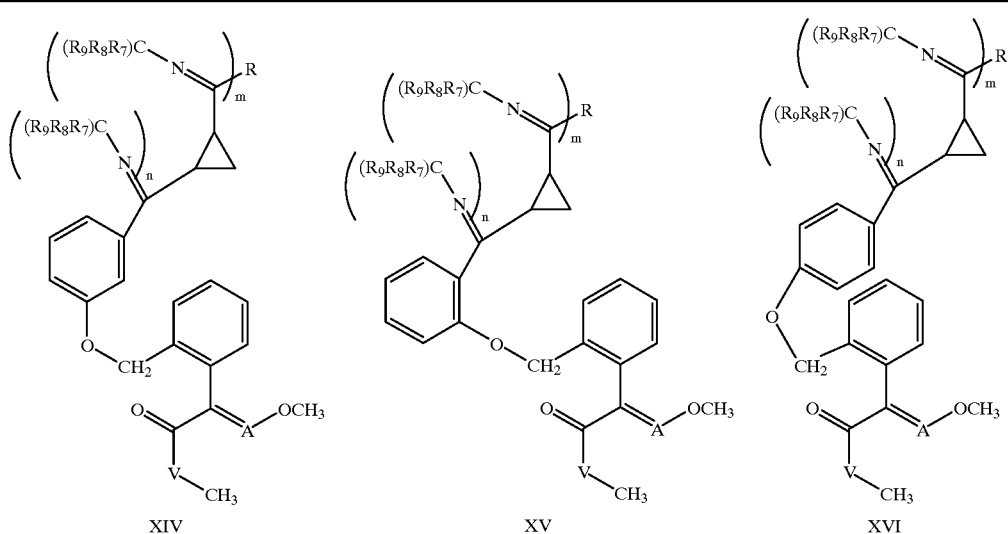

XIV                XV                XVI

| Cmpd # | R | Formula | n | m | R$_7$ | R$_8$ | R$_9$ | A | V |
|---|---|---|---|---|---|---|---|---|---|
| 13.205 | 2-(2'-F(Ph))cyclopropyl | XIV | 1 | 0 | CH$_3$ | CH$_3$ | H | CH | O |
| 13.206 | 2-(2'-CH$_3$(Ph))cyclopropyl | XIV | 1 | 0 | CH$_3$ | CH$_3$ | H | CH | O |
| 13.207 | 2-(3'-CH$_3$(Ph))cyclopropyl | XIV | 1 | 0 | CH$_3$ | CH$_3$ | H | CH | O |
| 13.208 | 2-(4'-CH$_3$(Ph))cyclopropyl | XIV | 1 | 0 | CH$_3$ | CH$_3$ | H | CH | O |
| 13.209 | 2-(2'-CF$_3$((Ph)))cyclopropyl | XIV | 1 | 0 | CH$_3$ | CH$_3$ | H | CH | O |
| 13.210 | 2-(3'-CF$_3$(Ph))cyclopropyl | XIV | 1 | 0 | CH$_3$ | CH$_3$ | H | CH | O |
| 13.211 | 2-(4'-CF$_3$(Ph))cyclopropyl | XIV | 1 | 0 | CH$_3$ | CH$_3$ | H | CH | O |
| 13.212 | 1-(Ph)cyclopentyl | XIV | 1 | 0 | CH$_3$ | CH$_3$ | H | CH | O |
| 13.213 | 1-(Ph)cyclohexyl | XIV | 1 | 0 | CH$_3$ | CH$_3$ | H | CH | O |
| 13.214 | 2-(Ph)cyclopentyl | XIV | 1 | 0 | CH$_3$ | CH$_3$ | H | CH | O |
| 13.215 | 2-(Ph)cyclohexyl | XIV | 1 | 0 | CH$_3$ | CH$_3$ | H | CH | O |
| 13.216 | 2-(2'-(Ph)cyclopropyl)cyclopropyl | XIV | 1 | 0 | H | H | H | CH | O |
| 13.217 | 2-(1'-(Ph)cyclopropyl)cyclopropyl | XIV | 1 | 0 | H | H | H | CH | O |
| 13.218 | 2-(PhCH$_2$)cyclopropyl | XIV | 1 | 0 | H | H | H | CH | O |
| 13.219 | 2-(2'-Cl(Ph)CH$_2$)cyclopropyl | XIV | 1 | 0 | H | H | H | CH | O |
| 13.220 | 2-(4'-Cl(Ph)CH$_2$)cyclopropyl | XIV | 1 | 0 | H | H | H | CH | O |
| 13.221 | 2-(2'-(PhCH$_2$)cyclopropyl)cyclopropyl | XIV | 1 | 0 | H | H | H | CH | O |
| 13.222 | 2-(1'-(PhCH$_2$)cyclopropyl)cyclopropyl | XIV | 1 | 0 | H | H | H | CH | O |
| 13.223 | 2-(2'-pyridyl)cyclopropyl | XIV | 1 | 0 | H | H | H | CH | O |
| 13.224 | 2-(3'-pyridyl)cyclopropyl | XIV | 1 | 0 | H | H | H | CH | O |
| 13.225 | 2-(2'-furyyl)cyclopropyl | XIV | 1 | 0 | H | H | H | CH | O |
| 13.226 | 2-(3'-furylyl)cyclopropyl | XIV | 1 | 0 | H | H | H | CH | O |
| 13.227 | 2-(2'-thienyl)cyclopropyl | XIV | 1 | 0 | H | H | H | CH | O |
| 13.228 | 2-(3'-thienyl)cyclopropyl | XIV | 1 | 0 | H | H | H | CH | O |

Further typical compounds described by the present invention are described in the following tables.

Table XIV: Compounds 14.01 to 228 are Compounds of Table XIII of Formula XIV, XV, XVI where V=O and A is N Table XV: Compounds 15.01 to 228 are Compounds of Table XIII of Formula XIV, XV, XVI where V=NH and A is N As used in Tables I to XV Ph is understood to be phenyl.

Scheme A describes the general preparation of compounds of the Formula (I). where A is CH or N, and V is O. The cyclopropyl substituted phenols (XVII) are reacted with the appropriately substituted benzyl bromide derivative (XVIII). Cyclopropyl substituted phenols represented by the general formula (XVII) are treated, at room temperature, with an appropriate base to form an anion, followed by the addition of the benzyl bromide. Typical bases employed are metal hydrides such as sodium hydride, alkoxides such as sodium methoxide and hydroxide bases such as sodium or potassium hydroxide and alkali bases such as sodium or potassium carbonate. Typical solvents employed with hydride bases are N, N-dimethylformamide (DMF) and tetrahydrofuran (THF); with hydroxide bases DMF, THF, methyl ethyl ketone (MEK) and acetone and with alkali bases solvents such as DMF, acetone, and MEK.

Scheme A

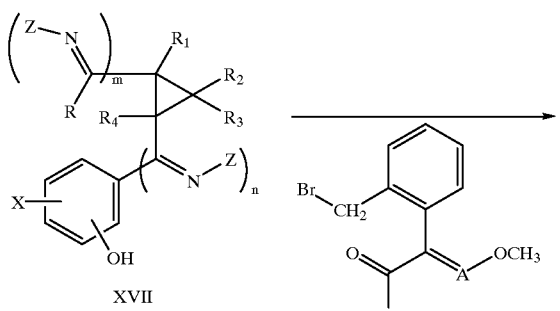

an alkyl nitrite under basic conditions to provide after methylation, methyl 2-methylphenylglyoxalate O-methyl oxime which can also be prepared from methyl 2-methylphenylglyoxalate by treatment with 2-hydroxylamine hydrochloride and methylation or by treatment with methoxylamine hydrochloride.

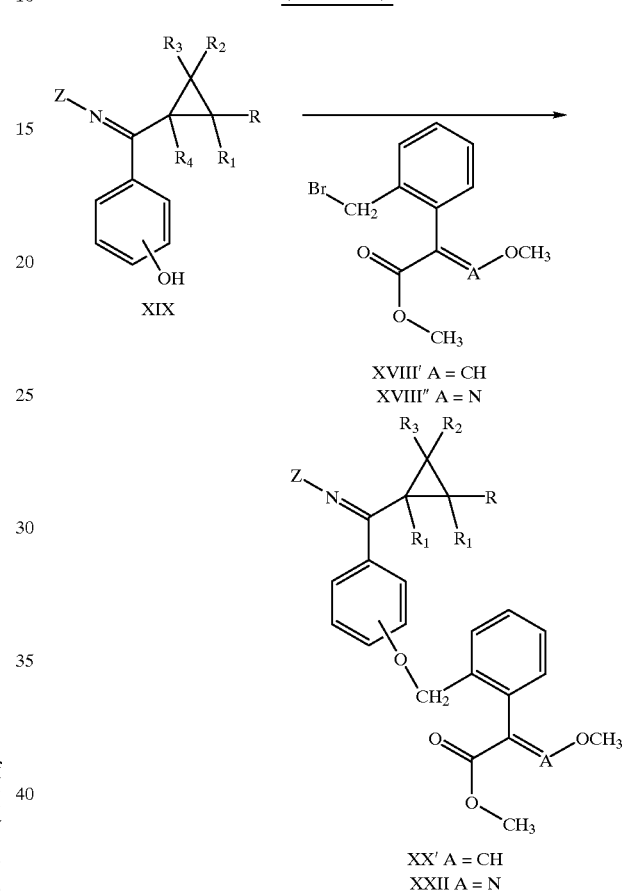

Scheme B describes the preparation of the compounds of Formula XX (m=0 and n=1) of Tables VII, VIII, X. XI, XIII and XIV. Compounds of Formula XX' where A is CH and V is O (Tables VII, X, XIII) are prepared by alkylation of the cyclopropane intermediate XIX with methyl E-α-(2-bromomethylphenyl)-β-methoxyacrylate. XVIII', in the presence of a base, preferably NaOH or KOH, in a solvent, preferably acetone or methyl ethyl ketone. Methyl E-α-(2-bromomethylphenyl)-β-methoxyacrylate, XVIII', as a single E isomer, can be prepared in two steps from 2-methylphenylacetate as described previously in U.S. Pat No. 4,914,128, columns 3–4. As is shown in Scheme B compounds of Formula XXII (m=0 and n=1, A is N and V is O of Tables VIII, XI, XIV) are prepared by the reaction with methyl E-2-(bromomethyl)-phenylglyoxylate O-methyloxime, XVIII'', in the presence of a base, preferably NaOH or KOH, in a solvent, preferably acetone or methyl ethyl ketone. Methyl 2-(bromomethyl) phenylglyoxylate O-methyloxime can be prepared as described in U.S. Pat. No. 4,999,042, columns 17–18 and U.S. Pat. No. 5,157,144, columns 17–18. Methyl 2-(bromomethyl)phenylglyoxylate O-methyl oxime is prepared from methyl 2-methylphenylacetate by treatment with As shown in scheme C compounds of formula XXIII where m=0 and n=1 and A is N and V is NH) prepared by the aminolysis of oximinoacetate XXII (A is N and V is O). The aminolysis of oximinoacetate to oximinoacetamides has been described in U.S. Pat. No. 5,185,342, cols. 22, 48 and U.S. Pat. No. 57, 5,221,691, cols. 26–27 and U.S. Pat. No. 5,407,902, col. 8. For example, compounds of Tables VIII, XI and XIV where A is N and Z is O are treated with 40% aqueous methylamine in methanol to provide compounds of Tables IX, XII and XV where V is NH. Alternatively, as is shown in scheme C intermediate cyclopropane XIX is reacted with N-methyl (E)-2-methoxyimino-2-[2-(bromomethyl)phenyl]acetamide, XXI, in the presence of a base such as an hydroxide base preferably in a solvent such as acetone or methyl ethyl ketone to directly provide compounds of formula XXIII. N-methyl (E)-2-methoxy-imino-2-[2-(bromomethyl)phenyl]-acetamide is described in U.S. Pat. No. 5,387,714, col. 13.

Scheme C

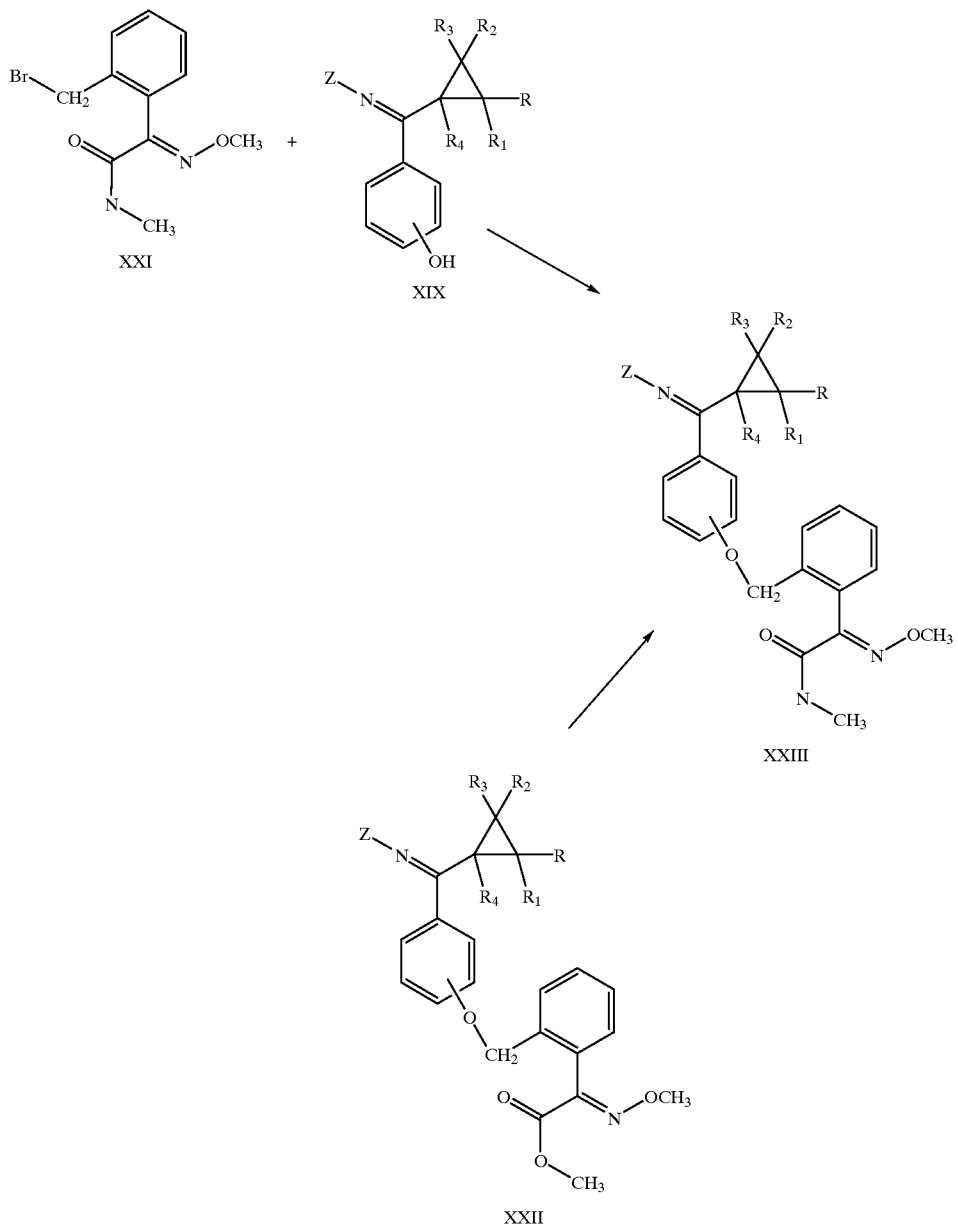

Scheme D describes the preparation of the compounds of formula XXV (m=1 and n=0) of Tables 1, II, IV, V, X, XI, XIII and XIV. The alkylations of the cyclopropane intermediates XXIV with the benzyl bromide XVIII', where A is CH and V is O, are compounds of Tables I, IV, X and XIII. Also shown in Scheme D is the preparation of compounds of formula XXV (m=1 and n=0) where A is N and V is O and are compounds of Tables II, V, XI and XIV.

Scheme D
(n = 0, m = 1)

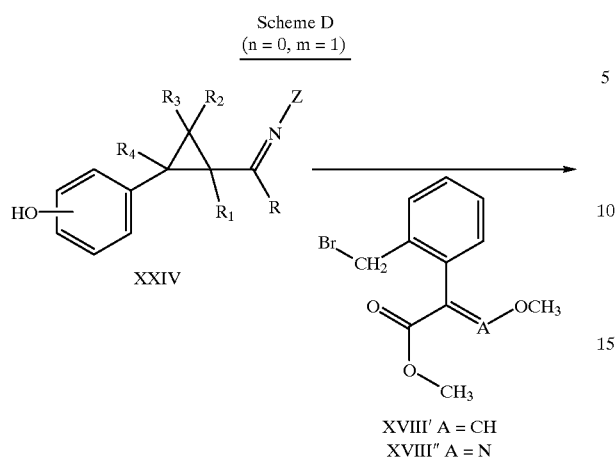

XXIV

XVIII' A = CH
XVIII" A = N

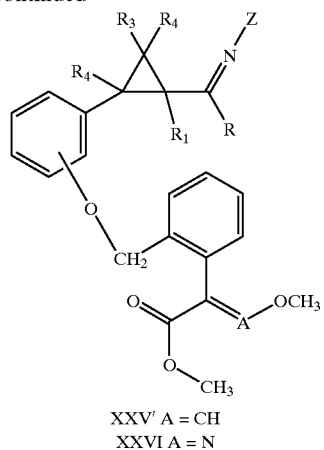

XXV' A = CH
XXVI A = N

As shown in scheme E, compounds of formula XXVII (where m=1 and n=0 and A is N and V=NH) are prepared by the aminolysis of oximinoacetate XXVI Is (A is N and V is O) as described for scheme C. For example, compounds of Tables II, V, XI and XIV where A is N and Z is O are treated with 40% aqueous methylamine in methanol to provide compounds of Tables III, VI, XII and XV where V is NH. Alternatively, as is shown in scheme E intermediate cyclopropane XXIV is reacted with XXI as described for scheme C to directly provide compounds of formula XXVII of Tables III, VI, XII and XV.

Scheme E
(n = 1, m = 0)

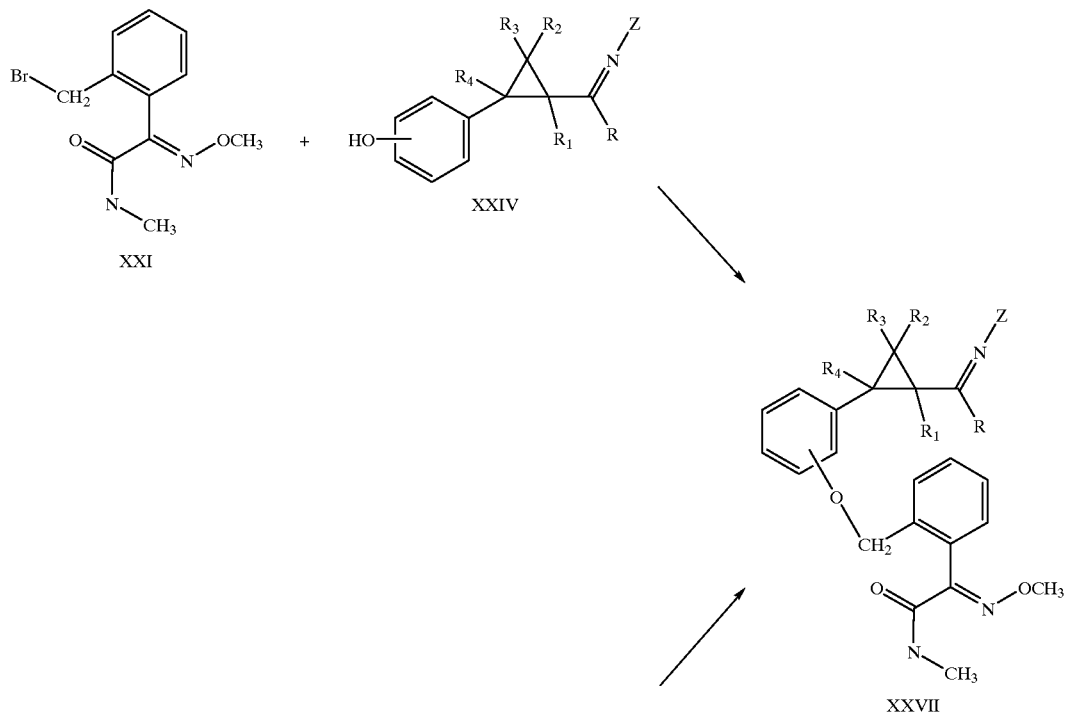

XXI

XXIV

XXVII

-continued

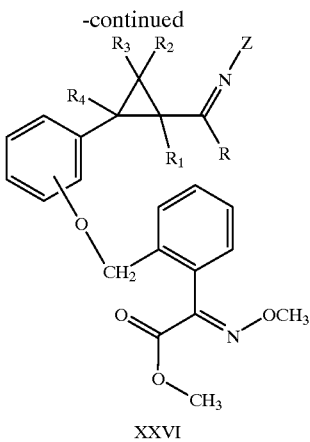

XXVI

The substituted cyclopropyl derivatives of the general formula XVII can be obtained, as shown in scheme F, by reacting the corresponding cyclopropane ketones and aldehydes (XXVIII) with $NH_2OR_5$, $NH_2NR_5R_6$ or $NH_2R_7R_8R_9$ from room temperature to reflux, preferably at room temperature, in an appropriate solvent such as methanol or ethanol in the presence of an appropriate alkali such as sodium hydroxide, potassium carbonate or pyridine. A general description of the synthesis of oximes, imines and hydrazones from carbonyl compounds is described in March, *Advanced Organic Chemistry*, 4th Ed, pp. 894 and 904–907 and references therein. The compounds of the general formula XVII and specifically XIX and XXIV when obtained as a mixture of syn or anti oxime isomers can be separated into individual isomers and alkylated as described in Schemes A to E. When a mixture of compounds of the general formula XVII and specifically XIX and XXIV are used in Scheme A to E the compounds of the formula I can be separated into their individual isomers by conventional chromatographic techniques sulfur ylide, prepared from a dimethylsulfoxonium salt in the presence of a base, resulting in the substituted acyl cyclopropanes, XXVIII. The chemistry of sulfur ylides is described in Trost and Melvin, *Sulfur Ylids*, Academic Press, New York, N.Y. 1975 and in Block, *Reactions of Organosulfur Compounds*, pp. 91–123, Academic Press, New York, N.Y. 1978. Typical reaction conditions for sulfur ylide formation to from a dimethylsulfoxonium salt utilizes bases such as hydroxides, metal hydrides and alkoxides in solvents such as dimethoxyethane, dimethylsulfoxide and water depending on the base employed. The reactions are conducted from 0 to 20° C. preferably from 10–15° C. and preferably with alkali metal hydroxides in dimethylsulfoxide. Typically dimethylsulfoxonium methylide is prepared from trimethylsulfoxonium iodide in dimethylsulfoxide in the presence of powdered sodium hydroxide at room temperature. The unsaturated ketones or aldehydes, XXIX are added drop wise to the ylide and stirred at room temperature.

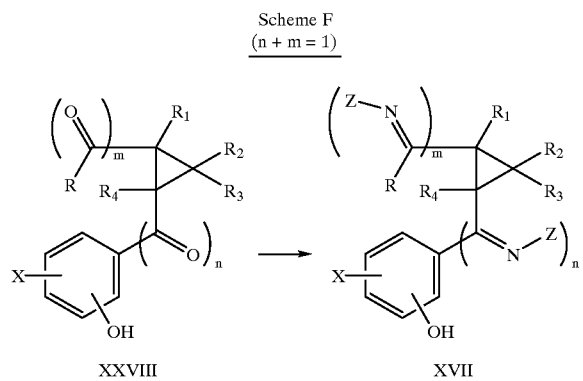

Scheme F
(n + m = 1)

XXVIII    XVII

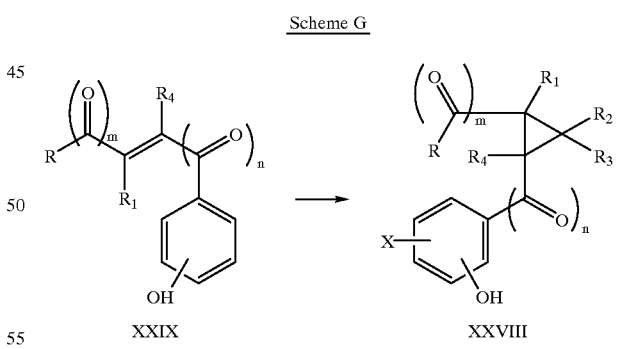

Scheme G

XXIX    XXVIII

The general synthesis of the cyclopropanes of the general Formula XXVIII are described in EP 0889024. The cyclopropanes of the general Formula XXVIII can be prepared by conventional techniques as shown in scheme G. The unsaturated intermediate XXIX (Scheme J) is reacted with a Scheme H describes the preparation of benzoylcyclopropanes of the Formula XXVIII$^I$ where n=1 and m=0, by reaction of the enone, XXIX$^I$, with the sulfur ylid $(CH_3)_2S(O)=CR_2R_3$. Additionally, in Scheme H is shown the preparation of the acylcyclopropane phenols of Formula XXVIII$^{II}$ where n=0 and m=1 by reaction of the enone, XXIX$^{II}$ with the ylide $(CH_3)_2S(O)=CR_2R_3$.

Scheme H when n = 1, m = 0

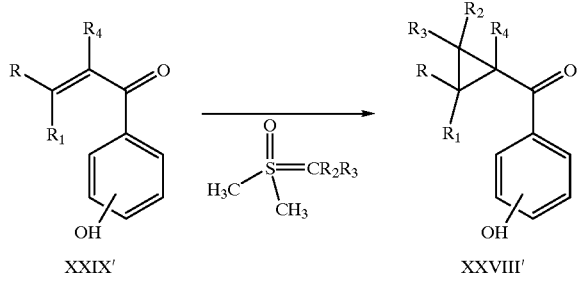

when n = 0, m = 1

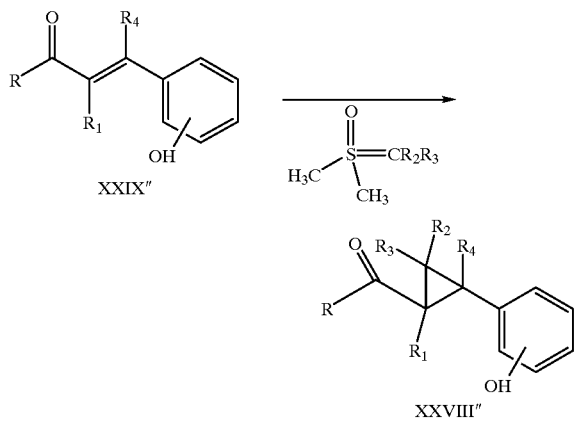

Scheme I describes the preparation of benzoylcyclopropanes (XXVIII) and cyclopropylimines (XVII) where $R_1$–$R_4$ are hydrogen. When n=1 and m=0 the cyclopropane $XVII^{III}$ is prepared from the benzoylcyclopropanes $XXVIII^{III}$ which is prepared from the unsaturated intermediate $XXIX^{III}$ via the sulfur ylide as described in Scheme G. The enones $XXIX^{III}$ are prepared by conventional techniques from the aldehydes RCHO and the isomeric substituted hydroxyacetophenones. When n=0 and m=1 the cyclopropane $XVII^{IV}$ is prepared from the acylcyclopropane $XXVIII^{IV}$ which is prepared from the unsaturated intermediate $XXIX^{IV}$ as described in Scheme G. The enones $XXIX^{IV}$ are prepared by conventional techniques from the ketones $RCOCH_3$ and the isomeric substituted hydroxybenzaldehydes.

Scheme I when n = 1, m = 0, and $R_1$, $R_2$, $R_3$ $R_4$ = H

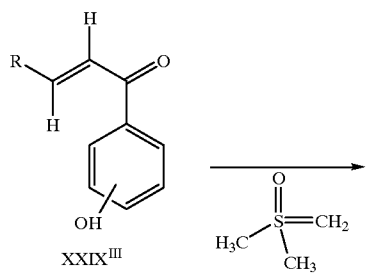

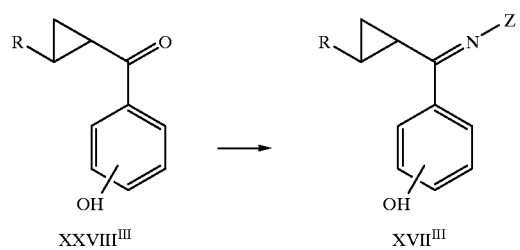

when n = 0, m = 1, and $R_1$, $R_2$, $R_3$, $R_4$ = H

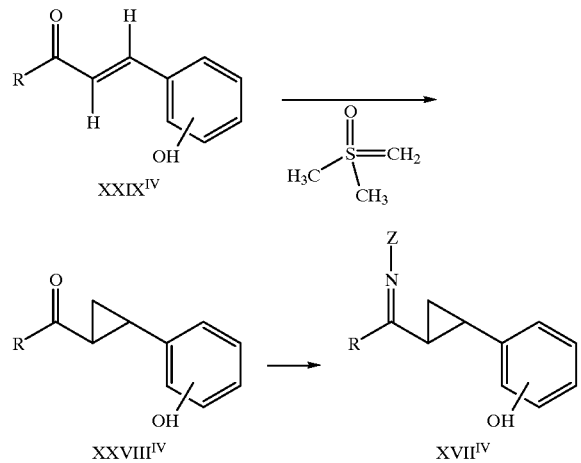

Alternatively the cyclopropyl ketones XXVIII, specifically $XXVIII^{I}$ and $XXVIII^{III}$, can be prepared from cyclopropyl nitrites XXXI which are prepared via cyclopropanation of the acrylonitriles XXX as is described in Scheme J. The acrylonitriles starting materials (XXX), shown in Scheme J can be prepared by conventional synthetic methods as described in March, *Advanced Organic Chemistry*, 4th Ed, pp. 937–955 and references therein. For the benzoylcyclopropanes, $XXVIII^{I}$, where n=1 and m=0 the nitrile derivative $R_4CH_2CN$ is condensed with the ketone or aldehyde RCOR, in the presence of a base to provide the acrylonitriles $XXX^{I}$. Typically the nitrile is dissolved in a solvent such as ethanol and water to which is added the aldehyde or ketone followed by a base. Typical bases used can be alkali metal hydroxides, such as barium, potassium or sodium hydroxide and the mixture is stirred typically at ambient temperature.

Scheme J

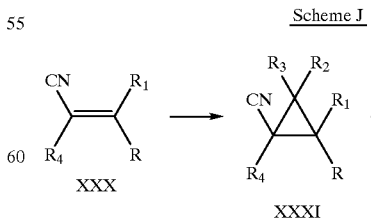 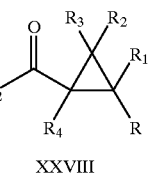

Scheme K

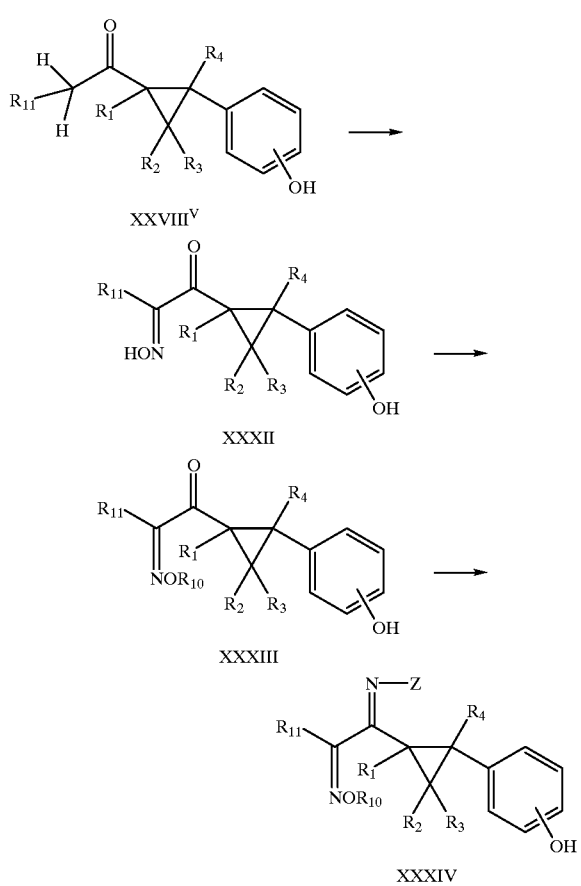

when n = 1 and m = 0

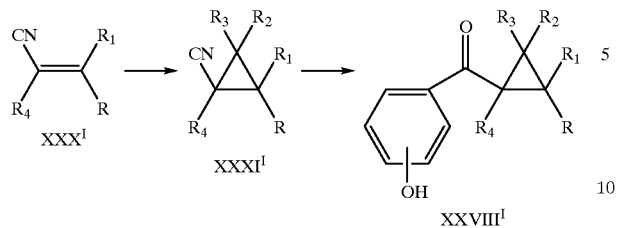

when n = 0 and m = 1

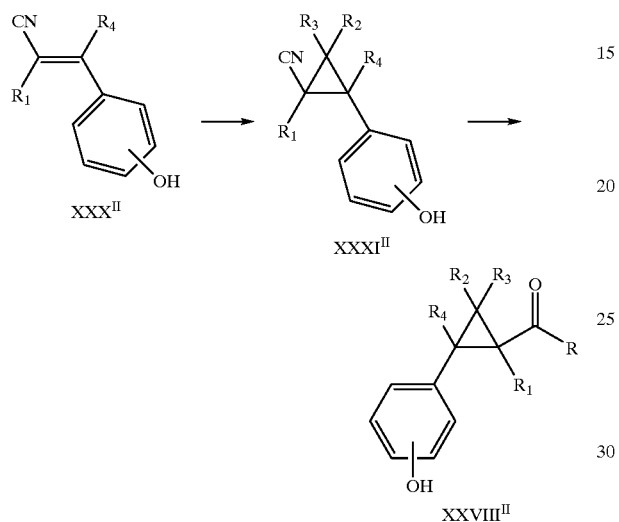

For the arylcyclopropanes, XXVIIIII, where n=0 and m=1 the nitrile derivative $R_1CH_2CN$ is condensed with the arylketone or benzaldehyde $(HO)PhCOR_4$ in the presence of a base to provide the acrylonitriles $XXX^{II}$. The acrylonitriles $XXX^I$ and $XXX^{II}$ are treated as is described in Scheme G with a sulfur ylide to provide the cyclopropyl nitrites $XXXI^I$ and $XXXI^{II}$. The cyclopropyl nitrites are transformed to the cyclopropyl ketones by organometallic addition to the nitrite followed by hydrolysis. For example when n=1 and m=0 the Grignard reagent is an aryl Grignard reagent and when n=0 and m=1 a Grignard reagent or an organolithium reagent, RLi adds to the nitrite functionality to provide the ketones $XXVIII^I$ and $XXVIII^I$, respectively. The addition reaction to nitrites are described in March, *Advanced Organic Chemistry*, 4th Ed, pp.935–936 and references cited therein.

Scheme K describes the preparation of the compounds of Formula XXIV where n=0 and m=1 in which R is $C(R_{11})$ =N—OR$_{10}$. The ketones, $XXVIII^V$, wherein $R_{10}$ is not H, or the aldehydes $R_{10}$ is H, are reacted with an alkyl nitrite such as t-butylnitrite or isoamylnitrite under basic conditions to provide the corresponding α-oximino cyclopropylketones XXXII. Typically the cyclopropyl ketone or aldehydes in a solvent such as t-butanol and the alkyl nitrite, typically t-butylnitrite, is added to a solution t-butanol containing a base such as potassium t-butoxide and is stirred at room temperature. The α-hydroxyimino cyclopropylketones XXXII are alkylated with $R_{10}X$ to provide the α-(substituted)oximino cyclopropylketones XXXIII. Finally, the intermediate XXXIV is formed by reaction with $NH_2OR_5$, $NH_2NR_5R_6$ or $NH_2R_7R_8R_9$ as is described previously in Scheme F.

Alternatively the compounds of Formula I can be prepared as described in Scheme L.

The compounds of Formula XXXV which are described in EP 0889024 can be reacted directly with $NH_2OR_5$, $NH_2NR_5R_6$ or $NH_2R_7R_8R_9$ as is described previously in Scheme F to provide compounds of the Formula I.

Scheme L

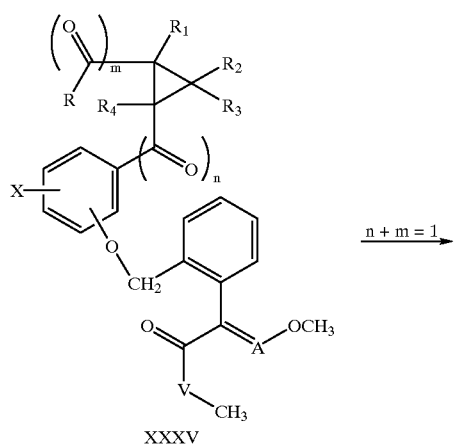

n + m = 1

-continued

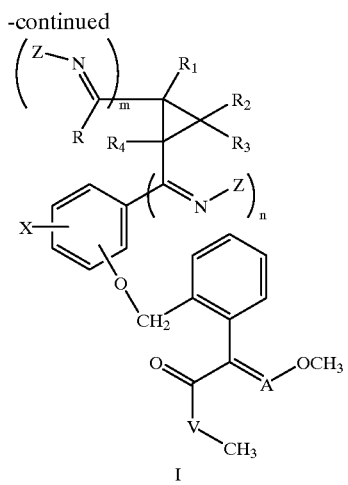

The compounds of this invention can be made according to the following procedures:

EXAMPLE 1

Methods of Schemes B and I
Preparation of Methyl (E)-3-methoxy-2-trans-[2-(3-(2-(2-ethyl-1-(2-phenylhydrazino)propylidene)cyclopropyl) phenoxymethyl)phenyl]-2-propenoate. propenoate. (Compound 4.17, Table 4)

Preparation of 2-(3-Hydroxyphenyl)cyclopropyl 1-Methylpropyl Ketone

To a 250 ml round bottom flask equipped with magnetic stirrer, nitrogen inlet, thermometer and addition funnel was charged 1.6 g (0.039 moles) of powdered sodium hydroxide, 8.7 g (0.039 moles) of trimethyl sulfoxonium iodide, and 50 mls of anhydrous DMSO. The mixture was then stirred at ambient temperature for 30 minutes. The mixture was then cooled to 15° C., and a solution of 1-(1-methylpropyl)-3-(3-hydroxyphenyl)-2-propene-1-one (4.0 g, 0.0196 moles) was added dropwise in 50 mls of DMSO. The reaction was stirred for 1 hour at 15° C., then allowed to warm to ambient temperature, and stirred for an additional 16 hours. The reaction mixture was the quenched with 100 mls of 0.1 N HCl, and extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45 ° C. to afford 3.6 g of the title compound, 2-(3-hydroxyphenyl)cyclopropyl 1-methylpropyl ketone, as a thick amber oil in an 85% crude yield.

300 MHz $^1$H NMR (CDCl$_3$, tms=0 ppm) 0.7(m, 3H); 1.1(m, 3H); 1.4(m, 2H); 1.9(m, 2H); 2.1(m, 1H); 2.3(m, 1H); 2.5(m, 1H); 6.4(bs, 1H); 6.6(m, 2H); 6.7(m, 1H); 7.1(t, 1H).

Preparation of N-Phenyl-N'-(1-(2-(3-hydroxyphenyl) cyclopropyl)-2-ethyl)propylidene-hydrazine To a 100 ml round bottom flask equipped with a magnetic stirrer and reflux condenser was charged 1.0 g (0.0049 moles) of 2-(3-hydroxyphenyl)cyclopropyl 1-methylpropyl ketone, 50 ml of dry toluene, and 0.9 g (0.008 moles) of phenyl hydrazine. The reaction was heated at reflux for a total of 2 hours, then cooled and poured into 100 mls of water. The aqueous solution was extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45° C. to afford 0.6 g of the title compound, N-phenyl-N'-(1-(2-(3-hydroxyphenyl) cyclopropyl)-2-ethyl)propylidene-hydrazine, as a thick brown liquid in a 40% crude yield.

300 MHz $^1$H NMR (CDCl$_3$, tms=0 ppm) 0.8(m, 3H); 1.1(m, 3H); 1.2–1.4(m, 4H); 1.6(m, 1H); 2.0(m, 1H); 2.2(m, 1H); 6.5–7.5(m, 11H)

Methyl (E)-3-methoxy-2-trans-[2-(3-(2-(2-ethyl-1-(2-phenylhydrazino)propylidene)cyclopropyl)ohenoxymethyl) phenyl]-2-propenoate.

To a 20 ml glass vial equipped with a magnetic stirring bar was charged 0.6 g (0.00195 moles) of N-Phenyl-N'-(1-(2-(3-hydroxyphenyl)cyclopropyl)-2-ethyl)propylidene-hydrazine, 10 mls of dry N, N-dimethylformamide, and 0.08 g (0.00195 moles) of powdered sodium hydroxide. To this mixture was added 0.55 g (0.00195 moles) of methyl α-(2-(bromomethyl)phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 3.9 g of the crude product as an amber oil. This material was chromatographed on a mixed bed of neutral alumina and silica gel with 30% ethyl acetate, 70% hexane. The pure fractions were combined, and concentrated under reduced pressure with a rotary evaporator at 45 ° C. to afford 0.25 g of the title compound, methyl (E)-3-methoxy-2-trans-[2-(3-(2-(2-ethyl-1-(2-phenylhydrazino)propylidene)cyclopropyl) phenoxymethyl)phenyl]-2-propenoate as a viscous brown oil in a 26% isolated yield.

300 MHz $^1$H NMR (CDCl$_3$, tms=0 ppm): 0.8(m, 3H); 1.1(m, 3H); 1.2–1.4(m, 3H); 1.8–1.9(m, 2H); 2.2(m, 1H); 3.7(s, 3H); 3.85(s, 3H); 4.9(s, 2H); 6.8(m, 4H); 7.0(m, 1H); 7.2(m, 5H); 7.4(m, 2H); 7.6(m, 3H).

EXAMPLE 2

Methods of Schemes B and I
Preparation of Methyl (E)-3-methoxy-2-trans-[2-(3-(2-(methoximinocycloprop-1-yl)cyclopropyl) phenoxymethyl) phenyl]-2-propenoate. (Compound 1.34, Table 1)
Preparation of 2-(3-Hydroxyphenyl)cyclopropyl Cyclopropyl Ketone To a 500 ml round bottom flask equipped with magnetic stirrer, nitrogen inlet, thermometer and addition funnel was charged 20 g (0.5 moles) of powdered sodium hydroxide, 110 (0.5 moles) of trimethyl sulfoxonium iodide, and 200 mls of anhydrous DMSO. The mixture was then stirred at ambient temperature for 30 minutes. The mixture was then cooled to 15° C., and a solution of 1-cyclopropyl-3-(3-hydroxyphenyl)-2-propene-1-one (47 g, 0.25 moles) was added dropwise in 50 mls of DMSO. The reaction was stirred for 2 hours at 10–15° C., then allowed to warm to ambient temperature, and stirred for an additional 16 hours. The reaction mixture was the quenched with 200 mls of 0.1 N HCl, and extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45° C. to afford 32 g of the title compound, 2-(3-hydroxyphenyl)cyclopropyl cyclopropyl ketone, as a thick amber oil that crystallized upon standing in a 64% isolated yield.

300 MHz $^1$H NMR (CDCl$_3$, tms=0 ppm): 0.9(m, 2H); 1.1(m, 2H); 1.4(m, 1H); 1.8 (m, 1H); 2.1(m, 1H); 2.4(m, 1H); 2.6(m, 1H); 6.5(m, 3H); 7.2(t, 1H).

Preparation of 2-(3-Hydroxyphenyl)cyclopropyl Cyclopropylmethanone O-methyl Oxime To a 50 ml round bottom flask equipped with a magnetic stirrer was charged 2.0 g (0.01 moles) of 2-(3-hydroxyphenyl)cyclopropyl cyclopropyl ketone, 20 ml of anhydrous methanol, and 1.3 g (0.015 moles) of methoxylamine hydrochloride. The reaction was stirred at ambient temperature for three days, then poured into 100 mls of water and extracted with 3×50 mls of ethyl ether. The ether extract was then washed with 2×50 mls of water and 50 mls of saturated aqueous sodium chloride solution. The ether extract was then dried over anhydrous magnesium sulfate, filtered, and concentrated under reduced pressure with a rotary evaporator at 45° C. to afford 1.7 g of the crude product, 2-(3-hydroxyphenyl)cyclopropyl cyclopropylmethanone O-methyl oxime (a mixture of isomeric O-methyl oximes), as a brown oil.

300 MHz $^1$H NMR (CDCl$_3$, tms=0 ppm): 0.7(m, 2H); 0.9(m, 2H); 1.1(m, 2H); 1.5 (m, 1H); 2.0(m, 1H); 2.4(m, 1H); 3.9(d, 3H); 5.8(bs, 1H); 6.6(m, 3H); 7.2(m, 1H).

Preparation of Methyl (E)-3-methoxy-2-trans-[2-(3-(2-((1-(cyclopropyl)meth-oximinometh-1-yl)cyclopropyl)phenoxymethyl)phenyl]-2-propenoate. (Compound 1.34, Table 1)

To a 20 ml glass vial equipped with a magnetic stirring bar was charged 1.7 g (0.00736 moles) of 2-(3-hydroxyphenyl)cyclopropyl cyclopropyl cyclopropylmethanone O-methyl oxime, 10 mls of dry N, N-dimethylformamide, and 0.3 g (0.00736 moles) of powdered sodium hydroxide. To this mixture was added 2.1 g (0.00736 moles) of methyl α-(2-(bromomethyl)phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 1.9 g of the crude product as a dark amber oil. This material was chromatographed on a mixed bed of neutral alumina and silica gel with 30% ethyl acetate, 70% hexane. The pure fractions were combined, and concentrated under reduced pressure with a rotary evaporator at 45° C. to afford 0.7 g of the title compound, methyl (E)-3-methoxy-2-trans-[2-(3-(2-(methoximinocycloprop-1-yl)cyclopropyl) phenoxymethyl) phenyl]-2-propenoate as a viscous pale amber oil in a 22% isolated yield.

300 MHz $^1$H NMR (CDCl$_3$, tms=0 ppm): 0.6(d, 1H); 0.7(m, 3H); 1.1(m, 2H); 1.5(m, 1H); 2.0(m, 1H); 2.3(m, 1H); 3.7(s, 3H); 3.75(s, 3H); 3.8(s, 3H); 4.9(s, 2H); 6.6(m, 1H); 6.7(d, 2H); 7.1(m, 2H); 7.3(m, 2H); 7.6(m, 1H); 7.7(s, 1H).

EXAMPLE 3

Method of Scheme L

Preparation of Methyl (E)-3-methoxy-2-trans-[2-(3-(2-(methoximinohept-1-yl)cyclopropyl)-phenoxymethyl) phenyl]-2-propenoate. (Compound 1.23, Table 1)

Preparation of 2-(3-Hydroxyphenyl)cyclopropyl n-hexyl Ketone

To a 300 ml round bottom flask equipped with magnetic stirrer, nitrogen inlet, thermometer and addition funnel was charged 0.3 g (0.0069 moles) of powdered sodium hydroxide, 1.5 g (0.0069 moles) of trimethyl sulfoxonium iodide, and 50 mls of anhydrous DMSO. The mixture was then stirred at ambient temperature for 1 hour. The mixture was then cooled to 15° C., and a solution of 1-n-hexyl-3-(3-hydroxyphenyl)-2-propene-1-one (0.8 g, 0.0069 moles) was added dropwise in 5 mls of DMSO. The reaction was stirred for 1 hour at 10–15° C., then allowed to warm to ambient temperature, and stirred for an additional 16 hours. The reaction mixture was the quenched with 200 mls of 0.1 N HCl, and extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45° C. to afford 0.64 g of the title compound, 2-(3-hydroxyphenyl)cyclopropyl n-hexyl ketone, as a thick yellow oil in a 76% isolated yield.

300 MHz $^1$H NMR (CDCl$_3$, tms=0 ppm): 0.8(m, 3H); 1.2(m, 7H); 1.4(m, 3H); 2.1 (m, 1H); 2.4(m, 1H); 2.5(t, 2H); 6.5(bs, 1H); 6.6(m, 3H); 7.2(t, 1H).

Preparation of Methyl (E)-3-methoxy-2-trans-[2-(3-(2-(1-oxo-hept-1-yl)cyclopro)yl)-Dhenoxymethyl)phenyl]-2-propenoate.

To a 20 ml glass vial equipped with a magnetic stirring bar was charged 0.64 g (0.0026 moles) of, 2-(3-hydroxyphenyl) cyclopropyl n-hexyl ketone, 10 mls of dry N, N-dimethylformamide, and 0.1 g (0.0026 moles) of powdered sodium hydroxide. To this mixture was added 0.74 g (0.0026 moles) of methyl α-(2-(bromomethyl)phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford the crude product as a dark amber oil. This material was chromatographed on a mixed bed of neutral alumina and silica gel with 30% ethyl acetate, 70% hexane. The pure fractions were combined, and concentrated under reduced pressure with a rotary evaporator at 45° C. to afford 0.75 g of the title compound, methyl (E)-3-methoxy-2-trans-[2-(3-(2-(1-oxo-hept-1-yl)cyclopropyl) phenoxymethyl)phenyl]-2-propenoate as a viscous pale brown oil in a 65% isolated yield.

300 MHz $^1$H NMR (CDCl$_3$, tms=0 ppm): 0.8(m, 3H); 1.2(m, 7H); 1.4(m, 3H); 2.1 (m, 1H); 2.4(m, 1H); 2.5(t, 2H); 3.7(s, 3H); 3.8(s, 3H); 4.9(s, 2H); 6.6(m, 3H); 7.1(m, 2H); 7.3(m, 2H); 7.4(m, 1H); 7.6(s, 1H).

Preparation of Methyl (E)-3-methoxy-2-trans-[2-(3-(2-(methoximinohept-1-yl)cyclopropyl)-phenoxymethyl) phenyl]-2-propenoate.

To a 50 ml round bottom flask equipped with a magnetic stirrer was charged 0.75 g (0.0017 moles) of methyl (E)-3-methoxy-2-trans-[2-(3-(2-(1-oxo-hept-1-yl)cyclopropyl)

phenoxymethyl)phenyl]-2-propenoate, 25 ml of anhydrous methanol, and 0.17 g (0.002 moles) of methoxylamine hydrochloride. The reaction was stirred at ambient temperature overnight, then poured into 100 mls of water and extracted with 3×50 mls of ethyl ether. The ether extract was then washed with 2×50 mls of water and 50 mls of saturated aqueous sodium chloride solution. The ether extract was then dried over anhydrous magnesium sulfate, filtered, and concentrated under reduced pressure with a rotary evaporator at 45° C. to afford the crude product, which was chromatographed on silica gel with 75% hexane, 25% ethyl acetate. The pure fractions were combined, and concentrated under reduced pressure with a rotary evaporator at 45° C. to afford 0.8 g of the title compound, methyl (E)-3-methoxy-2-trans-[2-(3-(2-(methoximinohept-1-yl)cyclopropyl) phenoxymethyl)phenyl]-2-propenoate as a viscous yellow oil in a 100% isolated yield.

300 MHz $^1$H NMR (CDCl$_3$, tms=0 ppm): 0.8(m, 3H); 1.2(m, 7H); 1.4(m, 3H); 2.1 (m, 1H); 2.4(m, 1H); 2.5(t, 2H); 3.7(s, 3H); 3.75(s, 3H); 3.8(s, 3H); 4.9(s, 2H); 6.6(m, 3H); 7.1(m, 2H); 7.3(m, 2H); 7.4(m, 1H); 7.6(s, 1H).

EXAMPLE 4

Method of Scheme L

Preparation of Methyl (E)-3-methoxy-2-trans-[2-(3-(2-(1-(N-benzoylhydrazinomethylidine)cycloprop-1-yl) cyclopropyl) phenoxymethyl)phenyl]-2-propenoate Compound 4.98, Table 4)

Preparation of (E)-3-methoxy-2-trans-[2-(3-(2-(1-oxo-cycloprop-1-yl)cyclopropyl)phenoxy-methyl)phenyl]-2-propenoate To a 20 ml glass vial equipped with a magnetic stirring bar was charged 2.4 g (0.0117 moles) of, 2-(3-hydroxyphenyl) cyclopropyl cyclopropyl ketone, 20 mls of dry N,N-dimethylformamide, and 0.4 g (0.0117 moles) of powdered sodium hydroxide. To this mixture was added 2.7 g (0.0117 moles) of methyl α-(2-(bromomethyl)phenyl)-β-methoxyacrylate in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford the crude product as an amber oil. This material was chromatographed on a mixed bed of neutral alumina and silica gel with 30% ethyl acetate, 70% hexane. The pure fractions were combined, and concentrated under reduced pressure with a rotary evaporator at 45° C. to afford 3.72 g of the title compound, methyl (E)-3-methoxy-2-trans-[2-(3-(2-(1-oxo-cycloprop-1-yl)cyclopropyl) phenoxymethyl)phenyl]-2-propenoate as a viscous yellow oil in a 78% isolated yield.

300 MHz $^1$H NMR (CDCl$_3$, tms=0 ppm): 0.9(m, 2H); 1.1(m, 2H); 1.4(m, 1H); 1.8 (m, 1H); 2.1(m, 1H); 2.4(m, 1H); 2.6(m, 1H); 3.7(s, 3H); 3.8(s, 3H); 4.9(s, 2H); 6.6(m, 3H); 7.1(m, 2H); 7.4(m, 2H); 7.6(m, 1H); 7.7(s, 1H).

Preparation of Methyl (E)-3-methoxy-2-trans-[2-(3-(2-(1-(N-benzoylhydrazino-methylidine)cycloprop-1-yl) cyclopropyl)phenoxymethyl)phenyl]-2-propenoate.

To a 250 ml round bottom flask equipped with a magnetic stirrer was charged 0.91 g (0.0022 moles) of Methyl (E)-3-methoxy-2-trans-[2-(3-(2-(1-oxo-cycloprop-1-yl) cyclopropyl)phenoxymethyl)phenyl]-2-propenoate, 50 ml of anhydrous methanol, and 0.3 g (0.0022 moles) of benzoic hydrazide. The reaction was stirred at ambient temperature for three days, then poured into 100 mls of water and extracted with 3×50 mls of ethyl ether. The ether extract was then washed with 2×50 mls of water and 50 mls of saturated aqueous sodium chloride solution. The ether extract was then dried over anhydrous magnesium sulfate, filtered, and concentrated under reduced pressure with a rotary evaporator at 45° C. to afford the crude product, which was chromatographed on silica gel with 50% hexane, 50% ethyl acetate. The pure fractions were combined, and concentrated under reduced pressure with a rotary evaporator at 45° C. to afford 0.29 g of the title compound, (a mixture of E and Z hydrazones).methyl (E)-3-methoxy-2-trans-[2-(3-(2-(1-(N-benzoylhydrazino-methylidine)cycloprop-1-yl)cyclopropyl) phenoxymethyl)phenyl]-2-propelloate as a viscous yellow oil in a 26% isolated yield.

300 MHz $^1$H NMR (CDCl$_3$, tms=0 ppm): 0.9(m, 2H); 1.1(m, 2H); 1.4(m, 1H); 1.8 (m, 1H); 2.1(m, 1H); 2.3(m, 1H); 2.6(m, 1H); 3.7(d, 3H); 3.8(d, 3H); 4.9(d, 2H); 6.6(m, 3H); 7.1–7.3(m, 5H); 7.35–7.5(m, 4H); 7.6(s, 1H); 7.8(m, 1H); 9.2(br s, 1H).

Proton NMR data (300 MHz) is provided in Table XVI for typical examples of Tables I to XV and are illustrative of the present invention.

TABLE XVI

| Compd # | |
|---|---|
| 1.04 | 1.6(m, 1H); 1.9(m, 1H); 2.3(m, 1H); 2.8(m, 1H); 3.69–3.7(d, 3H); 3.8–3.83(d, 3H); 3.83–3.95(d, 3H); 4.95–4.97(d, 2H); 6.7(m, 3H); 7.2–7.45(m, 8H); 7.59(s, 1H); 7.9(d, 1H). |
| 1.11A | 1.7(m, 2H); 2.2(s, 3H); 2.65(m, 1H); 2.6–2.8(m, 2H); 3.6(s, 3H); 3.7(s, 3H); 3.87(s, 3H); 4.87(s, 2H); 6.65–6.8(m, 3H); 7.05–7.3(m, 8H); 7.45(m, 1H); 7.48(s, 1H). |
| 1.11B | 1.85(m, 2H); 2.3–2.5(m, 2H); 3.59(s, 3H), 3.68(s, 3H); 3.71(s, 3H); 4.87(s, 2H); 6.6–6.9(m, 4H); 7.1–7.3(m, 7H); 7.45(m, 1H); 7.49(s, 1H). |
| 1.18A | 1.15(m, 1H); 1.4(m, 1H); 1.76(s, 3H); 1.8(m, 1H); 2.1(m, 1H); 3.7(s, 3H); 3.816(s, 3H); 3.822(s, 3H); 4.9(s, 2H); 6.55–6.7(m, 3H); 7.1–7.35(m, 4H); 7.5(m, 1H), 7.59(s, 1H). |
| 1.18B | 1.05–1.25(m, 2H); 1.56(s, 3H); 2.1(m, 1H); 2.55(m, 1H); 3.59(s, 3H); 3.69(s, 3H); 3.72(s, 3H); 4.85(s, 2H); 6.55–6.8(m, 3H); 7–7.73(m, 4H); 7.45(m, 1H); 7.48(s, 1H). |
| 1.23 | 0.8(m, 3H); 1.2(m, 7H); 1.4(m, 3H); 2.1(m, 1H); 2.4(m, 1H); 2.5(t, 2H); 3.7(s, 3H); 3.75(s, 3H); 3.8(s, 3H); 4.9(s, 2H); 6.6(m, 3H); 7.1(m, 2H); 7.3(m, 2H); 7.4(m, 1H); 7.6(s, 1H); |
| 1.24 | 0.81–0.83(d, 6H); 1.05(m, 1H); 1.35–1.55(m, 2H); 1.99(m, 1H); 2.1(m, 1H); 2.15(d, 2H); 3.58(s, 3H); 3.65(s, 3H); 3.66(s, 3H); 4.85(s, 2H); 6.55–6.65(m, 3H); 7–7.25(m, 4H); 7.45(m, 1H) 7.47(s, 1H). |
| 1.33 | 1.1(m, 1H); 1.4–1.8(m, 6H); 1.9–2.1(m, 5H); 2.2(m, 1H); 3.3(m, 1H); 3.7(s, 3H); 3.78–3.82(m, 6H); 4.94(s, 2H); 5.4(bs, 1H); 6.6–6.85(m, 3H); 7–7.74(m, 4H); 7.5(m, 1H); 7.58(s, 1H). |
| 1.34 | 0.6(d, 1H); 0.7(m, 3H); 1.1(m, 2H); 1.5(m, 1H); 2.0(m, 1H); 2.3(m, 1H); 3.7(s, 3H); 3.75(s, 3H); 3.8(s, 3H); 4.9(s, 2H); 6.6(m, 1H); 6.7(d, 2H); 7.1(m, 2H); 7.3(m, 2H); 7.6(m, 1H); 7.7(s, 1H) |
| 1.47 | 0.8(m, 2H); 1.9(m, 1H); 2.8–3(m, 1H); 3.57(s, 3H); 3.64(s, 3H); 3.95(s, 3H); 4.85(s, 2H); 6.6–6.9(m, 3H), 7.–7.3(m, 4H); 7.35–7.4(m, 3H); 7.45(s, 1H); 7.6–7.9(m, 5H). |
| 1.108A | 0.6–0.85(m, 3H); 0.9–1.2(m, 2H); 1.26(t, 3H); 3.55(m, 2H); 1.95(m, 1H); 2.4(m, 1H); 3.7(s, 3H); 3.81(s, 3H); 4–4.15(m, 2H); 4.94(s, 2H); 6.55–6.85(m, 3H); 7.1–7.35(m, 4H); 7.55(m, 1H); 7.58(s, 1H). |
| 1.108B | 0.55(m, 1H); 0.85(m, 1H); 1.0(m, 1H); 1.15(m, 1H); 1.2(t, 3H); 1.25(m, 1H); 1.6(m, 1H); 2.0(m, 1H); 2.2(m, 1H); 2.4(m, 1H); 3.63(s, 3H); 3.75(s, 3H); 4.0(m, 2H); 4.88(s, 2H); 6.55–6.8(m, 3H); 7.05–7.3(m, 4H); 7.45(m, 1H); 7.52(s, 1H). |
| 1.110 | 0.7–0.8(m, 3H); 1–1.15(m, 2H); 1.22–1.28(d, 9H); 1.5–1.6(m, 2H); 1.95(m, 1H); 2.4(m, 1H); 3.7(s, 3H); 3.8(d, 3H); 4.94(s, 2H); 6.55–6.75(m, 3H); 7.1–7.4(m, 4H); 7.55(m, 1H); 7.6(s, 1H); |

TABLE XVI-continued

| Compd # | |
|---|---|
| 1.115 | 0.7–0.8(m, 3H): 1–1.15(m, 2H); 1.45–1.6(m, 2H); 1.99(m, 1H); 2.4(m, 1H); 3.68–3.69(d, 3H); 3.76–3.79(d, 3H); 4.93–4.94(d, 2H); 5.02–5.07(d, 2H); 6.65–6.8(m, 3H); 7.1–7.4(m, 9H); 7.5(m, 1H); 7.58(s, 1H). |
| 2.34 | 0.5–0.8(m, 3H); 0.9–1.2(m, 2H); 1.35–1.55(m, 1H); 1.85–1.95(m, 1H); 2.2–2.4(m, 1H); 2.5(m, 1H); 3.76(s, 3H); 3.77(s, 3H); 3.94(s, 3H); 4.85(s, 2H); 6.5–6.7(m, 2H); 7–7.15(m, 2H); 7.2(s, 1H); 7.25–7.4(m, 1H); 7.45(m, 1H). |
| 3.18A | 1.1(m, 1H); 1.3(m, 1H); 1.69(s, 3H); 1.75(m, 1H); 2.05(m, 1H); 2.81–2.83(d, 3H); 3.75(s, 3H); 3.86(s, 3H); 4.84(s, 2H); 6.5–6.65(m, 4H); 7–7.2(m, 2H); 7.25–7.45(m, 3H). |
| 3.18B | 1.1–1.3(m, 2H); 1.58(s, 3H); 2.15(m, 1H); 2.55(m, 1H); 2.81–2.83(d, 3H); 3.75(s, 3H); 3.86(s, 3H); 4.85(s, 2H); 6.6–6.7(m, 3H); 7–7.15(m, 2H); 7.25–7.8(m, 4H). |
| 3.34 | 0.5–0.75(m, 3H); 0.9–1.2(m, 3H); 1.45(m, 1H); 1.9(m, 1H); 2.3(m, 1H); 2.77–2.8(sd, 3H); 3.7–3.76(d, 3H); 3.84(s, 3H); 4.83(s, 2H); 6.45–6.7(m, 4H); 7–7.2(m, 2H); 7.25–7.5(m, 3H). |
| 4.17 | 0.8(m, 3H); 1.1(m, 3H); 1.2–1.4(m, 3H); 1.8–1.9(m, 2H); 2.2(m, 1H); 3.7(s, 3H); 3.85(s, 3H); 4.9(s, 2H); 6.8(m, 4H); 7.0(m, 1H); 7.2(m, 5H); 7.4(m, 2H); 7.6(m, 3H) |
| 4.98 | 0.9(m, 2H); 1.1(m, 2H); 1.4(m, 1H); 1.8(m, 1H); 2.1(m, 1H); 2.3(m, 1H); 2.6(m, 1H); 3.7(d, 3H); 3.8(d, 3H); 4.9(d, 2H); 6.6(m, 3H); 7.1–7.3(m, 5H); 7.35–7.5(m, 4H); 7.6(s, 1H); 7.8(m, 1H); 9.2(bs, 1H) |

EXAMPLE 5

Numerous compounds of this invention were tested for fungicidal activity in vivo against the diseases described below. The compounds were dissolved a 1:1 mixture of acetone and methanol or N, N-dimethylformamide and diluted with a 2:1:1 mixture of water, acetone, and methanol (by volume) or water, respectively, to achieve the appropriate concentration. The solution was sprayed onto the plants, and allowed to dry (two hours). Then the plants were inoculated with fungal spores. Each test utilized control plants which were sprayed with the appropriate solvent mixture and inoculated. For these protective tests, the plants were inoculated one day after treating the plants with the fungicide compound. The remainder of the technique of each of the tests is given below along with the results for various compounds described herein by the Compound # against the various fungi at a dose of 300 grams per hectare. The results are percent disease control are compared to the untreated check wherein one hundred was rated as complete disease control and zero as no disease control.

Wheat Leaf Rust (WLR)

Pucciitia recoitdita (f. sp. tritici) was cultured on 7-day old wheat (cultivar Fielder) over a 12-day period in the greenhouse. Spores were collected from the leaves by settling on aluminum foil. The spores were cleaned by sieving through a 250-micron opening screen and stored dry. The dried spores were used within one month. A spore suspension was prepared from dry uredia by adding 20 mg (9.5 million spores) per ml of Soltrol oil. The suspension was dispensed into gelatin capsules (0.7 ml capacity) which attach to the oil atomizers. One capsule is used per flat of twenty 2-inch square pots of 7-day old wheat plants, cultivar Fielder After waiting for at least 15 minutes for the oil to evaporate from the wheat leaves, the plants were placed in a dark mist chamber (18–20° C. and 100% relative humidity) for 24 hours. The plants were then placed in the greenhouse and evaluated after 12 days for disease Wheat Leaf Blotch (SNW)

Cultures of Septoria nodorum was maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheesecloth. The spore-containing water suspension was diluted to a spore concentration of $3.0 \times 10^6$ spores per ml. The inoculum was dispersed by a DeVilbiss atomizer over one-week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

Erysiphe graminis(f. sp. tritici) was cultured on wheat seedlings, cultivar Fielder, in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

Sphaerotheca fulgineawas maintained on cucumber plants, cultivar. Bush Champion, in the greenhouse. Inoculum was prepared by placing five to ten heavily mildewed cucumber leaves in a glass jar with 500 ml of water containing one drop of Tween 80 per 100 ml. After shaking the liquid and leaves, the inoculum was filtered through cheese cloth and misted onto the plants with a squirt bottle mister. The spore count was 100, 000 spores/ml. The plants were then placed in the greenhouse for infection and incubation. The plants were scored seven days after inoculation. Disease control values were recorded as percent control.

Tomato Late Blight (TLB)

Cultures of Phytophthora infestans were maintained on green pea-amended agar for two to three weeks. The spores were washed from the agar with water and dispersed with a DeVilbiss atomizer over the leaves of 3-week old Pixie tomato plants which had been previously treated with experimental fungicides. The inoculated plants were placed in a humidity cabinet at 20° C. for 24 hours for infection. The plants were then removed to a controlled environment room at 20° C. and 90% humidity. The plants were scored for disease control after five days.

Grape Downy Mildew (GDM)

Plasiitopara viticola was maintained on leaves of grape plants, cultivar. Delaware, in a controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a DeVilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

Rice Blast (RB)

Cultures of Pyricularia oryzae were maintained on potato dextrose agar for two to three weeks. The spores were washed from the agar with water containing 1 drop of Tween 80 per 100 ml water. After filtering the spore suspension through two layers of cheese cloth, the spore count was adjusted to $5 \times 10^5$. The spore suspension was sprayed onto 12-day old rice plants, cultivar M-1, using a DeVilbiss atomizer. The inoculated plants were placed in a humidity cabinet at 20 C for 36 hours to allow for infection. After the infection period, the plants were placed in the greenhouse. After 6 days, the plants were scored for disease control.

Cucumber Anthracnose (CA)

The fungal pathogen *Colletotrichum lagenarium* was cultured on potato dextrose agar (PDA) in the dark at 22 C for a period of 8 to 14 days. Spores of C. lagenarium were removed from the PDA plates by flooding the plate surface with distilled water, amended with 0.5% v/w of yeast extract. The upper surface of the fungal colony was scraped with a blunt instrument until most of the spores were released into the aqueous environment. The spore suspension was filtered though cheesecloth, and the spore count was adjusted by adding more water, containing the yeast extract, until $3.0 \times 10^6$ spores per ml was achieved.

The chemically-treated cucumber plants were 15-days old, cultivar Bush Champion. The upper leaf surface of the plants were sprayed with the spore suspension until runoff, using a hand-held pump spray bottle. The plants were placed in a fluorescent-lighted mist chamber (12 hr light, 12 hr dark) for 48 hours. After that infection period, the plants were placed in a growth chamber for 3 days at 25 C and 90% humidity. The treated plants were then evaluated for disease control.

Botrytis (BOT)

The fungal pathogen Botrytis cinerea was cultured on potato dextrose agar (PDA) under fluorescent lights (12 hr on, 12 hr off) for a period of 2 to 3 weeks. Spores of *B. cinerea* were removed from the PDA plates by flooding the plate surface with distilled water, amended with 0.5% v/w of yeast extract. The upper surface of the fungal colony was scraped with a rubber instrument until most of the spores were released into the aqueous environment. The spore suspension was filtered though cheesecloth, and the spore count was adjusted by adding more water, containing the yeast extract, until $3.0 \times 10^6$ spores per ml was achieved.

Chemically-treated sweet bell pepper plants were 19-days old, cultivar California Wonder. The entire leaf surface of the plants were sprayed with the spore suspension until runoff, using a DeVilbiss atomizer. The plants were placed in a low light mist chamber (12 hr light, 12 hr dark) at 22 C for 4 or 5 days. The treated plants were then evaluated for disease control.

When tested against wheat leaf rust at 300 grams per hectare compounds 1.04, 1.18A, 1.18B, 1.34, 1.108A, 1.108B, 3.18A, 3.18B, 3.34, 4.17, and 4.98 exhibited 100% control.

When tested against septokia nodorum at 300 grams per hectare compounds 1.18A, 1.18B, 1.23, 1.108B, and 3.34, 4.17, and4.98 exhibited 90% or better control.

When tested against wheat powdery mildew at 300 grams per hectare compounds 1.18A, 1.23, 3.18A, and 3.18B exhibited 90% or better control When tested against cucumber powdery mildew at a dose of 300 grams per hectare, compounds,
1.04, 1.18A, 1.18B, 1.23, 1.24, 1.34, 1.108A, 1.108B, 1.110, 1.115, 2.34, 3.18A, 3.18B, 3.34, 4.17, and 4.98 exhibited greater 90 % or better control.

When tested against tomato late blight at 300 grams/hectare compounds 1.33, 1.47 1.34, 1.18B, 1.115, 2.34, 3.18A, 3.18B, 3.34, and 4.98 exhibited 95% or better control.

When tested against grape downy mildew at 300 grams/hectare compounds 1.18A, 1.18B, 1.23, 1.24, 1.34, 1.108A, 1.108B, 1.115, 3.18B, and 3.34 exhibited 100% control.

When tested against rice blast at 300 grams/hectare compounds 1.24, 1.34, 1.18A, 1.108A, 1.108B, 3.18A and 3.18B exhibited 90% or better control.

When tested against cucumber anthracnose at 300 grams/hectare compounds 1.04, 1.18A, 1.34, 1.108A, 1.108B, 1.110, 1.115, 2.34, 3.18A, 3.18B, 3.34, 4.17, and 4.98 exhibited 95% or better control.

When tested against botrytis at 300 grams/hectare compounds 1.47, 1.108B and 1.115 exhibited 75% or better control.

The compounds of this invention are useful as agricultural fungicides and, as such, can be applied to various loci such as the seed, the soil or the foliage.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15). Other known fungicides which an be combined with the compounds of this invention are dimethomorph, famoxadone, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat *septoria nodorum*, rice sheath blight and rice blast.

EXAMPLE 6

Numerous compounds of this invention were tested for insecticidal activity in vivo against the insects described below. The following test method was used to evaluate compounds of the present invention for insecticidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

AW southern armyworm *Spodoptera eridamia*
BB Mexican bean beetle *Epilachiba varivestis*
MTA two-spotted spider mite *Teranychus uricate*

Observations as percent control were made by visual inspection 24–48 hours after spraying.

When tested against southern army worm at 300 grams/hectare compounds 1.24, 1.18A. 1.110, and 4.98 provided 90% or better control.

When tested against Mexican bean beetle at 300 grams/hectare compounds 1.18A, 1.18B, 1.23, 1.24, 1.33, 1.34, 1.108A, 1.110 and 1.115 provided 100% control.

When tested against two-spotted spider mite at 300 grams/hectare compounds 1.04, 1.18A, 1.18B, 1.23, 1.24, 1.33, 1.34, 1.108A, 1.110 and 1.115 provided 100% control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as systemic application. Alternatively, the active compound may be applied to the soil and contacted therein with the insects and other pests to be controlled. This means of application is referred to as soil application. In another alternative, the active compound may be foliarly applied to the plants to be freed from insects and other pests which feed on the foliage.

Compositions and formulations according to the present invention may also include known pesticidal compounds. This expands the spectrum of activity of the preparation and may give rise to synergism. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999, 999)–99 (99:1) % by weight. For compositions suitable for storage or transportation, the amount of active ingredient is preferably between about 0.5 (1:199)–90 (9:1) % by weight, and more preferably between about 1 (1:99) –75 (3:1) % by weight of the mixture. Compositions suitable for direct application or field application generally contain the active compound in an amount substantially between about 0.0001 (1:999, 999)–95 (19:1) %, preferably between about 0.0005 (1:199, 999)–90 (9:1) % by weight, and more preferably between about 0.001 (1:99, 999)–75 (3:1) % by weight of the mixture. The composition can also be stated as a ratio of the compound to the carrier. In the present invention the weight ratio of these materials (active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide, such as that sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing compounds of Formula I, or the enantiomorphs, salts and complexes thereof with finely divided inert solids which can be organic or inorganic in nature. Materials useful for this purpose include botanical flours, silica, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combating or controlling pests which compromises contacting pests with a combative or toxic amount (i.e. a pesticidally effective amount) of at least one active compound of the invention alone or together with a carrier vehicle (composition or formulation) as noted above. The term contacting as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added adhesives such as polyvinylalcohol-cellulose derivatives or other colloidal materials, such as casein, to improve the adherence of the pesticide to the surface to be protected.

We claim:
1. Compound having the structure

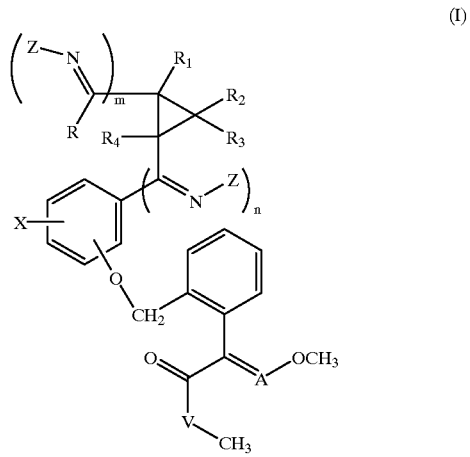

(I)

wherein A is N or CH; V is O or NH;
m and n are the integers 0 and 1, and m+n=1;
X is independently selected from hydrogen, halo, $(C_1-C_4)$ alkyl, and $(C_1-C_4)$alkoxy;
Z is $NR_5R_6$, $OR_5$ or $CR_7R_8R_9$, provided that when $Z=OR_5$, n=0;
R is selected from the group consisting of hydrogen, $(C_1-C_{12})$alkyl, $(C_1-C_{12})$alkoxy, halo$(C_1-C_{12})$alkyl, $(C_2-C_{12})$alkenyl, halo$(C_2-C_{12})$alkenyl, $(C_2-C_{12})$alkynyl, halo$(C_2-C_{12})$alkynyl, halo$(C_1-C_{12})$-alkoxy, $(C_1-C_{12})$alkoxy$(C_1-C_{12})$alkyl, halo$(C_1-C_{12})$alkoxy $(C_1-C_{12})$alkyl, $(C_3-C_7)$cycloalkyl, halo$(C_3-C_7)$ cycloalkyl, $(C_3-C_7)$cycloalkyl$(C_1-C_{12})$alkyl, $(C_3-C_7)$ cycloalkyl$(C_2-C_{12})$alkenyl, $(C_3-C_7)$cycloalkyl $(C_2-C_{12})$alkynyl, $(C_1-C_{12})$alkyl$(C_3-C_7)$cycloalkyl, $(C_1-C_{12})$alkoxy$(C_3-C_7)$cycloalkyl, $(C_1-C_{12})$alkoxy $(C_1-C_{12})$alkyl$(C_3-C_7)$cycloalkyl, $(C_2-C_{12})$alkenyl $(C_3-C_7)$cycloalkyl, $(C_2-C_{12})$ alkynyl$(C_3-C_7)$ cycloalkyl, halo$(C_1-C_{12})$alkyl$(C_3-C_7)$cycloalkyl, $(C_1-C_{12})$alkoxy$(C_2-C_{12})$alkenyl$(C_3-C_7)$cycloalkyl, $(C_1-C_{12})$alkoxy$(C_2-C_{12})$alkynyl$(C_3-C_7)$cycloalkyl, $(C_3-C_7)$cycloalkyl$(C_3-C_7)$-cycloalkyl, $(C_1-C_{12})$alkyl $(C_3-C_7)$cycloalkyl$(C_3-C_7)$cycloalkyl, $(C_2-C_{12})$alkenyl $(C_3-C_7)$cycloalkyl$(C_3-C_7)$cycloalkyl, $(C_2-C_{12})$alkynyl $(C_3-C_7)$cycloalkyl$(C_3-C_7)$cycloalkyl, $(C_3-C_7)$ cycloalkyl$(C_1-C_{12})$alkyl$(C_3-C_7)$cycloalkyl, $(C_3-C_7)$ cycloalkyl$(C_2-C_{12})$alkenyl$(C_3-C_7)$cycloalkyl, $(C_3-C_7)$ cycloalkyl$(C_2-C_{12})$alkynyl$(C_3-C_7)$cycloalkyl, $(C_3-C_7)$ cycloalkyl$(C_1-C_{12})$alkoxy$(C_3-C_7)$cycloalkyl, $(C_3-C_7)$ cycloalkyl$(C_1-C_{12})$alkoxy$(C_1-C_{12})$alkyl$(C_3-C_7)$ cycloalkyl, $(C_3-C_7)$cycloalkyl$(C_1-C_{12})$alkoxy$(C_2-C_{12})$ alkenyl$(C_3-C_7)$cycloalkyl, $(C_3-C_7)$cycloalkyl$(C_1-C_{12})$ alkoxy$(C_2-C_{12})$alkynyl$(C_3-C_7)$cycloalkyl, aryl, aralkyl, aryl$(C_3-C_7)$cycloalkyl, aryl$(C_3-C_7)$cycloalkyl $(C_3-C_7)$cycloalkyl, $(C_3-C_7)$cycloalkylaryl, aryl $(C_1-C_4)$alkyl$(C_3-C_7)$cycloalkyl, heterocyclic, aryl $(C_1-C_4)$alkylheterocyclic, heterocyclic$(C_1-C_4)$alkyl, heterocyclic$(C_3-C_7)$ cycloalkyl, and $C(R_{11})=N-OR_{10}$ provided that when n=1, R and $R_1$ are not both hydrogen;
$R_1$ and $R_4$ are independently selected from the group consisting of hydrogen, halogen, $(C_1-C_{12})$alkyl, $(C_1-C_{12})$alkoxy, halo$(C_1-C_{12})$alkyl, $(C_2-C_{12})$alkenyl, $(C_2-C_{12})$alkynyl, $(C_3-C_7)$cycloalkyl, cyano, carboxy, $(C_1-C_4)$alkoxycarbonyl, $(C_1-C_{12})$alkylcarbonyl, and aryl;

$R_2$ and $R_3$ are selected such that when taken together $R_2$ and $R_3$ form a $(C_3-C_7)$cycloalkyl ring; or are each independently selected from the group consisting of hydrogen, halogen, $(C_1-C_{12})$alkyl, $(C_1-C_{12})$alkoxy, halo$(C_1-C_{12})$alkyl, $(C_2-C_{12})$alkenyl, $(C_2-C_{12})$alkynyl, $(C_3-C_7)$cycloalkyl, cyano, carboxy, $(C_1-C_4)$alkoxycarbonyl, $(C_1-C_{12})$alkylcarbonyl, and aryl;

$R_5$ and $R_6$ are $(C_1-C_{12})$alkyl, $(C_1-C_{12})$alkoxy, halo$(C_1-C_{12})$alkyl, $(C_2-C_{12})$alkenyl, halo$(C_2-C_{12})$alkenyl, $(C_2-C_{12})$alkynyl, halo$(C_2-C_{12})$alkynyl, halo$(C_1-C_{12})$-alkoxy, $(C_1-C_{12})$alkoxy$(C_1-C_{12})$alkyl, $(C_3-C_7)$cycloalkyl, halo$(C_3-C_7)$cycloalkyl, $(C_1-C_4)$alkoxycarbonyl, $(C_1-C_{12})$alkylcarbonyl, arylcarbonyl, aryl, aralkyl, heterocyclic and heterocyclic$(C_1-C_4)$alkyl;

$R_7$, $R_8$, and $R_9$ are independently selected from the group consisting of hydrogen, $(C_1-C_{12})$alkyl, $(C_1-C_{12})$alkoxy, halo$(C_1-C_{12})$alkyl, $(C_2-C_{12})$alkenyl, halo$(C_2-C_{12})$alkenyl, $(C_2-C_{12})$alkynyl, halo$(C_2-C_{12})$alkynyl, halo$(C_1-C_{12})$alkoxy, $(C_1-C_{12})$alkoxy$(C_1-C_{12})$alkyl, $(C_3-C_7)$cycloalkyl, halo$(C_3-C_7)$cycloalkyl, cyano, $(C_1-C_4)$alkoxycarbonyl, $(C_1-C_{12})$alkylcarbonyl, arylcarbonyl, aryl, aralkyl, heterocyclic and heterocyclic$(C_1-C_4)$alkyl;

$R_{10}$ is selected from the group consisting of hydrogen, $(C_1-C_{12})$alkyl, halo$(C_1-C_{12})$alkyl, $(C_2-C_{12})$alkenyl, halo$(C_2-C_{12})$alkenyl, $(C_2-C_{12})$alkynyl, halo$(C_2-C_{12})$alkynyl, $(C_1-C_4)$alkylcarbonyl, $(C_1-C_4)$alkoxycarbonyl, aryl, and aralkyl;

$R_{11}$ is selected from the group consisting of hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_{12})$alkenyl, halo $C_2-C_{12})$alkenyl, $(C_2-C_{12})$alkynyl, halo$(C_2-C_{12})$alkynyl, aryl, aralkyl, heterocyclic, and heterocyclic$(C_1-C_4)$alkyl.

2. The compound of claim 1 wherein A is CH, V is O, and Z is $NR_5R_6$ or $OR_5$.

3. The compound of claim 2 wherein R is selected from the group consisting of $(C_1-C_{12})$alkyl, halo$(C_1-C_{12})$alkyl, heterocyclic, halosubstituted phenyl, $(C_1-C_4)$alkyl substituted phenyl, trihalosubstituted phenyl, $(C_3-C_7)$cycloalkyl, halo$(C_3-C_7)$cycloalkyl, $(C_3-C_7)$cycloalkyl$(C_1-C_{12})$alkyl, $(C_3-C_7)$cycloalkyl$(C_2-C_{12})$alkenyl, $(C_1-C_{12})$alkyl$(C_3-C_7)$cycloalkyl and $(C_2-C_{12})$alkenyl$(C_3-C_7)$cycloalkyl.

4. The compound of claim 1 wherein A is N, V is O or NH, and Z is $NR_5R_6$ or $OR_5$.

5. The compound of claim 4 wherein R is selected from the group consisting of $(C_1-C_{12})$alkyl, halo$(C_1-C_{12})$alkyl, heterocyclic, halosubstituted phenyl, $(C_1-C_4)$alkyl substituted phenyl, trihalosubstituted phenyl, $(C_3-C_7)$cycloalkyl, halo$(C_3-C_7)$cycloalkyl, $(C_3-C_7)$cycloalkyl$(C_1-C_{12})$alkyl, $(C_3-C_7)$cycloalkyl$(C_2-C_{12})$alkenyl, $(C_1-C_{12})$alkyl$(C_3-C_7)$cycloalkyl and $(C_2-C_{12})$alkenyl$(C_3-C_7)$cycloalkyl.

6. The compound of claim 3 wherein n=0 and m=1, Z is $OR_5$ and R is selected from the group consisting of $(C_1-C_{12})$alkyl, cyclopropyl and halosubstituted phenyl.

7. The compound of claim 6 wherein $R_5$ is $(C_1-C_{12})$alkyl.

8. A fungicidal composition for controlling phytopathogenic fungi which comprises an agronomically acceptable carrier and the compound of claim 1 wherein the ratio of the carrier to the compound is 99:1 to 1:4.

9. A method for controlling phytopathogenic fungi which comprises applying the compound of claim to the locus where control is desired at a rate of from 0.005 to 50 kilograms per hectare.

10. A method for controlling insects which comprises applying to the insects' habitat the compound of claim 1 at a rate of 0.005 to 10 kilograms per hectare.

* * * * *